United States Patent
Miyagawa et al.

(10) Patent No.: US 9,771,346 B2
(45) Date of Patent: Sep. 26, 2017

(54) SALT, ACID GENERATOR, RESIST COMPOSITION AND METHOD FOR PRODUCING RESIST PATTERN

(71) Applicant: SUMITOMO CHEMICAL COMPANY, LIMITED, Tokyo (JP)

(72) Inventors: Takayuki Miyagawa, Osaka (JP); Yukako Anryu, Osaka (JP); Koji Ichikawa, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/968,172

(22) Filed: Dec. 14, 2015

(65) Prior Publication Data

US 2016/0168115 A1 Jun. 16, 2016

(30) Foreign Application Priority Data

Dec. 15, 2014 (JP) .................................. 2014-252628

(51) Int. Cl.

| | | |
|---|---|---|
| *C07D 327/06* | (2006.01) | |
| *C07D 327/02* | (2006.01) | |
| *C07D 327/04* | (2006.01) | |
| *C07D 321/04* | (2006.01) | |
| *C07D 321/12* | (2006.01) | |
| *C07D 313/06* | (2006.01) | |
| *C07D 317/72* | (2006.01) | |
| *G03F 7/004* | (2006.01) | |
| *G03F 7/039* | (2006.01) | |
| *G03F 7/20* | (2006.01) | |
| *G03F 7/30* | (2006.01) | |
| *G03F 7/32* | (2006.01) | |
| *G03F 7/38* | (2006.01) | |
| *G03F 7/16* | (2006.01) | |
| *C07C 309/12* | (2006.01) | |
| *C07C 309/06* | (2006.01) | |

(52) U.S. Cl.
CPC .......... *C07D 327/06* (2013.01); *C07C 309/06* (2013.01); *C07C 309/12* (2013.01); *C07D 313/06* (2013.01); *C07D 317/72* (2013.01); *C07D 321/04* (2013.01); *C07D 321/12* (2013.01); *C07D 327/02* (2013.01); *C07D 327/04* (2013.01); *G03F 7/0045* (2013.01); *G03F 7/0397* (2013.01); *G03F 7/168* (2013.01); *G03F 7/2041* (2013.01); *G03F 7/30* (2013.01); *G03F 7/322* (2013.01); *G03F 7/325* (2013.01); *G03F 7/38* (2013.01); *C07C 2603/74* (2017.05)

(58) Field of Classification Search
None
See application file for complete search history.

(56) References Cited

U.S. PATENT DOCUMENTS

| | | |
|---|---|---|
| 2002/0098441 A1 | 7/2002 | Okino et al. |
| 2003/0149225 A1 | 8/2003 | Okino et al. |
| 2004/0043324 A1 | 3/2004 | Okino et al. |
| 2005/0031990 A1 | 2/2005 | Okino et al. |
| 2005/0031991 A1 | 2/2005 | Okino et al. |
| 2005/0037283 A1 | 2/2005 | Okino et al. |
| 2005/0037284 A1 | 2/2005 | Okino et al. |

(Continued)

FOREIGN PATENT DOCUMENTS

| | | |
|---|---|---|
| JP | 2000-122294 A | 4/2000 |
| JP | 2008-209917 A | 9/2008 |

(Continued)

OTHER PUBLICATIONS

Luis et al., "Non Concerted Pathways in the Generation of Dehydroarenes by Thermal Decomposition of Diaryliodonium Carboxylates[1]", Tetrahedron, vol. 45, No. 19, Jul. 1989, pp. 6281-6296.

*Primary Examiner* — Sin Lee

(74) *Attorney, Agent, or Firm* — Birch, Stewart, Kolasch & Birch, LLP

(57) ABSTRACT

A salt represented by formula (I):

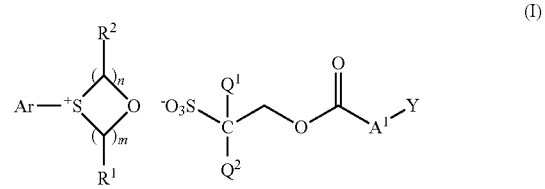

wherein $R^1$ and $R^2$ independently represent a hydrogen atom, a hydroxy group or a $C_1$ to $C_{12}$ hydrocarbon group in which a methylene group may be replaced by a —O— or —CO—; m and n independently represent 1 or 2; Ar represents an optionally substituted phenyl group; $Q^1$ and $Q^2$ independently represent a fluorine atom or a $C_1$ to $C_6$ perfluoroalkyl group, $A^1$ represents a single bond, a $C_1$ to $C_{24}$ alkanediyl group or the like, and Y represents an optionally substituted $C_1$ to $C_{18}$ alkyl group or monovalent $C_3$ to $C_{18}$ alicyclic hydrocarbon group, and a methylene group therein may be replaced by a —O—, O— or —$SO_2$—, provided that the alkyl group or the alicyclic hydrocarbon group has at least one substituent, or at least one methylene group contained therein is replaced by a —O—, —CO— or —$SO_2$—.

7 Claims, No Drawings

(56) References Cited

U.S. PATENT DOCUMENTS

| | | |
|---|---|---|
| 2005/0048400 A1 | 3/2005 | Okino et al. |
| 2008/0193874 A1 | 8/2008 | Takata et al. |
| 2009/0226842 A1* | 9/2009 | Shimizu ............... G03F 7/0045 430/281.1 |
| 2010/0035180 A1 | 2/2010 | Shimada et al. |
| 2010/0151380 A1 | 6/2010 | Ando et al. |
| 2010/0203446 A1 | 8/2010 | Ichikawa et al. |
| 2011/0171576 A1 | 7/2011 | Yamaguchi et al. |
| 2011/0200935 A1 | 8/2011 | Masuyama et al. |
| 2011/0201823 A1 | 8/2011 | Yoshida et al. |
| 2012/0088190 A1 | 4/2012 | Ichikawa et al. |
| 2012/0122032 A1 | 5/2012 | Anryu et al. |
| 2012/0328986 A1 | 12/2012 | Anryu et al. |
| 2013/0017501 A1 | 1/2013 | Nakamura et al. |
| 2013/0143157 A1 | 6/2013 | Tanaka et al. |
| 2014/0308605 A1* | 10/2014 | Ito ......................... G03F 7/0045 430/18 |
| 2016/0062233 A1* | 3/2016 | Masuyama ........... G03F 7/0045 430/270.1 |

FOREIGN PATENT DOCUMENTS

| | | |
|---|---|---|
| JP | 2010-061117 A | 3/2010 |
| JP | 2010-204634 A | 9/2010 |
| JP | 2010-204646 A | 9/2010 |
| JP | 2011-039502 A | 2/2011 |
| JP | 2011-191745 A | 9/2011 |
| JP | 2012-006908 A | 1/2012 |
| JP | 2012-041274 A | 3/2012 |
| JP | 2012-072109 A | 4/2012 |
| JP | 2012-97074 A | 5/2012 |
| JP | 2012-224611 A | 11/2012 |
| JP | 2012-229206 A | 11/2012 |
| JP | 2013-003155 A | 1/2013 |
| JP | 2013-011905 A | 1/2013 |
| JP | 2013-068914 A | 4/2013 |
| WO | WO 2013/100189 A1 * | 7/2013 |

* cited by examiner

US 9,771,346 B2

SALT, ACID GENERATOR, RESIST COMPOSITION AND METHOD FOR PRODUCING RESIST PATTERN

CROSS-REFERENCE TO RELATED APPLICATIONS

This application claims priority to Japanese Application No. 2014-252628 filed on Dec. 15, 2014. The entire disclosures of Japanese Application No. 2014-252628 is incorporated hereinto by reference.

BACKGROUND

1. Field of the Invention

The disclosure relates to a salt, an acid generator, a resist composition and a method for producing resist pattern.

2. Related Art

In the production of semiconductor integrated circuits, ion implantation has been conducted using a resist pattern in order to dope impurities into the semiconductor substrate. A resist composition which contains a salt represented by the following formula as an acid generator is described in Patent document of JP 2012-224611A.

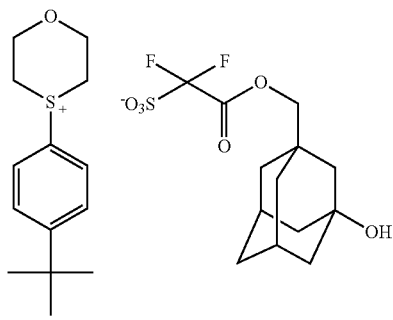

SUMMARY

The present disclosure provides following inventions of <1> to <7>.

<1> A Salt Represented by Formula (I):

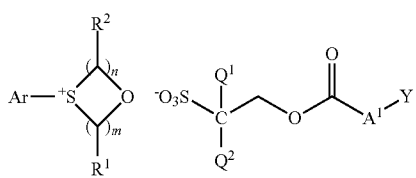

wherein $R^1$ and $R^2$ each independently represent a hydrogen atom, a hydroxy group or a $C_1$ to $C_{12}$ hydrocarbon group in which a methylene group may be replaced by an oxygen atom or a carbonyl group;

m and n each independently represent 1 or 2;

Ar represents an optionally substituted phenyl group;

$Q^1$ and $Q^2$ each independently represent a fluorine atom or a $C_1$ to $C_6$ perfluoroalkyl group, $A^1$ represents a single bond, a $C_1$ to $C_{24}$ alkanediyl group or *-$A^2$-$X^1$-($A^3$-$X^2$)$_a$-($A^4$)$_b$,

* represents a binding site to a carbonyl group;

$A^2$, $A^3$ and $A^4$ each independently represent a $C_1$ to $C_6$ alkanediyl group, $X^1$ and $X^2$ each independently represent —O—, —CO—O— or —O—CO—, a represents 0 or 1, b represents 0 or 1, and Y represents a hydrogen atom or a monovalent $C_3$ to $C_{18}$ alicyclic hydrocarbon group where a hydrogen atom may be replaced by a substituent and where a methylene group may be replaced by an oxygen atom, a carbonyl group or a sulfonyl group, provided that the alicyclic hydrocarbon group has a substituent, or a methylene group contained in the alicyclic hydrocarbon group has been replaced by an oxygen atom, a carbonyl group or a sulfonyl group.

<2> The salt according to <1>, wherein $A^1$ is a single bond.

<3> The salt according to <1> or <2>, wherein Y is a $C_3$ to $C_{18}$ alicyclic hydrocarbon group where a hydrogen atom has been replaced by a substituent or where a methylene group has been replaced by an oxygen atom, a carbonyl group or a sulfonyl group.

<4> An acid generator, which has the salt according to any one of <1> to <3>.

<5> A resist composition contains the salt according to any one of <1> to <4> and a resin having an acid-labile group.

<6> The resist composition according to <5>, further contains a salt which generates an acid weaker in acidity than an acid generated from the acid generator.

<7> A method for producing a resist pattern includes steps (1) to (5);

(1) applying the resist composition according to <5> onto a substrate;

(2) drying the applied composition to form a composition layer;

(3) exposing the composition layer;

(4) heating the exposed composition layer; and (5) developing the heated composition layer.

DETAILED DESCRIPTION OF THE EMBODIMENT

In the specification, the term "(meth)acrylic monomer" means a monomer having a structure of "$CH_2$=CH—CO—" or "$CH_2$=C($CH_3$)—CO—", as well as "(meth)acrylate" and "(meth)acrylic acid" mean "an acrylate or methacrylate" and "an acrylic acid or methacrylic acid," respectively. Herein, chain structure groups include those having a linear structure and those having a branched structure. Unless otherwise specified, the term "aliphatic hydrocarbon group" means a chain aliphatic hydrocarbon group. The indefinite articles "a" and "an" are taken as the same meaning as "one or more".

The term "solid components" means components other than solvents in a resist composition.

<Salt (I)>

The salt of the present disclosure is a salt represented by formula (I), which is sometimes referred to as "salt (I)":

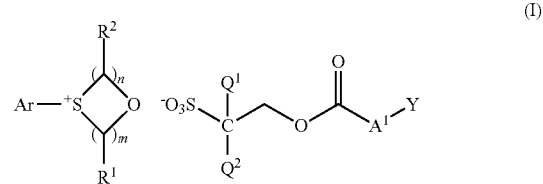

wherein $R^1$ and $R^2$ each independently represent a hydrogen atom, a hydroxy group or a $C_1$ to $C_{12}$ hydrocarbon group in which a methylene group may be replaced by an oxygen atom or a carbonyl group;

m and n each independently represent 1 or 2;

Ar represents an optionally substituted phenyl group;

$Q^1$ and $Q^2$ each independently represent a fluorine atom or a $C_1$ to $C_6$ perfluoroalkyl group, $A^1$ represents a single bond, a $C_1$ to $C_{24}$ alkanediyl group or $*-A^2-X^1-(A^3-X^2)_a-(A^4)_b$, \* represents a binding site to a carbonyl group;

$A^2$, $A^3$ and $A^4$ each independently represent a $C_1$ to $C_6$ alkanediyl group, $X^1$ and $X^2$ each independently represent —O—, —CO—O— or —O—CO—, a represents 0 or 1, b represents 0 or 1, and Y represents a hydrogen atom or a monovalent $C_3$ to $C_{18}$ alicyclic hydrocarbon group where a hydrogen atom may be replaced by a substituent or where a methylene group may be replaced by an oxygen atom, a carbonyl group or a sulfonyl group, provided that the alicyclic hydrocarbon group has at least one substituent, or a methylene group contained in the alicyclic hydrocarbon group has been replaced by an oxygen atom, a carbonyl group or a sulfonyl group.

The hydrocarbon group for $R^1$ and $R^2$ includes an alkyl group, an alicyclic hydrocarbon group, an aromatic hydrocarbon group and a combination thereof.

Examples of the alkyl group include methyl, ethyl, n-propyl, isopropyl, n-butyl, sec-butyl, tert-butyl, pentyl, hexyl, heptyl, 2-ethylhexyl, octyl, nonyl, decyl and undecyl groups.

The alicyclic hydrocarbon group includes any of a monocyclic group and a polycyclic hydrocarbon group. Examples of the monocyclic alicyclic hydrocarbon group include a cycloalkyl group such as cyclopropyl, cyclobutyl, cyclopentyl, cyclohexyl, methylcyclohexyl, dimethylcyclohexyl, cycloheptyl, cyclooctyl and cyclodecyl groups. Examples of the polycyclic alicyclic hydrocarbon group include decahydronaphthyl, adamantyl, 2-alkyladamantane-2-yl, 1-(adamantane-1-yl)alkane-1-yl, norbornyl, methylnorbornyl and isobornyl groups.

Examples of the aromatic hydrocarbon group include phenyl and naphthyl groups.

Examples of the combination of the alkyl group, the alicyclic hydrocarbon group and the aromatic hydrocarbon group include an aralkyl group such as benzyl and phenethyl groups.

Example of a group in which a methylene group contained in the hydrocarbon group is replaced by an oxygen atom or a carbonyl group include methoxy, ethoxy, butoxy, acetyl, methoxycarbonyl, acetyloxy, butoxycarbonyl and benzoyloxy groups.

m is preferably 2.

n is preferably 2.

At least one of m and n is preferably 2, and both of m and n are more preferably 2.

$R^1$ is preferably a hydrogen atom.

$R^2$ is preferably a hydrogen atom.

Both of $R^1$ and $R^2$ are preferably a hydrogen.

Examples of the substituent for Ar include a hydroxy group, a $C_1$ to $C_{12}$ alkyl group, a $C_1$ to $C_{12}$ alkoxy group, a $C_2$ to $C_{18}$ alkoxycarbonyl group, a $C_7$ to $C_{18}$ arylcarbonyloxy group and a $C_2$ to $C_{18}$ alkoxycarbonyloxy group, and methylene group contained in the alkoxy group is replaced by an oxygen atom.

The substituent for Ar is preferably a hydroxy group, a $C_1$ to $C_{12}$ alkyl group, or a $C_1$ to $C_{12}$ alkoxy group, more preferably a $C_1$ to $C_{12}$ alkyl group, and still more preferably a $C_1$ to $C_4$ alkyl group.

Examples of the alkyl group include the same ones as described in $R^1$ and $R^2$.

Examples of the alkoxyl group include methoxy, ethoxy, propoxy, butoxy, pentyloxy, hexyloxy, heptyloxy, octyloxy, decyloxy and dodecyloxy groups. The alkoxyl group is preferably a $C_1$ to $C_6$ alkoxy group, and more preferably a methoxy group.

Examples of the alkylcarbonyloxy group include methylcarbonyloxy, ethylcarbonyloxy, n-propylcarbonyloxy, iso-propylcarbonyloxy, n-butylcarbonyloxy, sec-butylcarbonyloxy, tert-butylcarbonyloxy, pentylcarbonyloxy, hexylcarbonyloxy, octylcarbonyloxy and 2-ethylhexylcarbonyloxy groups. The alkylcarbonyloxy group is preferably a $C_2$ to $C_{12}$ alkylcarbonyloxy, and more preferably a methylcarbonyloxy group.

Examples of the arylcarbonyloxy group include phenylcarbonyloxy group and tocylcarbonyloxy group. The arylcarbonyloxy group is preferably a $C_7$ to $C_{12}$ arylcarbonyloxy group, and more preferably a phenylcarbonyloxy group.

Examples of the alkoxycarbonyloxy group include methoxycarbonyloxy, ethoxycarbonyloxy, n-propoxycarbonyloxy, iso-propoxycarbonyloxy, n-butoxycarbonyloxy, sec-butoxycarbonyloxy, tert-butoxycarbonyloxy, pentyloxycarbonyloxy, hexyloxycarbonyloxy, octyloxycarbonyloxy and 2-ethylhexyloxycarbonyloxy groups. The alkoxycarbonyloxy group is preferably a $C_2$ to $C_8$ alkyloxycarbonyloxy group, and more preferably a tert-butoxycarbonyloxy group.

Ar is preferably a phenyl group in which a hydrogen atom may be replaced by an alkyl group or an alkoxy group, and more preferably a phenyl group in which a hydrogen atom may be replaced by an alkyl group.

Examples of a cation in the salt (I) include those represented by the following ones.

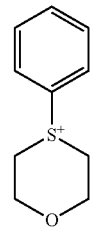

(I-c-1)

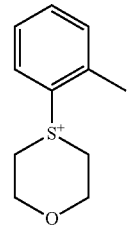

(I-c-2)

(I-c-3)
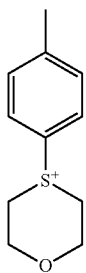
(I-c-4)
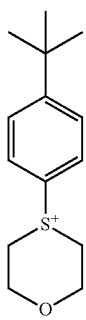
(I-c-5)
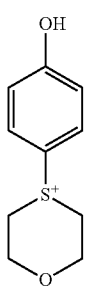
(I-c-6)
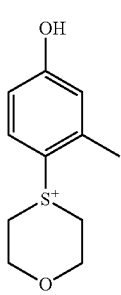
(I-c-7)
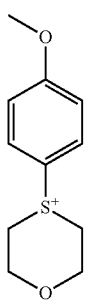
(I-c-8)
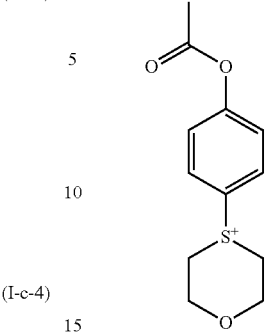
(I-c-9)
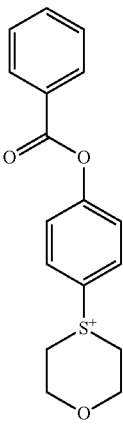
(I-c-10)
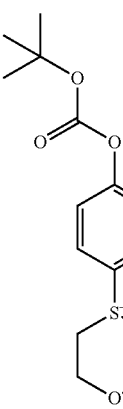
(I-c-11)
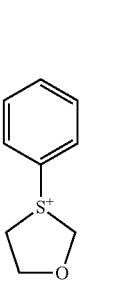

-continued (I-c-12)

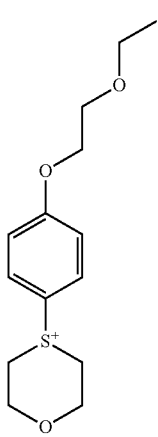

(I-c-13)

Among these, cations represented by formulae (I-c-1), (I-c-3), (I-c-4), (I-c-7), (I-c-12) and (I-c-13) are preferred, and cations represented by formulae (I-c-1), (I-c-3) and (I-c-4) are more preferred.

Examples of the perfluoroalkyl group for $Q^1$ and $Q^2$ include trifluoromethyl, perfluoroethyl, perfluoropropyl, perfluoro-isopropyl, perfluorobutyl, perfluoro-sec-butyl, perfluoro-tert-butyl, perfluoropentyl and perfluorohexyl groups.

$Q^1$ and $Q^2$ each independently are preferably a trifluoromethyl group or a fluorine atom, and both of $Q^1$ and $Q^2$ are more preferably a fluorine atom.

Examples of the alkanediyl group for $A^1$, $A^2$, $A^3$ and $A^4$ include a liner alkanediyl group such as methylene, ethylene, propane-1,3-diyl, butane-1,4-diyl, pentane-1,5-diyl and hexane-1,6-diyl groups;

a branched alkanediyl group such as ethane-1,1-diyl, propane-1,2-diyl, butane-1,3-diyl, 2-methylpropane-1,3-diyl, 2-methylpropane-1,2-diyl, pentane-1,4-diyl and 2-methylbutane-1,4-diyl groups.

Examples of **-$A^2$-$X^1$-($A^3$-$X^2$)$_a$-($A^4$)$_b$- include *-$A^2$-O—, *-$A^2$-CO—O—, *-$A^2$-CO—O-$A^4$-, *-$A^2$-O—CO—, *-$A^2$-CO—O-$A^3$-CO—O—, *-$A^2$-CO—O-$A^3$-CO—O-$A^4$-, *-$A^2$-O—CO-$A^3$-O—, *-$A^2$-O-$A^3$-CO—O—, *-$A^2$-CO—O-$A^3$-O—CO—, *-$A^2$-O—CO-$A^3$-O—CO—. Among these, *-$A^2$-O— and *-$A^2$-O—CO— are preferred. * represents a binding site to a carbonyl group.

$A^2$, $A^3$ and $A^4$ are preferably a $C_1$ to $C_4$ divalent alkanediyl group.

$A^1$ is preferably a $C_1$ to $C_6$ alkanediyl group, a single bond or *-$A^2$-$X^1$—, more preferably a single bond or *—CH$_2$—O—CO—, and still more preferably a single bond.

$X^1$ is preferably *—O—CO—, where * represents a binding site to $A^2$ or $A^3$.

Examples of the monovalent alicyclic hydrocarbon group for Y include groups represented by formula (Y1) to formula (Y11).

Examples of the monovalent alicyclic hydrocarbon group for Y in which a methylene group has been replaced by an oxygen atom, a carbonyl group or a sulfonyl group include groups represented by formula (Y12) to formula (Y27).

(Y1)

(Y2)

(Y3)

(Y4)

(Y5)

(Y6)

(Y7)

(Y8)

(Y9)

(Y10)

(Y11)

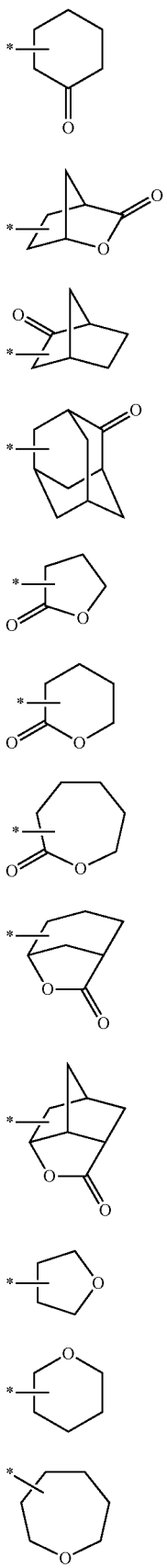
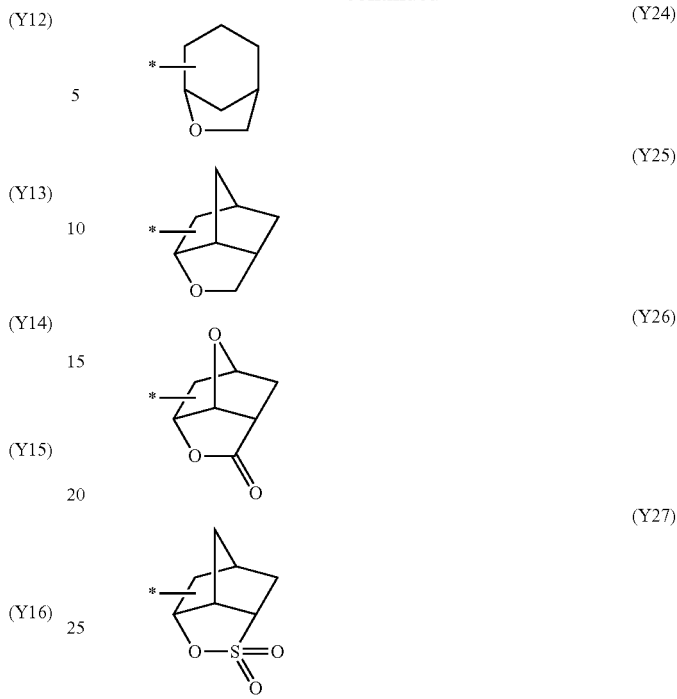

Among these, the alicyclic hydrocarbon group is preferably any one of groups represented by the formula (Y1) to the formula (Y20), more preferably any one of groups represented by the formula (Y11), (Y15), (Y16) or (Y20), and still more preferably group represented by the formula (Y11) or (Y15).

Examples of the substituent of the alicyclic hydrocarbon group for Y include a halogen atom, a hydroxyl group, a $C_1$ to $C_{12}$ alkyl group, a hydroxy group-containing $C_1$ to $C_{12}$ alkyl group, a $C_3$ to $C_{16}$ monovalent alicyclic hydrocarbon group, a $C_1$ to $C_{12}$ alkoxy group, a $C_6$ to $C_{18}$ monovalent aromatic hydrocarbon group, a $C_7$ to $C_{21}$ aralkyl group, a $C_2$ to $C_4$ acyl group, a glycidyloxy group and —$(CH_2)_{j2'}$—O—CO—$R^{b1}$—, in which $R^{b1}$ represents an $C_1$ to $C_{16}$ alkyl group, a $C_3$ to $C_{16}$ monovalent alicyclic hydrocarbon group, or a $C_6$ to $C_{18}$ monovalent aromatic hydrocarbon group, and j2' represents an integer of 0 to 4.

Examples of the hydroxy group-containing alkyl group include hydroxymethyl and hydroxyethyl groups.

Examples of the alkoxyl group include methoxy, ethoxy, propoxy, butoxy, pentyloxy, hexyloxy, heptyloxy, octyloxy, decyloxy and dodecyloxy groups.

Examples of the aromatic hydrocarbon group include an aryl group such as phenyl, naphthyl, anthryl, p-methylphenyl, p-tert-butylphenyl, p-adamantylphenyl, tolyl, xylyl, cumenyl, mesityl, biphenyl, phenanthryl, 2,6-diethylphenyl and 2-methyl-6-ethylphenyl groups.

Examples of the aralkyl group include benzyl, phenethyl, phenylpropyl, naphthylmethyl and naphthylethyl groups.

Examples of the acyl group include acetyl, propionyl and butyryl groups.

Examples of the halogen atom include fluorine, chlorine, bromine and iodine atoms.

Y is preferably a $C_3$ to $C_{18}$ alicyclic hydrocarbon group where a hydrogen atom may be replaced by a substituent or where a methylene group may be replaced by an oxygen atom, a carbonyl group or a sulfonyl group, more preferably an adamantyl group in which a hydrogen atom may be replaced by a substituent and a methylene group may be replaced by an oxygen atom, a carbonyl group or a sulfonyl group, and still more preferably an adamantyl group, a hydroxyadamantyl group, an oxoadamantyl group, or an adamantyl group having a cyclic ketal structure such as the following groups.

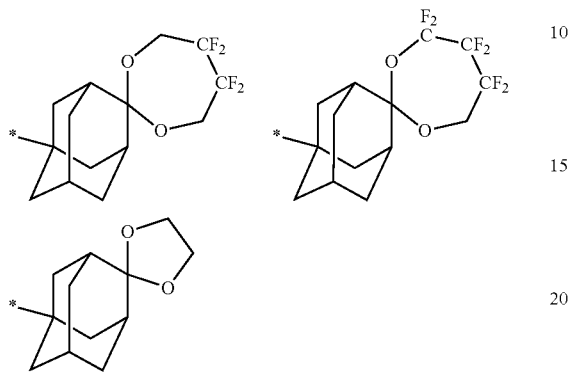

Examples of an anion in the salt (I) include the anions represented by the following ones.

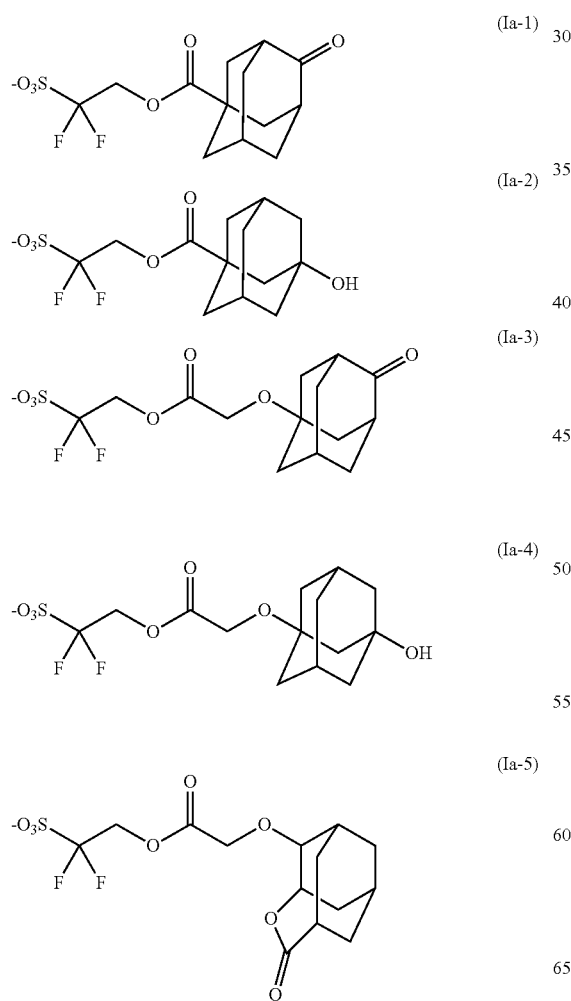

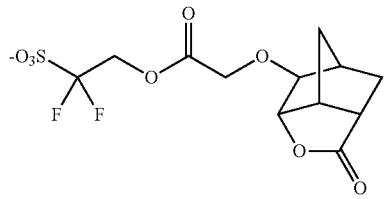

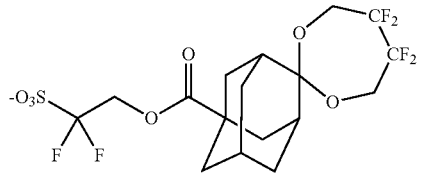

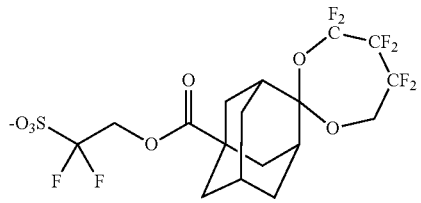

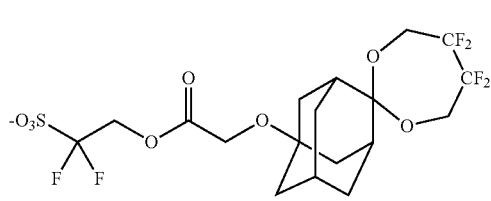

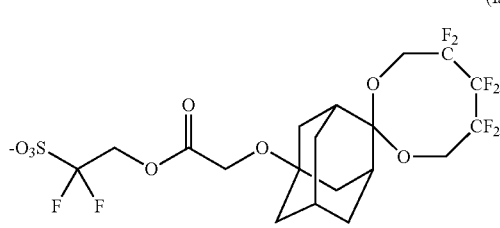

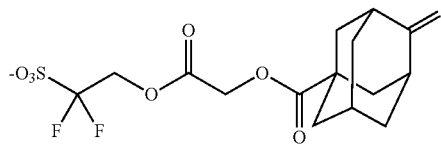

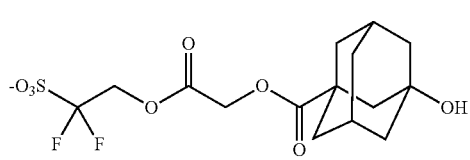

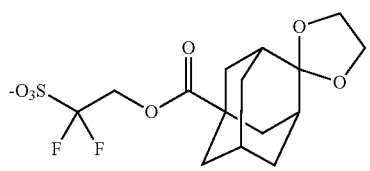

Specific examples thereof include salts illustrating in Table 1. In the table, each symbol in the columns represents that of the formula which represents one of the above-mentioned anions and cations. For example, the salt (I-1) consists of the cation of formula (I-c-1) and the anion of formula (Ia-1).

In Table 1, the salt (I-1) is the following one.

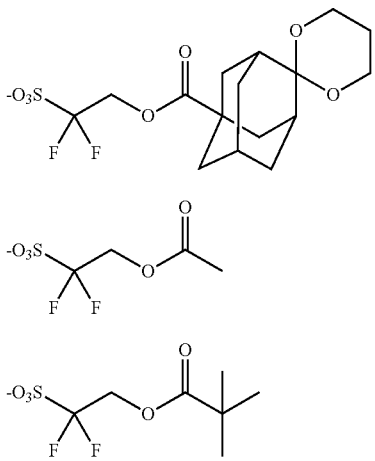

(I-1)

TABLE 1

| Salt (I) | Anion | Cation |
| --- | --- | --- |
| (I-1) | (Ia-1) | (I-c-1) |
| (I-2) | (Ia-2) | (I-c-1) |
| (I-3) | (Ia-7) | (I-c-1) |
| (I-4) | (Ia-8) | (I-c-1) |
| (I-5) | (Ia-11) | (I-c-1) |
| (I-6) | (Ia-12) | (I-c-1) |
| (I-7) | (Ia-1) | (I-c-3) |
| (I-8) | (Ia-2) | (I-c-3) |
| (I-9) | (Ia-7) | (I-c-3) |
| (I-10) | (Ia-8) | (I-c-3) |
| (I-11) | (Ia-11) | (I-c-3) |
| (I-12) | (Ia-12) | (I-c-3) |
| (I-13) | (Ia-1) | (I-c-4) |
| (I-14) | (Ia-2) | (I-c-4) |
| (I-15) | (Ia-7) | (I-c-4) |
| (I-16) | (Ia-8) | (I-c-4) |
| (I-17) | (Ia-11) | (I-c-4) |
| (I-18) | (Ia-12) | (I-c-4) |
| (I-19) | (Ia-1) | (I-c-5) |
| (I-20) | (Ia-2) | (I-c-5) |
| (I-21) | (Ia-7) | (I-c-5) |
| (I-22) | (Ia-8) | (I-c-5) |
| (I-23) | (Ia-11) | (I-c-5) |
| (I-24) | (Ia-12) | (I-c-5) |
| (I-25) | (Ia-1) | (I-c-7) |
| (I-26) | (Ia-2) | (I-c-7) |
| (I-27) | (Ia-7) | (I-c-7) |

TABLE 1-continued

| Salt (I) | Anion | Cation |
| --- | --- | --- |
| (I-28) | (Ia-8) | (I-c-7) |
| (I-29) | (Ia-11) | (I-c-7) |
| (I-30) | (Ia-12) | (I-c-7) |
| (I-31) | (Ia-1) | (I-c-8) |
| (I-32) | (Ia-2) | (I-c-8) |
| (I-33) | (Ia-7) | (I-c-8) |
| (I-34) | (Ia-8) | (I-c-8) |
| (I-35) | (Ia-11) | (I-c-8) |
| (I-36) | (Ia-12) | (I-c-8) |
| (I-37) | (Ia-1) | (I-c-10) |
| (I-38) | (Ia-2) | (I-c-10) |
| (I-39) | (Ia-7) | (I-c-10) |
| (I-40) | (Ia-8) | (I-c-10) |
| (I-41) | (Ia-11) | (I-c-10) |
| (I-42) | (Ia-12) | (I-c-10) |
| (I-43) | (Ia-1) | (I-c-12) |
| (I-44) | (Ia-2) | (I-c-12) |
| (I-45) | (Ia-7) | (I-c-12) |
| (I-46) | (Ia-8) | (I-c-12) |
| (I-47) | (Ia-11) | (I-c-12) |
| (I-48) | (Ia-12) | (I-c-12) |
| (I-49) | (Ia-1) | (I-c-13) |
| (I-50) | (Ia-2) | (I-c-13) |
| (I-51) | (Ia-7) | (I-c-13) |
| (I-52) | (Ia-8) | (I-c-13) |
| (I-53) | (Ia-11) | (I-c-13) |
| (I-54) | (Ia-12) | (I-c-13) |
| (I-55) | (Ia-13) | (I-c-1) |
| (I-56) | (Ia-13) | (I-c-3) |
| (I-57) | (Ia-13) | (I-c-4) |
| (I-58) | (Ia-13) | (I-c-5) |
| (I-59) | (Ia-13) | (I-c-7) |
| (I-60) | (Ia-13) | (I-c-8) |
| (I-61) | (Ia-13) | (I-c-10) |
| (I-62) | (Ia-13) | (I-c-12) |
| (I-63) | (Ia-13) | (I-c-13) |
| (I-64) | (Ia-14) | (I-c-1) |
| (I-65) | (Ia-14) | (I-c-3) |
| (I-66) | (Ia-14) | (I-c-4) |
| (I-67) | (Ia-14) | (I-c-5) |
| (I-68) | (Ia-14) | (I-c-7) |
| (I-69) | (Ia-14) | (I-c-8) |
| (I-70) | (Ia-14) | (I-c-10) |
| (I-71) | (Ia-14) | (I-c-12) |
| (I-72) | (Ia-14) | (I-c-13) |
| (I-73) | (Ia-16) | (I-c-1) |
| (I-74) | (Ia-16) | (I-c-3) |
| (I-75) | (Ia-16) | (I-c-4) |
| (I-76) | (Ia-16) | (I-c-5) |
| (I-77) | (Ia-16) | (I-c-7) |
| (I-78) | (Ia-16) | (I-c-8) |
| (I-79) | (Ia-16) | (I-c-10) |
| (I-80) | (Ia-16) | (I-c-12) |
| (I-81) | (Ia-16) | (I-c-13) |

The salts (I) are preferably those which consist of an anion represented by formula (Ia-1), (Ia-2), (Ia-7), (Ia-8), (Ia-11), (Ia-12), (Ia-13) or (Ia-14) and a cation represented by formula (I-c-1), (I-c-3), (I-c-4), (I-c-5), (I-c-7), (I-c-8), (I-c-10), (I-c-12), or (Ia-13), more preferably those represented by the formulae (I-1), (I-2), (I-3), (I-4), (I-7), (I-8), (I-9), (I-10), (I-13), (I-14), (I-15), (I-16), (I-19), (I-20), (I-21), (I-22), (I-49), (I-50), (I-51), (I-52), (I-55), (I-56), (I-57), (I-58), (I-63) and (I-75), and still more preferably those represented by the formulae (I-1), (I-2), (I-3), (I-4), (I-7), (I-8), (I-9), (I-10), (I-13), (I-14), (I-15), (I-16), (I-19), (I-20), (I-21), (I-22), (I-49), (I-50), (I-51), (I-52), (I-55), (I-56), (I-57), (I-58) and (I-63).

<Method for Producing the Salt (I)>

The salt (I) can be produced by reacting a salt represented by formula (I-a) with a compound represented by formula (I-b) in a solvent:

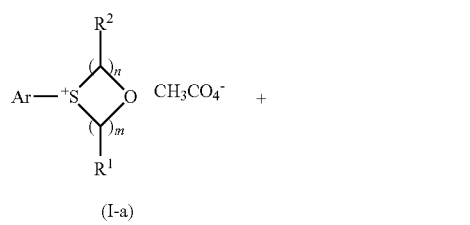

(I-a)

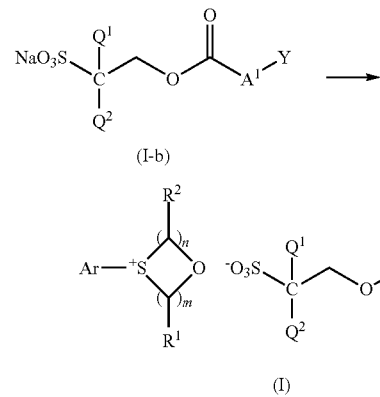

(I-b)

(I)

in which all symbols are as defined above.

Preferred examples of the solvent include acetonitrile and chloroform.

The reaction can be conducted at temperature of preferably 15° C. to 80° C., for 0.5 to 12 hours.

The salt represented by the formula (I-a) can be obtained by reacting a salt represented by formula (I-c) with a compound represented by formula (I-d) in presence of a catalyst in a solvent:

(I-a)

in which all symbols are as defined above.

Preferred examples of the solvent include acetonitrile and chloroform.

Preferred examples of the catalyst include copper (II) acetate.

The reaction can be conducted at temperature of preferably 15° C. to 120° C., for 0.5 to 12 hours.

Examples of the salt represented by the formula (I-c) include the salt represented by formula below which is available on the market.

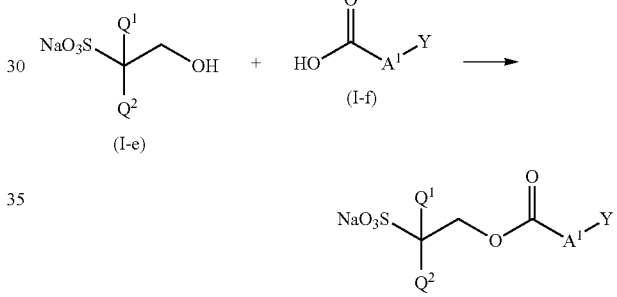

Examples of the compound represented by the formula (I-d) include the compound represented by formula below which is available on the market.

The salt represented by the formula (I-b) can be obtained by reacting a salt represented by formula (I-e) with a compound represented by formula (I-f) in presence of a catalyst in a solvent:

(I-e)  (I-f)

(I-b)

in which all symbols are as defined above.

The reaction can be conducted at temperature of preferably 15° C. to 80° C., for 0.5 to 12 hours.

Preferred examples of the solvent include acetonitrile and chloroform.

Preferred examples of the catalyst include carbonyldiimidazole.

Examples of the compound represented by the formula (I-f) include the compounds represented by formulae below which are available on the market.

The salt represented by formula (I-e) can be obtained by reducing a salt represented by formula (I-g) in a solvent:

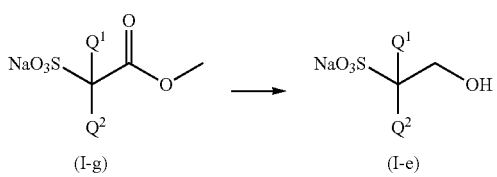

in which all symbols are as defined above.

Preferred examples of the solvent include tetrahydrofuran.

Preferred examples of the reducing agent include lithium aluminum hydride.

The reaction can be conducted at temperature of preferably −5° C. to 60° C., for 0.5 to 12 hours.

The salt represented by formula (I) in which Y represents a $C_3$-$C_{18}$ alicyclic hydrocarbon group which has a cyclic ketal structure can be produced by reacting the salt (I) having an oxoadamantane ring with an acid such as sulfuric acid.

The reaction can be conducted at temperature of preferably 15° C. to 90° C., for 0.5 to 12 hours.

Examples of the compound represented by the formula (I-g) include the compound represented by formulae below which is available on the market.

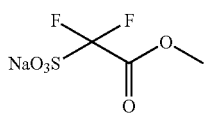

<Acid Generator>

The acid generator of the disclosure is an acid generator having the salt (I) as an active ingredient. The salt (I) may have one kind of the salts (I) or two or more of them. The acid generator may have a known acid generator in this art (which is sometimes referred to as "acid generator (B)") in addition to the salt (I) as an active ingredient. When the acid generator has the salt (I) and the acid generator (B), the weight ratio of the salt (I):the acid generator (B) may be 1:99 to 99:1, preferably 2:98 to 98:2, and more preferably 5:95 to 95:5, and still more preferably 15:85 to 85:15, and particularly preferably 30:70 to 70:30.

<Resist Composition>

The resist composition of the disclosure contains the salt (I) and a resin having an acid-labile group (which is sometimes referred to as "resin (A)"). In the resist composition, the salt (I) is contained as an acid generator.

Here the "acid-labile group" means a group having a leaving group which is detached by contacting with an acid resulting in forming a hydrophilic group such as a hydroxy or carboxy group.

The resist composition preferably further contains a quencher (which is sometimes referred to as "quencher (C)") and/or a solvent (which is sometimes referred to as "solvent (E)").

The resist composition of the disclosure, the proportion of the salt (I) is preferably 1 to 20 parts by mass, more preferably 2 to 15 parts by mass, with respect to 100 parts by mass of the resin (A).

<Acid Generator (B)>

In the resist composition of the disclosure, the acid generator (B) may be any an ionic acid generator and a non-ionic acid generator, and preferably an ionic acid generator. Examples of the ionic acid generator include an acid generator which consists of a known anion and a known cation.

The acid generator (B) includes organic sulfonic acid salts and organic sulfonium salts, which are mentioned in JP2013-68914A, JP2013-3155A and JP2013-11905A.

Preferred acid generators (B1) are acid generators represented by formula (B1-1) to formula (B1-30). Among these, acid generators which contain an arylsulfonium cation are preferred, and acid generators represented by formulae (B1-1), (B1-2), (B1-3), (B1-5), (B1-6), (B1-7), (B1-11), (B1-12), (B1-13), (B1-14), (B1-17), (B1-20), (B1-21), (B1-23), (B1-24), (B1-25), (B1-26) and (B1-29) are more preferred.

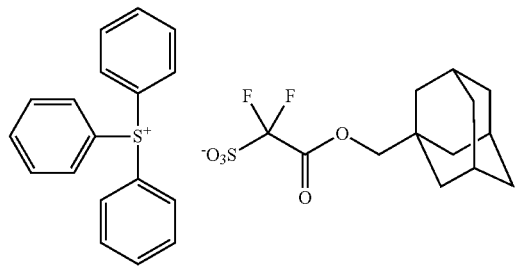

(B1-1)

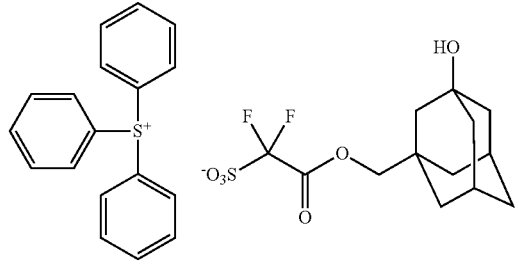

(B1-2)

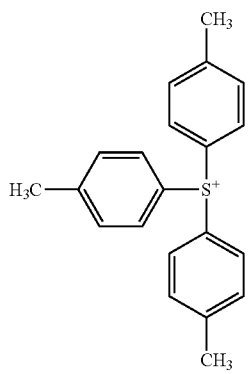

(B1-3)

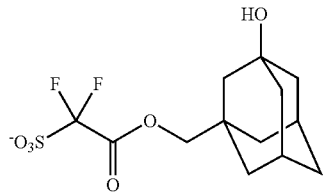

-continued
(B1-4)
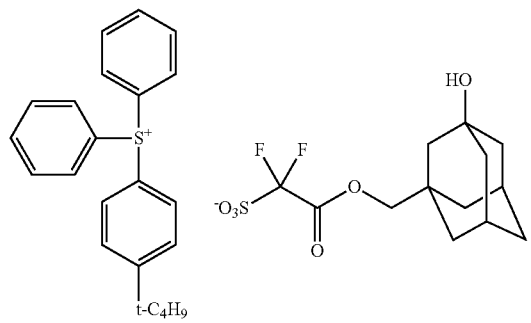
(B1-5)
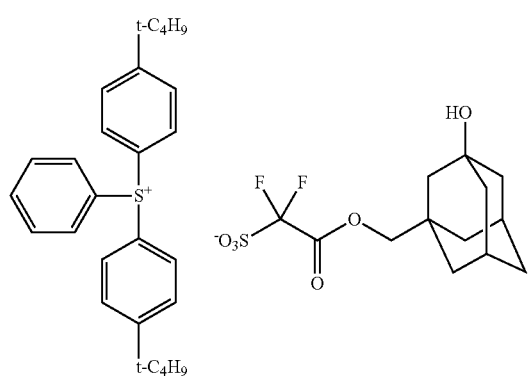
(B1-6)
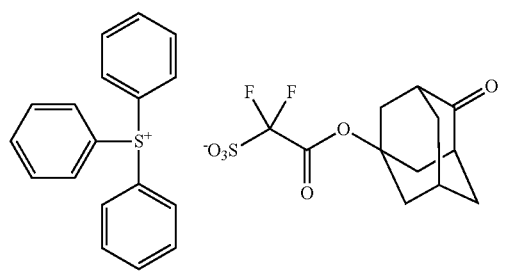
(B1-7)
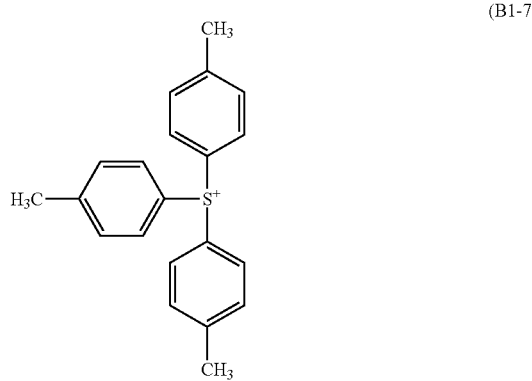
(B1-8)
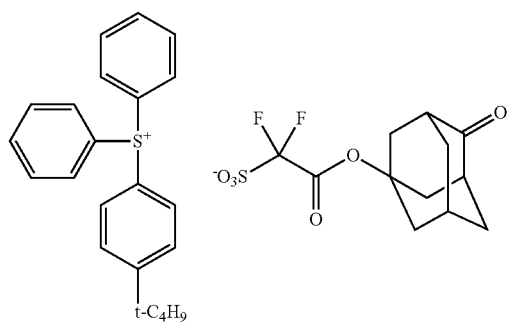
(B1-9)
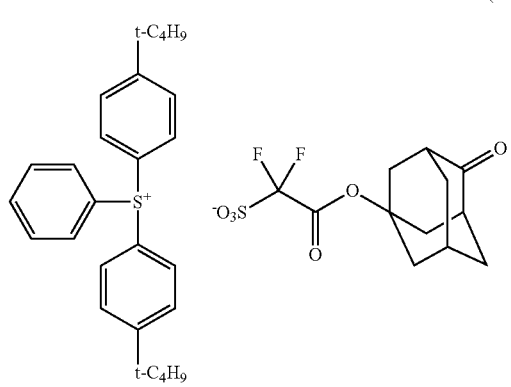
(B1-10)
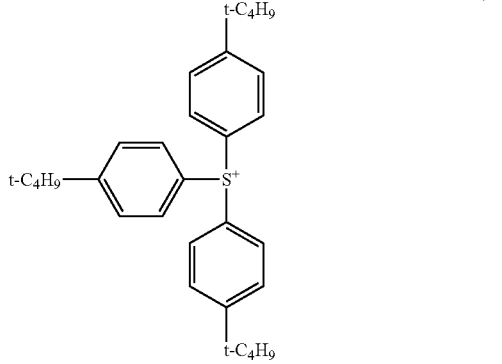
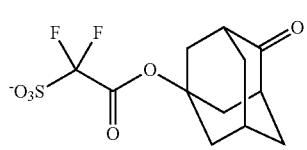
(B1-11)
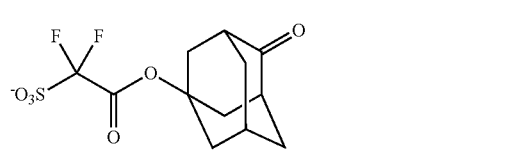

-continued
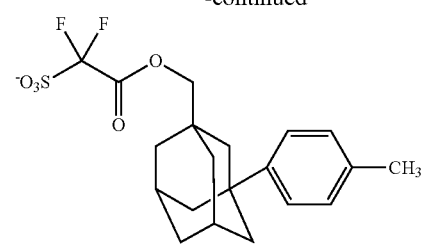
(B1-12)
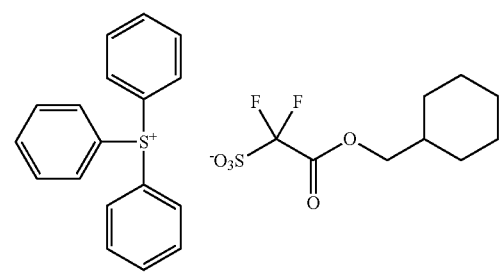
(B1-13)
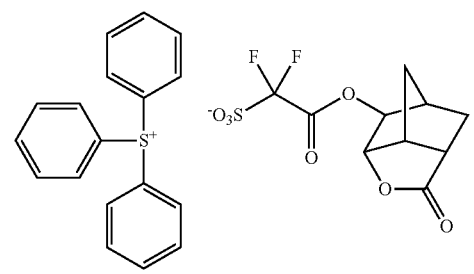
(B1-14)
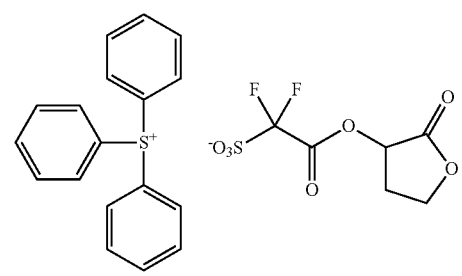
(B1-15)
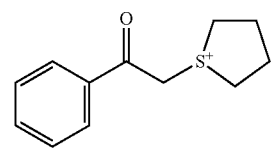
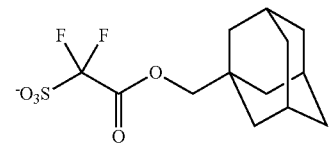
(B1-16)
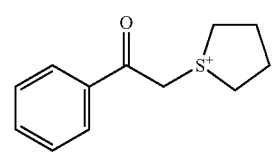
-continued
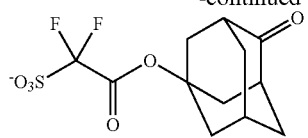
(B1-17)
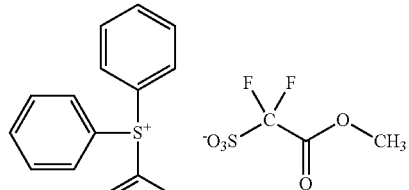
(B1-18)
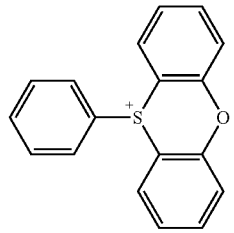
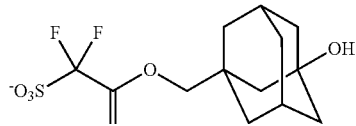
(B1-19)
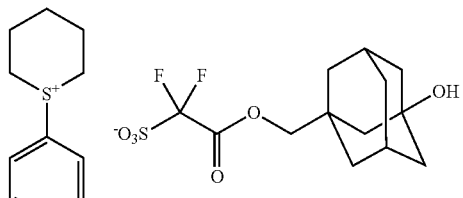
(B1-20)
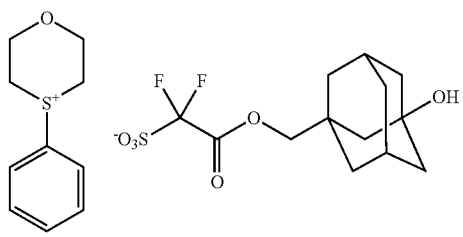
(B1-21)
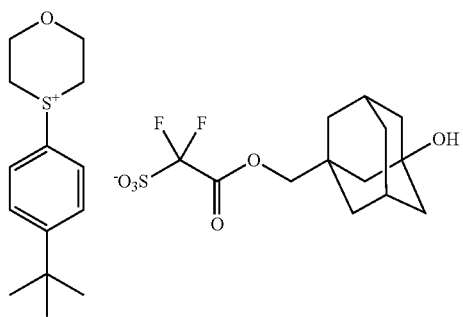

(B1-22)
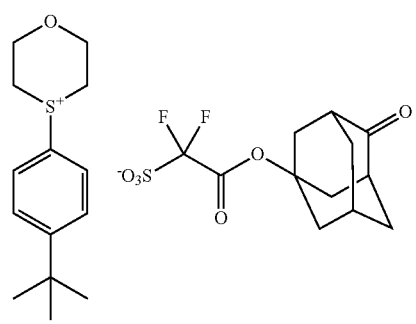
(B1-23)
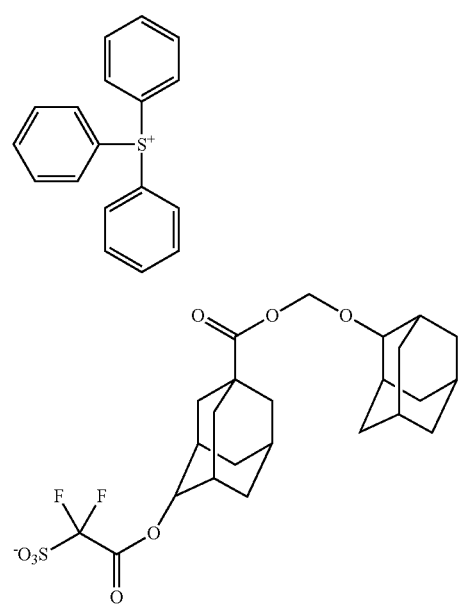
(B1-24)
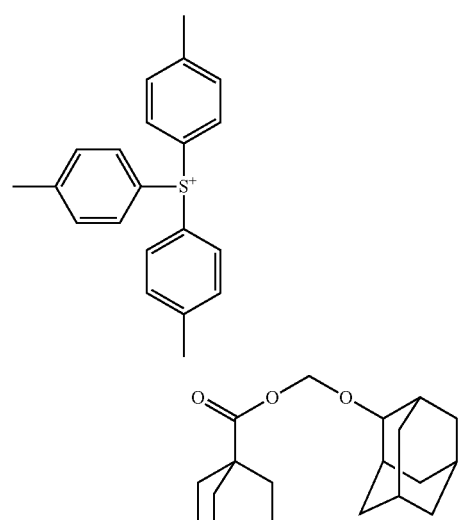
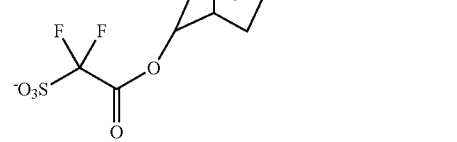
(B1-25)
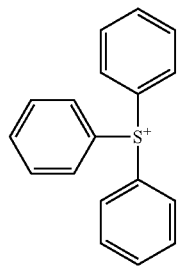
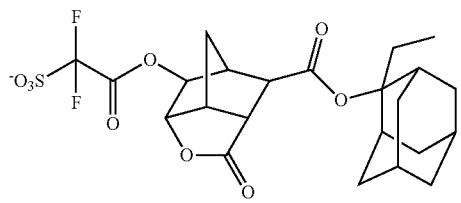
(B1-26)
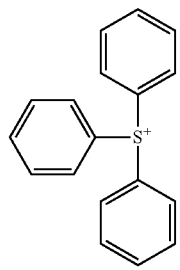
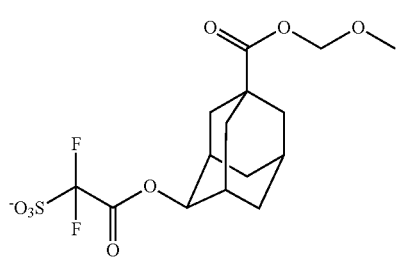
(B1-27)
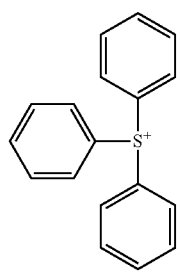
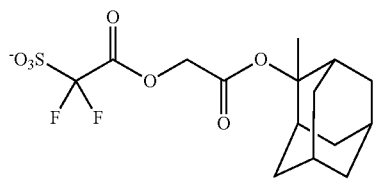

-continued

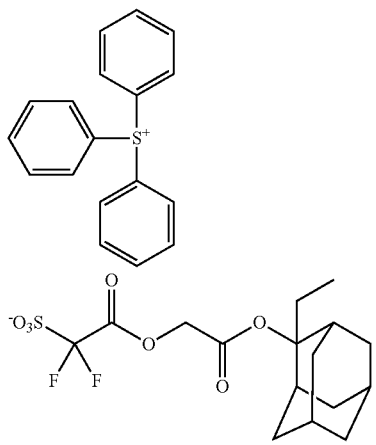

(B1-28)

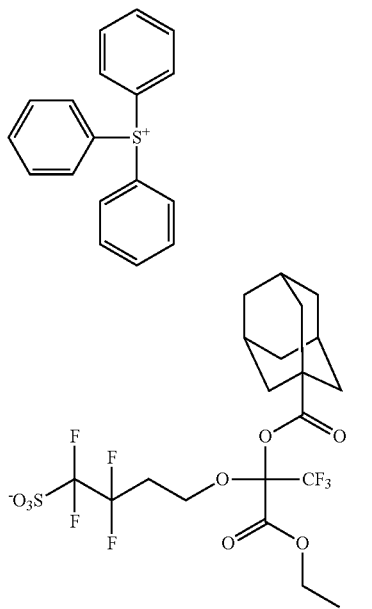

(B1-29)

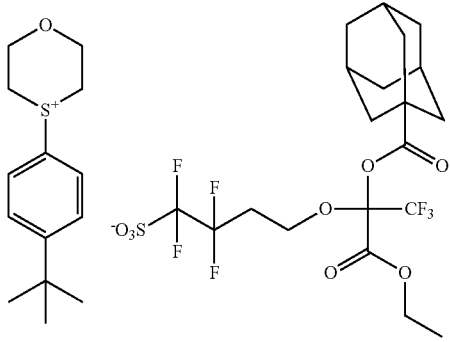

(B1-30)

In the resist composition of the disclosure, the acid generator (B) may have one kind of salt or two or more of them.

In the resist composition of the disclosure, the proportion of the acid generator (B) is preferably 1 part by mass to 20 parts by mass, and more preferably 3 parts by mass to 15 parts by mass with respect to 100 parts by mass of the resin (A).

In the resist composition of the disclosure, when the resist composition contains the salt (I) and the acid generator (B), the total proportion of the salt (I) and the acid generator (B) is preferably 1.5 parts by mass to 40 parts by mass, and more preferably 3 parts by mass to 35 parts by mass with respect to 100 parts by mass of the resin (A).

<Resin (A)>

The resin (A) has a structural unit having an acid-labile group (which is sometimes referred to as "structural unit (a1)"). The resin (A) preferably further has structural unit other than the structural unit (a1). Examples of the structural unit other than the structural unit (a1) includes a structural unit having no acid-labile group (which is sometimes referred to as "structural unit (s)"), another structural unit other than the structural unit (a1) and the structural unit (s), and a structural unit derived from a known monomer in this art.

<Structural Unit (a1)>

The structural unit (a1) is derived from a monomer having an acid-labile group (which is sometimes referred to as "monomer (a1)"). Here the "acid-labile group" means a group having a leaving group which is detached by contacting with an acid resulting in forming a hydrophilic group such as a hydroxy or carboxy group. In the resin (A), the acid-labile group contained in the structural unit (a1) is preferably the following group (1) and/or group (2):

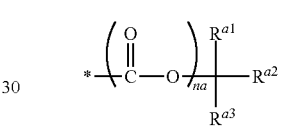

(1)

wherein $R^{a1}$ to $R^{a3}$ each independently represent a $C_1$ to $C_8$ alkyl group, a $C_3$ to $C_{20}$ alicyclic hydrocarbon group or a combination thereof, or $R^{a1}$ and $R^{a2}$ may be bonded together with a carbon atom bonded thereto to form a $C_3$ to $C_{20}$ divalent hydrocarbon group;

na represents an integer of 0 or 1; and

\* represents a binding site;

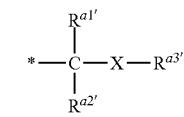

(2)

wherein $R^{a1'}$ and $R^{a2'}$ each independently represent a hydrogen atom or a $C_1$ to $C_{12}$ hydrocarbon group, $R^{a3'}$ represents a $C_1$ to $C_{20}$ hydrocarbon group, or $R^{a2'}$ and $R^{a3'}$ may be bonded together with a carbon atom and X bonded thereto to form a divalent $C_3$ to $C_{20}$ (or 4 to 21-membered) heterocyclic group, and a methylene group contained in the hydrocarbon group or the divalent heterocyclic group may be replaced by an oxygen atom or a sulfur atom;

X represents —O— or —S—; and

\* represents a binding site.

Examples of the alkyl group for $R^{a1}$ to $R^{a3}$ include methyl, ethyl, propyl, n-butyl, n-pentyl, n-hexyl, n-heptyl and n-octyl groups.

Examples of the alicyclic hydrocarbon group for $R^{a1}$ to $R^{a3}$ include monocyclic groups such as a cycloalkyl group, i.e., cyclopentyl, cyclohexyl, cycloheptyl, cyclooctyl groups; and polycyclic groups such as decahydronaphtyl, adamantyl and norbornyl groups as well as the following groups. In each of the formulae, \* represents a binding site.

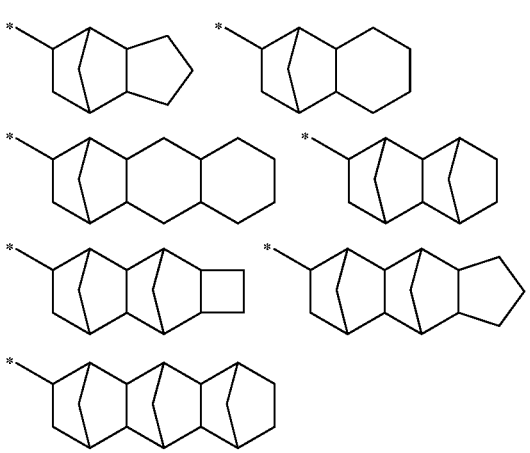

The carbon atoms of the alicyclic hydrocarbon group for $R^{a1}$ to $R^{a3}$ is preferably 3 to 16.

Examples of groups combining the alkyl group and the alicyclic hydrocarbon group include methyl cyclohexyl, dimethyl cyclohexyl, methyl norbornyl and methyl adamantly, cyclohexylmethyl, methyl cyclohexylmethyl, adamantylmethyl and norbornylmethyl groups.

na is preferably 0.

When $R^{a1}$ and $R^{a2}$ is bonded together to form a divalent hydrocarbon group, examples of the group —C($R^{a1}$)($R^{a2}$)($R^{a3}$) include the following groups. The carbon atoms of the divalent hydrocarbon group is preferably 3 to 12. In each of the formulae, * represent a binding site to —O—.

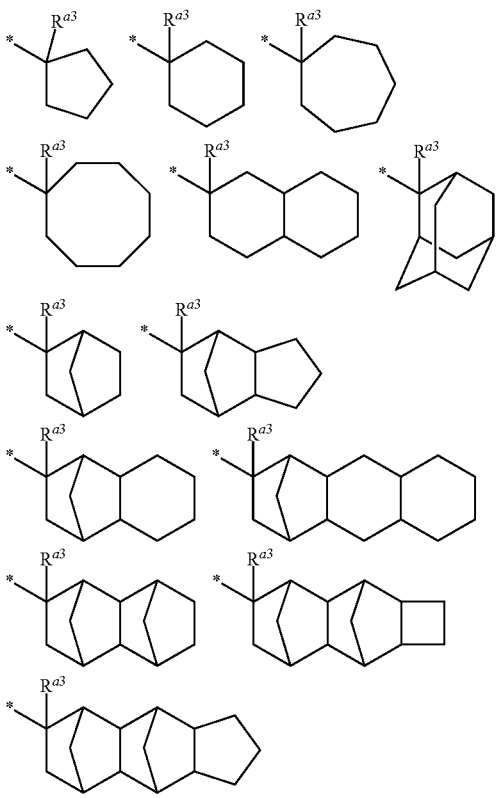

In each formula, $R^{a3}$ is as defined above.

Specific examples of the group represented by the formula (1) include, for example, 1,1-dialkylalkoxycarbonyl group (a group in which $R^{a1}$ to $R^{a3}$ are alkyl groups, preferably tert-butoxycarbonyl group, in the formula (1)), 2-alkyladamantane-2-yloxycarbonyl group (a group in which $R^{a1}$, $R^{a2}$ and a carbon atom form adamantyl group, and $R^{a3}$ is alkyl group, in the formula (1)), and 1-(adamantane-1-yl)-1-alkylalkoxycarbonyl group (a group in which $R^{a1}$ and $R^{a2}$ are alkyl group, and $R^{a3}$ is adamantyl group, in the formula (1)).

The hydrocarbon group for $R^{a1'}$ to $R^{a3'}$ includes any of an alkyl group, an alicyclic hydrocarbon group, an aromatic hydrocarbon group and a group formed by combining thereof.

Examples of the alkyl group and the alicyclic hydrocarbon group are the same examples as described above.

Examples of the aromatic hydrocarbon group include an aryl group such as phenyl, naphthyl, anthryl, p-methylphenyl, p-tert-butylphenyl, p-adamantylphenyl, tolyl, xylyl, cumenyl, mesityl, biphenyl, phenanthryl, 2,6-diethylphenyl and 2-methyl-6-ethylphenyl groups.

Examples of the divalent heterocyclic group formed by bonding with $R^{a2'}$ and $R^{a3'}$ with a carbon atom and X bonded thereto include the following groups.

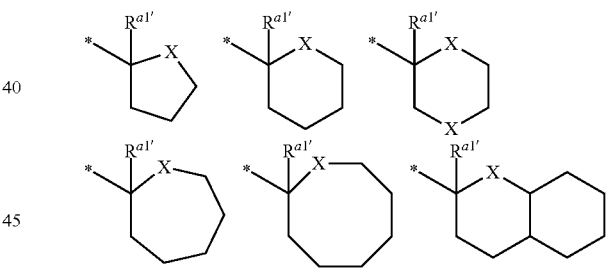

In each formula, $R^{a1'}$ and X are as defined above.

At least one of $R^{a1'}$ and $R^{a2'}$ is preferably a hydrogen atom.

Specific examples of the group represented by the formula (2) include the following groups. In each of the formulae, * represents a binding site.

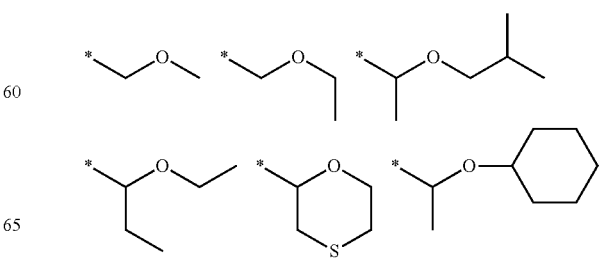

-continued

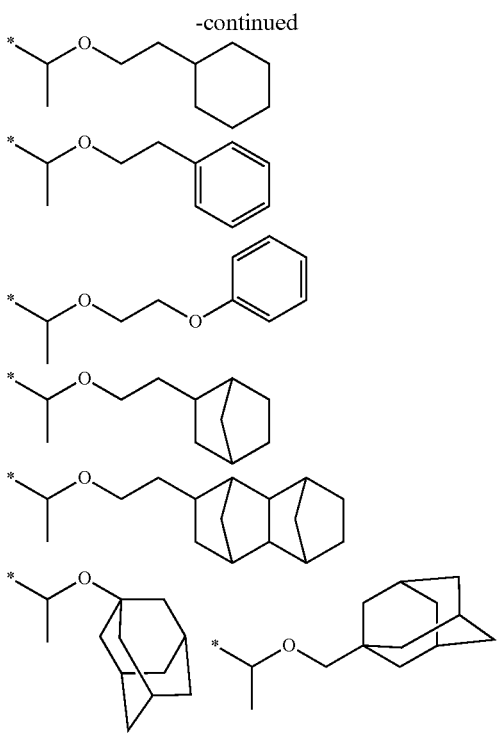

The monomer (a1) is preferably a monomer having an acid-labile group and an ethylenically unsaturated bond, and more preferably a (meth)acrylic monomer having an acid-labile group.

Among the (meth)acrylic monomer having an acid-labile group, a monomer having a $C_5$ to $C_{20}$ alicyclic hydrocarbon group is preferred. When a resin (A) has a structural unit derived from a monomer (a1) having a bulky structure such as the alicyclic hydrocarbon group is used for a resist composition, the resist composition having excellent resolution tends to be obtained.

Examples of a structural unit derived from the (meth) acrylic monomer having the group represented by the formula (1) preferably include structural units represented by formula (a1-0), formula (a1-1) and formula (a1-2) below. These may be used as a single structural unit or as a combination of two or more structural units. The structural unit represented by formula (a1-0), the structural unit represented by formula (a1-1) and a structural unit represented by formula (a1-2) are sometimes referred to as "structural unit (a1-0)", "structural unit (a1-1)" and "structural unit (a1-2)", respectively, and monomers inducing the structural unit (a1-0), the structural unit (a1-1) and the structural unit (a1-2) are sometimes referred to as "monomer (a1-0)", "monomer (a1-1)" and "monomer (a1-2)", respectively:

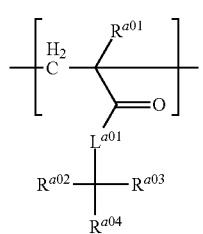

(a1-0)

wherein $L^{a01}$ represents —O— or *—O—$(CH_2)_{k01}$—CO—O—,
k01 represents an integer of 1 to 7,
* represents a binding site to —CO—,
$R^{a01}$ represents a hydrogen atom or a methyl group, and
$R^{a02}$, $R^{a03}$ and $R^{a04}$ each independently represent a $C_1$ to $C_8$ alkyl group, a $C_3$ to $C_{18}$ alicyclic hydrocarbon group or a combination thereof.

$L^{a01}$ is preferably an —O— or —O—$(CH_2)_{k01}$—CO—O— in which k01 is preferably an integer of 1 to 4, more preferably an integer of 1, more preferably an —O—.

Examples of the alkyl group and an alicyclic hydrocarbon group, and the combination thereof for $R^{a02}$, $R^{a03}$ and $R^{a04}$ are the same examples as the group described in $R^{a1}$ to $R^{a3}$ in the formula (1).

The alkyl group for $R^{a02}$, $R^{a03}$ and $R^{a04}$ is preferably a $C_1$ to $C_6$ alkyl group.

The alicyclic hydrocarbon group for $R^{a02}$, $R^{a03}$ and $R^{a04}$ is preferably a $C_3$ to $C_8$ alicyclic hydrocarbon group, more preferably a $C_3$ to $C_6$ alicyclic hydrocarbon group.

The group formed by combining the alkyl group and the alicyclic hydrocarbon group has preferably 18 or less of carbon atom. Examples of those groups include methylcyclohexyl, dimethylcyclohexyl, methylnorbornyl, methyladamantyl, cyclohexylmethyl, methylcyclohexyl methyladamantylmethyl, adamantylmethyl and norbornylmethyl groups.

$R^{a02}$ and $R^{a03}$ is preferably a $C_1$ to $C_6$ alkyl group, more preferably a methyl group or an ethyl group.

$R^{a04}$ is preferably a $C_1$ to $C_6$ alkyl group or a $C_5$ to $C_{12}$ alicyclic hydrocarbon group, more preferably methyl, ethyl, cyclohexyl or adamantyl group.

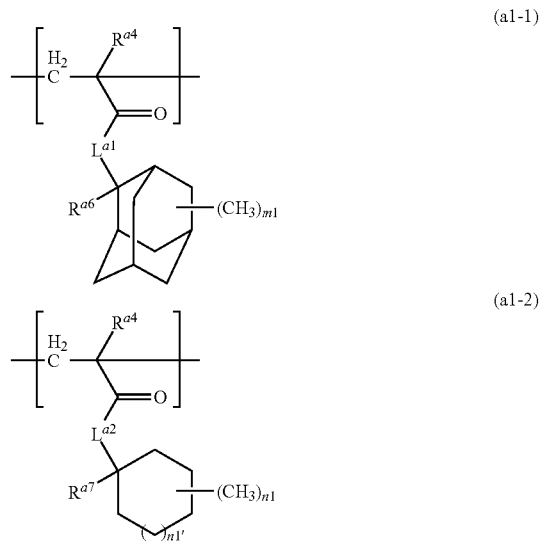

In each formula, $L^{a1}$ and $L^{a2}$ each independently represent —O— or *—O—$(CH_2)_{k1}$—CO—O—,
k1 represents an integer of 1 to 7,
* represents a binding site to —CO—,
$R^{a4}$ and $R^{a5}$ each independently represent a hydrogen atom or a methyl group,
$R^{a6}$ and $R^{a7}$ each independently represent a $C_1$ to $C_8$ alkyl group, a $C_3$ to $C_{18}$ alicyclic hydrocarbon group or a combination thereof,
m1 represents an integer of 0 to 14,
n1 represents an integer of 0 to 10, and
n1' represents an integer of 0 to 3.

$L^{a1}$ and $L^{a2}$ are preferably —O— or *—O—$(CH_2)_{k1'}$—CO—O— in which k1' represents an integer of 1 to 4 and more preferably 1, and still more preferably —O—.

$R^{a4}$ and $R^{a5}$ are preferably a methyl group.

Examples of the alkyl group and an alicyclic hydrocarbon group, and the combination thereof for $R^{a6}$ and $R^{a7}$ are the same examples as the group described in $R^{a1}$ to $R^{a3}$ in the formula (1).

The alkyl group for $R^{a6}$ and $R^{a7}$ is preferably a $C_1$ to $C_6$ alkyl group.

The alicyclic hydrocarbon group for $R^{a6}$ and $R^{a7}$ is preferably a $C_3$ to $C_8$ alicyclic hydrocarbon group, and more preferably a $C_3$ to $C_6$ alicyclic hydrocarbon group.

m1 is preferably an integer of 0 to 3, and more preferably 0 or 1.

n1 is preferably an integer of 0 to 3, and more preferably 0 or 1.

n1' is preferably 0 or 1.

Examples of the structural unit (a1-0) preferably include structural units represented by formula (a1-0-1) to formula (a1-0-12), and more preferably structural units represented by formula (a1-0-1) to formula (a1-0-10) below.

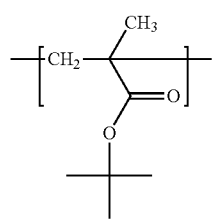
(a1-0-1)

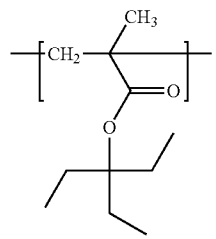
(a1-0-2)

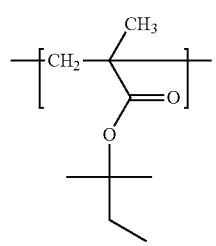
(a1-0-3)

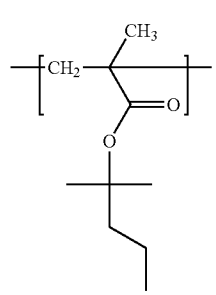
(a1-0-4)

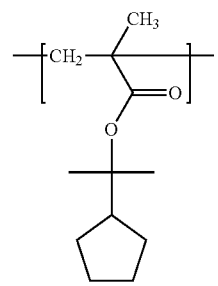
(a1-0-5)

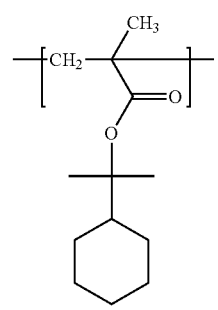
(a1-0-6)

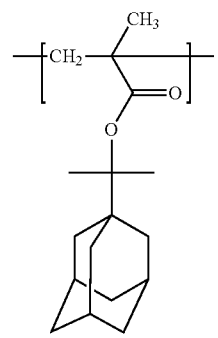
(a1-0-7)

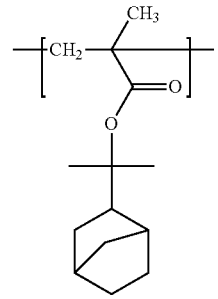
(a1-0-8)

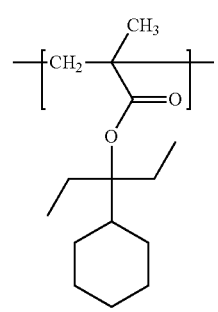
(a1-0-9)

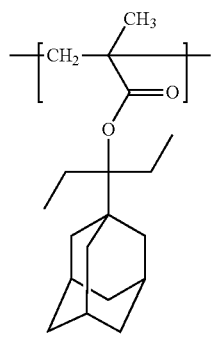
(a1-0-10)

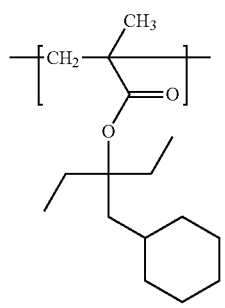
(a1-0-11)

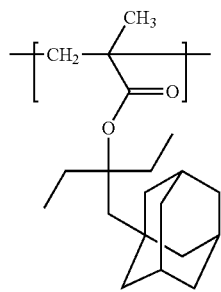
(a1-0-12)

Examples of the structural units (a1-0) include structural units in which a methyl group corresponding to $R^{a01}$ has been replaced by a hydrogen atom.

Examples of the monomer (a1-1) include monomers described in JP 2010-204646A. Among these, the monomers are preferably monomers represented by formula (a1-1-1) to formula (a1-1-8), and more preferably monomers represented by formula (a1-1-1) to formula (a1-1-4) below

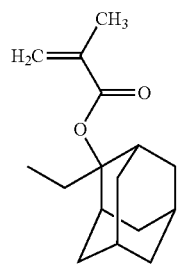
(a1-1-2)

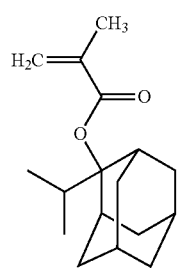
(a1-1-3)

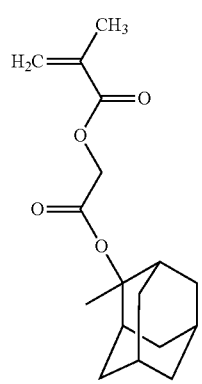
(a1-1-4)

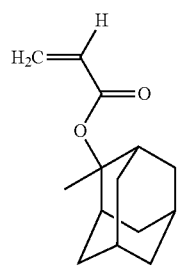
(a1-1-5)

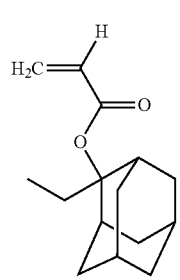
(a1-1-6)

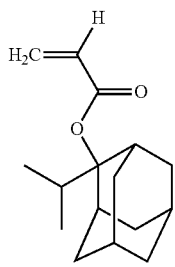
(a1-1-7)

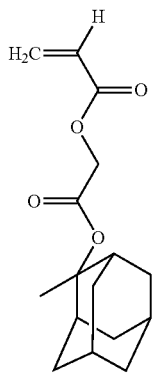
(a1-1-8)

Examples of the monomer (a1-2) include 1-methylcyclopentane-1-yl (meth)acrylate, 1-ethylcyclopentane-1-yl (meth)acrylate, 1-methylcyclohexane-1-yl (meth)acrylate, 1-ethylcyclohexane-1-yl (meth)acrylate, 1-ethylcycloheptane-1-yl (meth)acrylate, 1-ethylcyclooctane-1-yl (meth)acrylate, 1-isopropylcyclopentane-1-yl (meth)acrylate and 1-isopropylcyclohexane-1-yl (meth)acrylate. Among these, the monomers are preferably monomers represented by formula (a1-2-1) to formula (a1-2-12), and more preferably monomers represented by formula (a1-2-3), formula (a1-2-4), formula (a1-2-9) and formula (a1-2-10), and still more preferably monomer represented by formula (a1-2-3) and formula (a1-2-9) below.

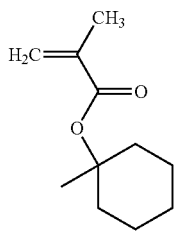
(a1-2-1)

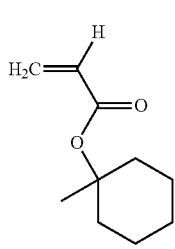
(a1-2-2)

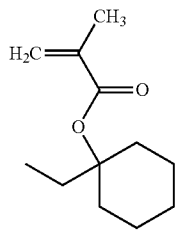
(a1-2-3)

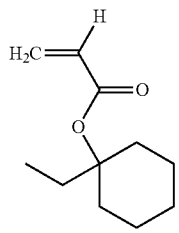
(a1-2-4)

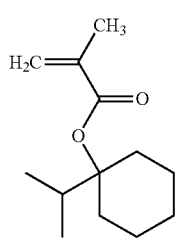
(a1-2-5)

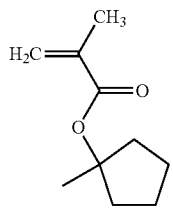
(a1-2-6)

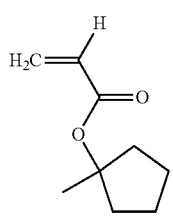
(a1-2-7)

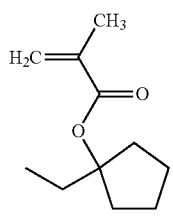
(a1-2-8)

(a1-2-9)

(a1-2-10)
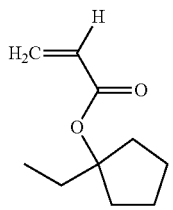

(a1-2-11)
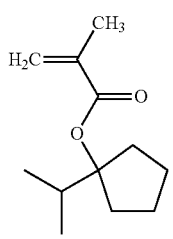

(a1-2-12)
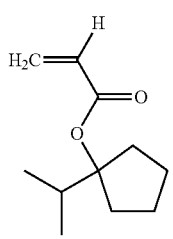

When the resin (A) has the structural unit (a1-0) and/or the structural unit (a1-1) and/or the structural unit (a1-2), the total proportion thereof is generally 10 to 95% by mole, preferably 15 to 90% by mole, and more preferably 20 to 85% by mole, with respect to the total structural units (100% by mole) of the resin (A).

Further, examples of the structural unit (a1) having the group (1) include a structural unit presented by formula (a1-3). The structural unit represented by formula (a1-3) is sometimes referred to as "structural unit (a1-3)". The monomer from which the structural unit (a1-3) is derived is sometimes referred to as "monomer (a1-3)".

(a1-3)
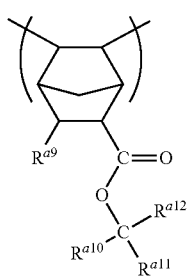

In the formula, $R^{a9}$ represents a carboxy group, a cyano group, a —COOR$^{a13}$, a hydrogen atom or a $C_1$ to $C_3$ aliphatic hydrocarbon group that may have a hydroxy group,
$R^{a13}$ represents a $C_1$ to $C_8$ aliphatic hydrocarbon group, a $C_3$ to $C_{20}$ alicyclic hydrocarbon group or a group formed by combining thereof, a hydrogen atom contained in the aliphatic hydrocarbon group and the alicyclic hydrocarbon group may be replaced by a hydroxy group, a methylene group contained in the aliphatic hydrocarbon group and the alicyclic hydrocarbon group may be replaced by an oxygen atom or a carbonyl group, $R^{a10}$, $R^{a11}$ and $R^{a12}$ each independently represent a $C_1$ to $C_8$ alkyl group, a $C_3$ to $C_{20}$ alicyclic hydrocarbon group or a group formed by combining thereof, or $R^{a10}$ and $R^{a11}$ may be bonded together with a carbon atom bonded thereto to form a $C_2$ to $C_{20}$ divalent hydrocarbon group.

Here, examples of —COOR$^{a13}$ group include a group in which a carbonyl group is bonded to the alkoxy group, such as methoxycarbonyl and ethoxycarbonyl groups.

Examples of the aliphatic hydrocarbon group that may have a hydroxy group for $R^{a9}$ include methyl, ethyl, propyl, hydroxymethy and 2-hydroxyethyl groups.

Examples of the $C_1$ to $C_8$ aliphatic hydrocarbon group for $R^{a13}$ include methyl, ethyl, propyl, isopropyl, n-butyl, sec-butyl, tert-butyl, n-pentyl, n-hexyl, n-heptyl, 2-ethylhexyl and n-octyl groups.

Examples of the $C_3$ to $C_{20}$ alicyclic hydrocarbon group for $R^{a13}$ include cyclopentyl, cyclopropyl, adamantyl, adamantylmetyl, 1-(adamantyl-1-yl)-methylethyl, 2-oxo-oxolane-3-yl, 2-oxo-oxolane-4-yl groups.

Examples of the alkyl group for $R^{a10}$ to $R^{a12}$ include methyl, ethyl, n-propyl, isopropyl, n-butyl, sec-butyl, tert-butyl, n-pentyl, n-hexyl, n-heptyl, 2-ethylhexyl and n-octyl groups.

Examples of the alicyclic hydrocarbon group for $R^{a10}$ and $R^{a12}$ include monocyclic groups such as a cycloalkyl group, i.e., cyclopropyl, cyclobutyl, cyclopentyl, cyclohexyl, methylcyclohexyl, dimethylcyclohexyl, cycloheptyl, cyclooctyl and cyclodecyl groups; and polycyclic groups such as decahydronaphtyl, adamantyl, 2-alkyl-2-adamantyl, 1-(adamantane-1-yl) alkane-1-yl, norbornyl, methyl norbornyl and isobornyl groups.

When $R^{a10}$ and $R^{a11}$ are bonded together with a carbon atom bonded thereto to form a divalent hydrocarbon group, examples of the group-C($R^{a10}$)($R^{a11}$)($R^{a12}$) include the following groups.

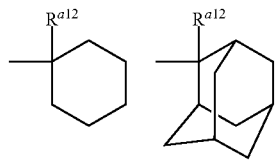

In each formula, $R^{a12}$ is as defined above.

Examples of the monomer (a1-3) include tert-butyl 5-norbornene-2-carboxylate, 1-cyclohexyl-1-methylethyl 5-norbornene-2-carboxylate, 1-methylcyclohexyl 5-norbornene-2-carboxylate, 2-methy-2-adamantane-2-yl 5-norbornene-2-carboxylate, 2-ethyl-2-adamantane-2-yl 5-norbornene-2-carboxylate, 1-(4-methycyclohexyl)-1-methylethyl 5-norbornene-2-carboxylate, 1-(4-hydroxycyclohexyl)-1-methylethyl 5-norbornene-2-carboxylate, 1-methyl-(4-oxocyclohexyl)-1-ethyl 5-norbornene-2-carboxylate, and 1-(1-adamantane-1-yl)-1-methylethyl 5-norbornene-2-carboxylate.

The resin (A) has the structural unit (a1-3) can improve the resolution of the obtained resist composition because it has a bulky structure, and also can improve a dry-etching tolerance of the obtained resist composition because of incorporated a rigid norbornene ring into a main chain of the resin (A).

When the resin (A) has the structural unit (a1-3), the proportion thereof is preferably 10% by mole to 95% by mole, more preferably 15% by mole to 90% by mole, and still more preferably 20% by mole to 85% by mole, with respect to the total structural units constituting the resin (A) (100% by mole).

Examples of a structural unit (a1) having the group (2) include a structural unit represented by formula (a1-4). The structural unit is sometimes referred to as "structural unit (a1-4)".

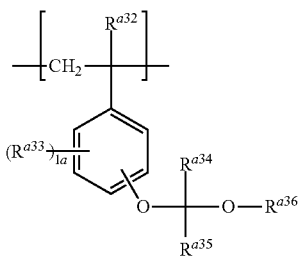

(a1-4)

In the formula, $R^{a32}$ represents a hydrogen atom, a halogen atom or a $C_1$ to $C_6$ alkyl group that may have a halogen atom, $R^{a33}$ in each occurrence independently represent a halogen atom, a hydroxy group, a $C_1$ to $C_6$ alkyl group, a $C_1$ to $C_6$ alkoxy group, a $C_2$ to $C_4$ acyl group, a $C_2$ to $C_4$ acyloxy group, an acryloyloxy group or methacryloyloxy group, la represents an integer 0 to 4, $R^{a34}$ and $R^{a35}$ each independently represent a hydrogen atom or a $C_1$ to $C_{12}$ hydrocarbon group; and $R^{a36}$ represents a $C_1$ to $C_{20}$ hydrocarbon group, or $R^{a35}$ and $R^{a36}$ may be bonded together with a C—O bonded thereto to form a divalent $C_3$ to $C_{20}$ heterocyclic group, and a methylene group contained in the hydrocarbon group or the divalent heterocyclic group may be replaced by an oxygen atom or a sulfur atom.

Examples of the alkyl group for $R^{a32}$ and $R^{a33}$ include methyl, ethyl, propyl, isopropyl, butyl, pentyl and hexyl groups. The alkyl group is preferably a $C_1$ to $C_4$ alkyl group, and more preferably a methyl group or an ethyl group, and still more preferably a methyl group.

Examples of the halogen atom for $R^{a32}$ and $R^{a33}$ include a fluorine, chlorine, bromine and iodine atoms.

Examples of the alkyl group that may have a halogen atom include trifluoromethyl, difluoromethyl, methyl, perfluoroethyl, 1,1,1-trifluoroethyl, 1,1,2,2-tetrafluoroethyl, ethyl, perfluoropropyl, 1,1,1,2,2-pentafluoropropyl, propyl, perfluorobutyl, 1,1,2,2,3,3,4,4-octafluorobutyl, butyl, perfluoropentyl, 1,1,1,2,2,3,3,4,4-nonafluoropentyl, n-pentyl, n-hexyl and n-perfluorohexyl groups.

Examples of an alkoxy group include methoxy, ethoxy, propoxy, butoxy, pentyloxy and hexyloxy groups. The alkoxy group is preferably a $C_1$ to $C_4$ alkoxy group, more preferably a methoxy group or an ethoxy group, and still more preferably methoxy group.

Examples of the acyl group include acetyl, propionyl and butyryl groups.

Examples of the acyloxy group include acetyloxy, propionyloxy and butyryloxy groups.

Examples of the hydrocarbon group for $R^{a34}$ and $R^{a35}$ are the same examples as described in $R^{a1'}$ to $R^{a2'}$ in the formula (2).

Examples of hydrocarbon group for $R^{a36}$ include a $C_1$ to $C_{18}$ alkyl group, a $C_3$ to $C_{18}$ alicyclic hydrocarbon group, a $C_6$ to $C_{18}$ aromatic hydrocarbon group or a group formed by combining thereof.

In the formula (a1-4), $R^{a32}$ is preferably a hydrogen atom.

$R^{a33}$ is preferably a $C_1$ to $C_4$ alkoxy group, more preferably a methoxy group or an ethoxy group, and still more preferably a methoxy group.

la is preferably 0 or 1, and more preferably 0.

$R^{a34}$ is preferably a hydrogen atom.

$R^{a35}$ is preferably a $C_1$ to $C_{12}$ hydrocarbon group, and more preferably a methyl group or an ethyl group.

The hydrocarbon group for $R^{a36}$ is preferably a $C_1$ to $C_{18}$ alkyl group, a $C_3$ to $C_{18}$ alicyclic hydrocarbon group, a $C_6$ to $C_{18}$ aromatic hydrocarbon group or a combination thereof, and more preferably a $C_1$ to $C_{18}$ alkyl group, a $C_3$ to $C_{18}$ alicyclic hydrocarbon group or a $C_7$ to $C_{18}$ aralkyl group. The alkyl group and the alicyclic hydrocarbon group for $R^{a36}$ are preferably unsubstituted. When the aromatic hydrocarbon group for $R^{a36}$ has a substituent, the substituent is preferably a $C_6$ to $C_{10}$ aryloxy group.

Examples of the monomer from which the structural unit (a1-4) is derived include monomers described in JP 2010-204646A. Among these, the monomers are preferably the following monomers represented by formula (a1-4-1) to formula (a1-4-8), and more preferably monomers represented by formula (a1-4-1) to formula (a1-4-5).

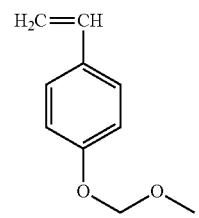

(a1-4-1)

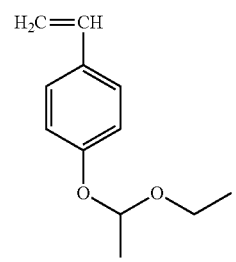

(a1-4-2)

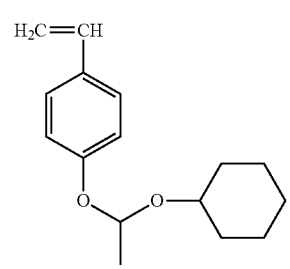

(a1-4-3)

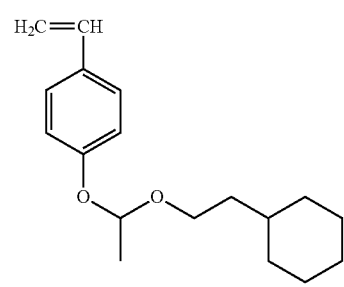

(a1-4-4)

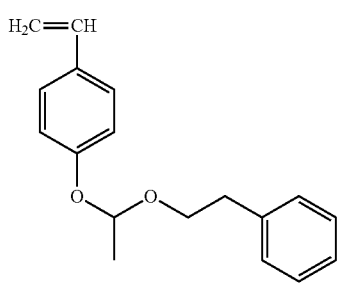

(a1-4-5)

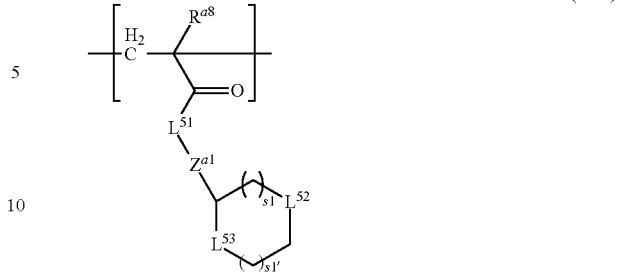

(a1-5)

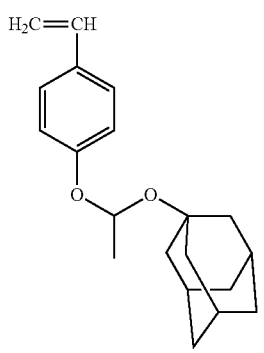

(a1-4-6)

In the formula (a1-5), $R^{a8}$ represents a hydrogen atom, a halogen atom or a $C_1$ to $C_6$ alkyl group that may have a halogen atom, $Z^{a1}$ represent a single bond or *—$(CH_2)_{h3}$—CO-$L^{54}$-, h3 represents an integer of 1 to 4,

* represents a binding site to $L^{51}$, $L^{51}$, $L^{52}$, $L^{53}$ and $L^{54}$ each independently represent —O— or —S—, s1 represents an integer of 1 to 3, and s1' represents an integer of 0 to 3.

In the formula (a1-5), $R^{a8}$ is preferably a hydrogen atom, a methyl group or a trifluoromethyl group;

$L^{51}$ is preferably —O—;

$L^{52}$ and $L^{53}$ are independently preferably —O— or —S—, and more preferably one is —O— and another is —S—.

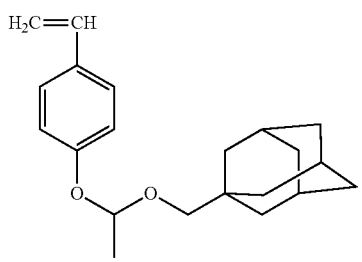

(a1-4-7)

s1 is preferably 1;

s1' is preferably an integer of 0 to 2;

$Z^{a1}$ is preferably a single bond or *—$CH_2$—CO—O—. * represents a binding site to $L^{51}$.

Examples of a monomer from which the structural unit (a1-5) is derived include a monomer described in JP 2010-61117A. Among these, the monomers are preferably monomers represented by formula (a1-5-1) to formula (a1-5-4), and more preferably monomers represented by formula (a1-5-1) to formula (a1-5-2) below.

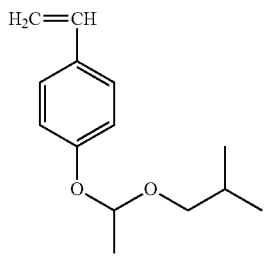

(a1-4-8)

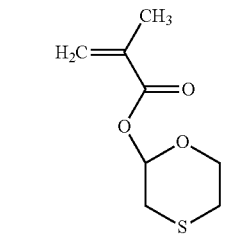

(a1-5-1)

When the resin (A) has the structural unit (a1-4), the proportion thereof is preferably 10% by mole to 95% by mole, more preferably 15% by mole to 90% by mole, and still more preferably 20% by mole to 85% by mole, with respect to the total structural units constituting the resin (A) (100% by mole).

Examples of the structural unit having an acid-labile group include a structural unit represented by formula (a1-5). The structural unit is sometimes referred to as "structural unit (a1-5)".

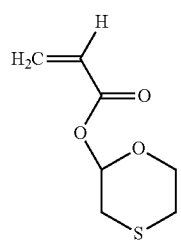

(a1-5-2)

-continued

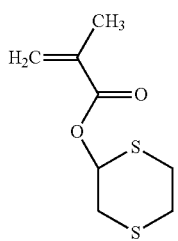

(a1-5-3)

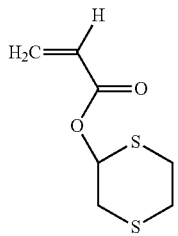

(a1-5-4)

When the resin (A) has the structural unit (a1-5), the proportion thereof is preferably 1% by mole to 50% by mole, more preferably 3% by mole to 45% by mole, and still more preferably 5% by mole to 40% by mole, with respect to the total structural units (100% by mole) constituting the resin (A).

The resin (A) has, as the structural unit (a1), preferably at least one, more preferably two or more structural units selected from the structural unit (a1-0), the structural unit (a1-1), the structural unit (a1-2) and the structural unit (a1-5), a combination of the structural unit (a1-1) and the structural unit (a1-2), a combination of the structural unit (a1-1) and the structural unit (a1-5), a combination of the structural unit (a1-1) and the structural unit (a1-0), a combination of the structural unit (a1-2) and the structural unit (a1-0), a combination of the structural unit (a1-5) and the structural unit (a1-0), a combination of the structural unit (a1-0), the structural unit (a1-1) and the structural unit (a1-2), a combination of the structural unit (a1-0), the structural unit (a1-1) and the structural unit (a1-5), and further still preferably a combination of the structural unit (a1-1) and the structural unit (a1-2), a combination of the structural unit (a1-1) and the structural unit (a1-5). The structural unit (a1) has preferably the structural unit (a1-1).

<Structural Unit (s)>

The structural unit (s) is derived from a monomer having no acid-labile group (which monomer is sometimes referred to as "monomer (s)").

As the monomer (s) from which the structural unit (s) is derived, a known monomer having no acid-labile group can be used.

As the structural unit (s), a structural unit having a hydroxy group or a lactone ring but having no acid-labile group is preferred. When a resin has the structural unit derived from a structural unit having a hydroxy group but having no acid-labile group (such structural unit is sometimes referred to as "structural unit (a2)") and/or a structural unit having a lactone ring but having no acid-labile group (such structural unit is sometimes referred to as "structural unit (a3)") is used, the adhesiveness of resist to a substrate and resolution of resist pattern tend to be improved.

<Structural Unit (a2)>

The structural unit (a2) having a hydroxy group may be an alcoholic hydroxy group or a phenolic hydroxy group.

When KrF excimer laser lithography (248 nm), or high-energy irradiation such as electron beam or EUV (extreme ultraviolet) is used for the resist composition, using the structural unit having a phenolic hydroxy group as the structural unit (a2) is preferred.

When ArF excimer laser lithography (193 nm) is used, using the structural unit having an alcoholic hydroxy group as the structural unit (a2) is preferred, and using the structural unit represented by formula (a2-1) is more preferred.

The structural unit (a2) may be used as a single structural unit or as a combination of two or more structural units.

When the resin (A) has the structural units (a2) having the hydroxy group, the total proportion thereof is preferably 5% by mole to 95% by mole, more preferably 10% by mole to 80% by mole, and still more preferably 15% by mole to 80% by mole, with respect to the total structural units (100% by mole) constituting the resin (A).

Examples of the structural unit (a2) having a phenolic hydroxy group include a structural unit represented by formula (a2-0) (which is sometimes referred to as "structural unit (a2-0)").

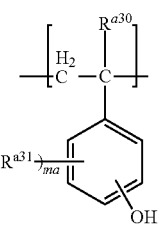

(a2-0)

In the formula (a2-0), $R^{a30}$ represents a hydrogen atom, a halogen atom or a $C_1$ to $C_6$ alkyl group that may have a halogen atom, $R^{a31}$ in each occurrence independently represents a halogen atom, a hydroxy group, a $C_1$ to $C_6$ alkyl group, a $C_1$ to $C_6$ alkoxy group, a $C_2$ to $C_4$ acyl group, a $C_2$ to $C_4$ acyloxy group, an acryloyloxy group or methacryloyloxy group, and ma represents an integer 0 to 4.

Examples of the alkyl group include methyl, ethyl, propyl, butyl, n-pentyl and n-hexyl groups.

Examples of the halogen atom include a chlorine atom, a fluorine atom and bromine atom.

Examples of the $C_1$ to $C_6$ alkyl group that may have a halogen atom for $R^{a30}$ include trifluoromethyl, difluoromethyl, methyl, perfluoromethyl, 1,1,1-trifluoroethyl, 1,1,2,2-tetrafluoroethyl, ethyl, perfluoropropyl, 1,1,1,2,2-pentafluoropropyl, propyl, perfluorobutyl, 1,1,2,2,3,3,4,4-octafluorobutyl, butyl, perfluoropentyl, 1,1,1,2,2,3,3,4,4-nonafluoropentyl, n-pentyl, n-hexyl and n-perfluorohexyl groups.

$R^{a30}$ is preferably a hydrogen atom or a $C_1$ to $C_4$ alkyl group, and more preferably a hydrogen atom, a methyl group or an ethyl group, and still more preferably a hydrogen atom or a methyl group.

Examples of the alkoxy group for $R^{a31}$ include methoxy, ethoxy, propoxy, butoxy, pentyloxy, and hexyloxy groups. $R^{a31}$ is preferably a $C_1$ to $C_4$ alkoxy group, more preferably a methoxy group or an ethoxy group, and still more preferably a methoxy group.

Examples of the acyl group include acetyl, propionyl and butyryl groups.

Examples of the acyloxy group include acetyloxy, propionyloxy and butyryloxy groups.

ma is preferably 0, 1 or 2, more preferably 0 or 1, still more preferably 0.

Examples of a monomer from which the structural unit (a2-0) is derived include monomers described in JP2010-204634A.

The structural unit (a2-0) having a phenolic hydroxy group is preferably a structural unit represented below.

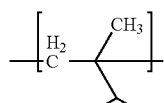
(a2-0-1)

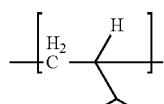
(a2-0-2)

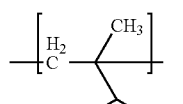
(a2-0-3)

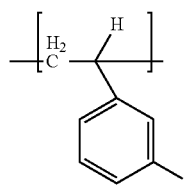
(a2-0-4)

Among these, a structural unit represented by formula (a2-0-1) and formula (a2-0-2) are preferred.

The resin (A) which has the structural units (a2-0) having a phenolic hydroxy group can be produced, for example, by polymerizing a monomer where its phenolic hydroxy group has been protected with a suitable protecting group, followed by deprotection. The deprotection is carried in such a manner that an acid-labile group in the structural unit (a1) is significantly impaired. Examples of the protecting group for a phenolic hydroxy group include an acetyl group.

When the resin (A) has the structural unit (a2-0) having the phenolic hydroxy group, the proportion thereof is preferably 5% by mole to 95% by mole, more preferably 10% by mole to 80% by mole, and still more preferably 15% by mole to 80% by mole, with respect to the total structural units (100% by mole) constituting the resin (A).

Examples of the structural unit (a2) having an alcoholic hydroxy group include the structural unit represented by formula (a2-1) (which is sometimes referred to as "structural unit (a2-1)").

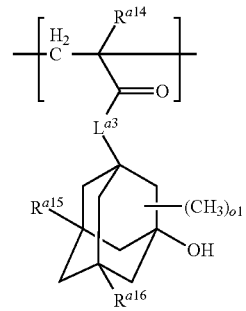
(a2-1)

In the formula (a2-1), $L^{a3}$ represents —O— or *—O—$(CH_2)_{k2}$—CO—O—, k2 represents an integer of 1 to 7,

* represents a binding site to —CO—, $R^{a14}$ represents a hydrogen atom or a methyl group, $R^{a15}$ and $R^{a16}$ each independently represent a hydrogen atom, a methyl group or a hydroxy group, and o1 represents an integer of 0 to 10.

In the formula (a2-1), $L^{a3}$ is preferably —O—, —O—$(CH_2)_{f1}$—CO—O—, here f1 represents an integer of 1 to 4, and more preferably —O—.

$R^{a14}$ is preferably a methyl group.

$R^{a15}$ is preferably a hydrogen atom.

$R^{a16}$ is preferably a hydrogen atom or a hydroxy group.

o1 is preferably an integer of 0 to 3, and more preferably an integer of 0 or 1.

Examples of the monomer from which the structural unit (a2-1) is derived include monomers described in JP 2010-204646A. Among these, the structural units (a2-1) are preferably structural units represented by formula (a2-1-1) to formula (a2-1-6), more preferably structural units represented by formula (a2-1-1) to formula (a2-1-4), and still more preferably structural units represented by formula (a2-1-1) and formula (a2-1-3).

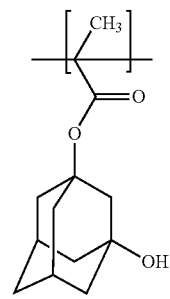
(a2-1-1)

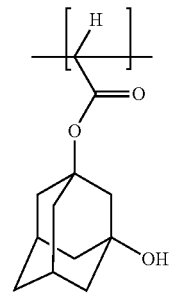
(a2-1-2)

-continued

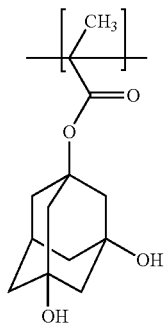
(a2-1-3)

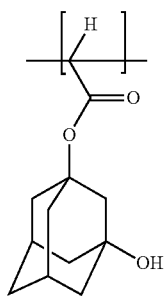
(a2-1-4)

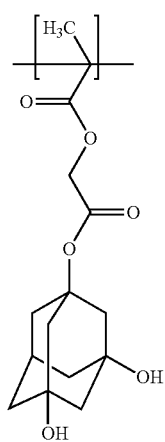
(a2-1-5)

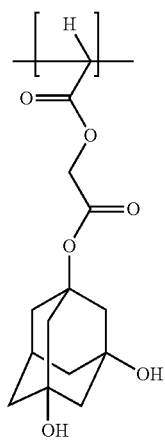
(a2-1-6)

When the resin (A) has the structural unit (a2-1) having an alcoholic hydroxy group, the proportion thereof is generally 1% by mole to 45% by mole, preferably 1% by mole to 40% by mole, more preferably 1% by mole to 35% by mole, and still more preferably 2% by mole to 20% by mole, with respect to the total structural units (100% by mole) constituting the resin (A).

<Structural Unit (a3)>

The lactone ring included in the structural unit (a3) may be a monocyclic ring such as β-propiolactone, γ-butyrolactone, δ-valerolactone, or a condensed ring of monocyclic lactone ring with another ring. Examples of the lactone ring preferably include γ-butyrolactone, amadantane lactone, or bridged ring with γ-butyrolactone.

Examples of the structural unit (a3) include structural units represented by any of formula (a3-1), formula (a3-2), formula (a3-3) and formula (a3-4). These structural units may be used as a single unit or as a combination of two or more units.

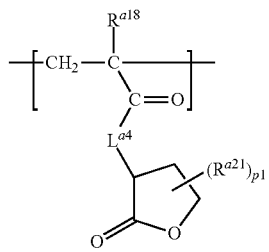
(a3-1)

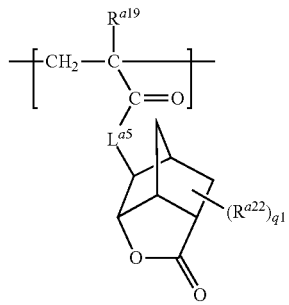
(a3-2)

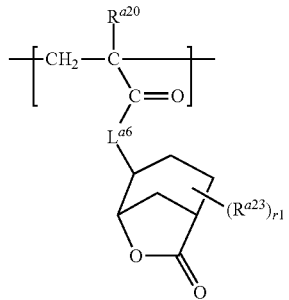
(a3-3)

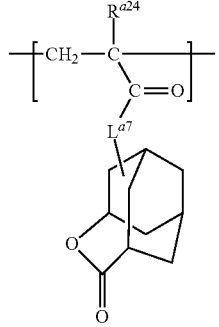
(a3-4)

In each formula, $L^{a4}$ represents *—O— or *—O—$(CH_2)_{k3}$—CO—O—, k3 represents an integer of 1 to 7, * represents a binding site to a carbonyl group, $R^{a18}$ represents a hydrogen atom or a methyl group, $R^{a21}$ in each occurrence represents a $C_1$ to $C_4$ aliphatic hydrocarbon group, and p1 represents an integer of 0 to 5, $L^{a5}$ represents *—O— or *—O—$(CH_2)_{k3}$—CO—O—, k3 represents an integer of 1 to 7, * represents a binding site to a carbonyl group, $R^{a19}$ represents a hydrogen atom or a methyl group, $R^{a22}$ in each occurrence represents a carboxy group, a cyano group or a $C_1$ to $C_4$ aliphatic hydrocarbon group, q1 represents an integer of 0 to 3, $L^{a6}$ represents *—O— or *—O—$(CH_2)_{k3}$—CO—O—, k3 represents an integer of 1 to 7, * represents a binding site to a carbonyl group, $R^{a20}$ represents a hydrogen atom or a methyl group, $R^{a23}$ in each occurrence represents a carboxy group, a cyano group or a $C_1$ to $C_4$ aliphatic hydrocarbon group, and r1 represents an integer of 0 to 3, $R^{a24}$ represents a hydrogen atom, a halogen atom or a $C_1$ to $C_6$ alkyl group that may have a halogen atom, $L^{a7}$ represents a single bond, *-$L^{a8}$-O—, *-$L^{a8}$-CO—O—, *-$L^{a8}$-CO—O-$L^{a9}$-CO—O—, or *-$L^{a8}$-O—CO-$L^{a9}$-O—; * represents a binding site to a carbonyl group, and $L^{a8}$ and $L^{a9}$ each independently represent a $C_1$ to $C_6$ alkanediyl group.

Examples of the aliphatic hydrocarbon group for $R^{a21}$, $R^{a22}$ and $R^{a23}$ include an alkyl group such as methyl, ethyl, n-propyl, isopropyl, n-butyl, sec-butyl and tert-butyl groups.

Examples of the halogen atom for $R^{a24}$ include fluorine, chlorine, bromine and iodine atoms;

Examples of the alkyl group for $R^{a24}$ include methyl, ethyl, n-propyl, isopropyl, n-butyl, sec-butyl, tert-butyl, n-pentyl and n-hexyl groups. The alkyl group is preferably a $C_1$ to $C_4$ alkyl group, more preferably a methyl group or an ethyl group.

Examples of the alkyl group having a halogen atom for $R^{a24}$ include trifluoromethyl, perfluoroethyl, perfluoropropyl, perfluoro-isopropyl, perfluorobutyl, perfluoro-sec-butyl, perfluoro-tert-butyl, perfluoropentyl, perfluorohexyl, trichloromethyl, tribromomethyl and triiodomethyl groups.

Examples of the alkanediyl group for $L^{a8}$ and $L^{a9}$ include methylene, ethylene, propane-1,3-diyl, propane-1,2-diyl, butane-1,4-diyl, pentane-1,5-diyl, hexane-1,6-diyl, butane-1,3-diyl, 2-methylpropane-1,3-diyl, 2-methylpropane-1,2-diyl, pentane-1,4-diyl and 2-methylbutane-1,4-diyl groups.

In the formulae (a3-1) to (a3-3), $L^{a4}$ to $L^{a6}$ is independently preferably —O—, *—O—$(CH_2)_{k3'}$—CO—O—, here k3' represents an integer of 1 to 4, more preferably —O— or *—O—$CH_2$—CO—O—, and still more preferably *—O—.

$R^{a18}$ to $R^{a21}$ is preferably a methyl group.

$R^{a22}$ and $R^{a23}$ are each independently preferably a carboxy group, a cyano group or a methyl group.

p1, q1 and r1 are independently preferably an integer of 0 to 2, and more preferably 0 or 1.

In the formula (a3-4), $R^{a24}$ is preferably a hydrogen atom or a $C_1$ to $C_4$ alkyl group, more preferably a hydrogen atom, a methyl group or an ethyl group, and still more preferably a hydrogen atom or a methyl group.

$L^{a7}$ is preferably a single bond or *-$L^{a8}$-CO—O—, and more preferably a single bond, —$CH_2$—CO—O— or —$C_2H_4$—CO—O—.

Examples of the monomer from which the structural unit (a3) is derived include monomers described in JP 2010-204646A, monomers described in JP2000-122294A and monomers described in JP2012-41274A. The structural units (a3) are preferably structural units represented by formula (a3-1-1) to formula (a3-1-4), formula (a3-2-1) to formula (a3-2-4), formula (a3-3-1) to formula (a3-3-4), formula (a3-4-1) to formula (a3-4-12), more preferably structural units represented by formula (a3-1-1), formula (a3-1-2), formula (a3-2-3), formula (a3-2-4), formula (a3-4-1) to formula (a3-4-12), still more preferably structural units represented by formula (a3-4-1) to formula (a3-4-12), further still preferably formula (a3-4-1) to formula (a3-4-6) below.

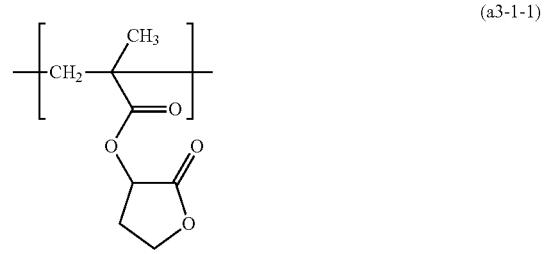

(a3-1-1)

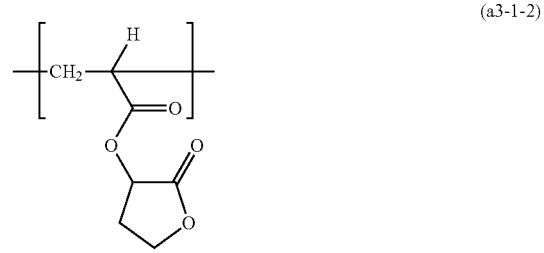

(a3-1-2)

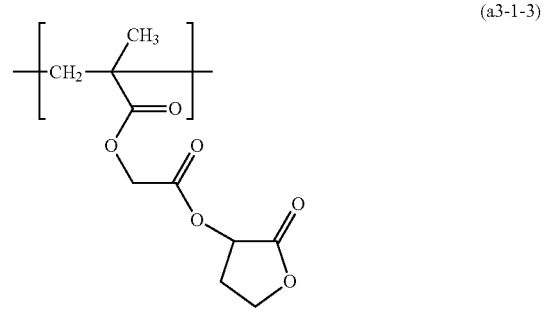

(a3-1-3)

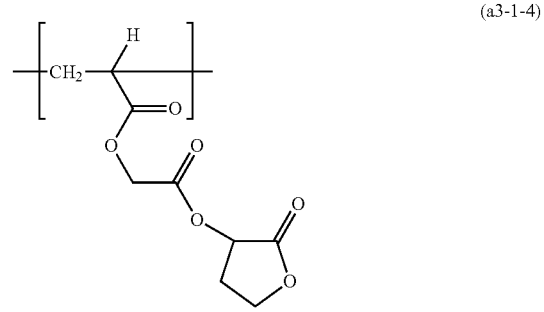

(a3-1-4)

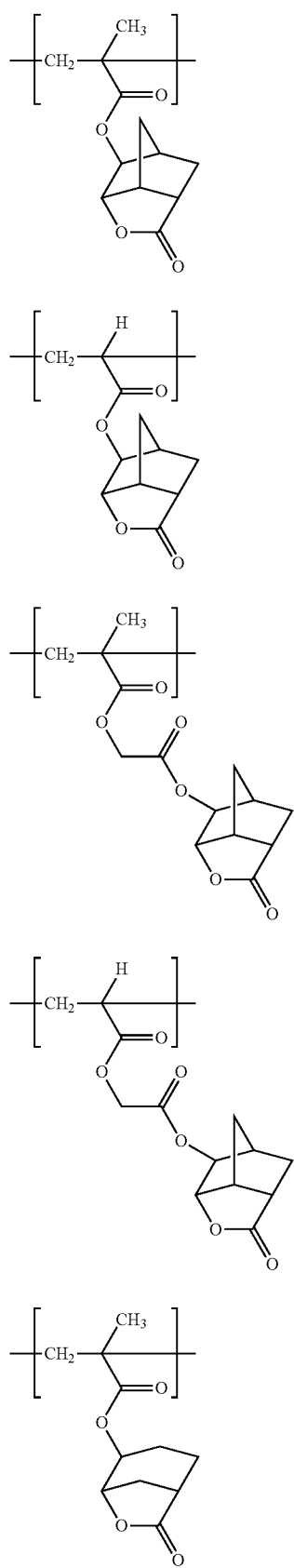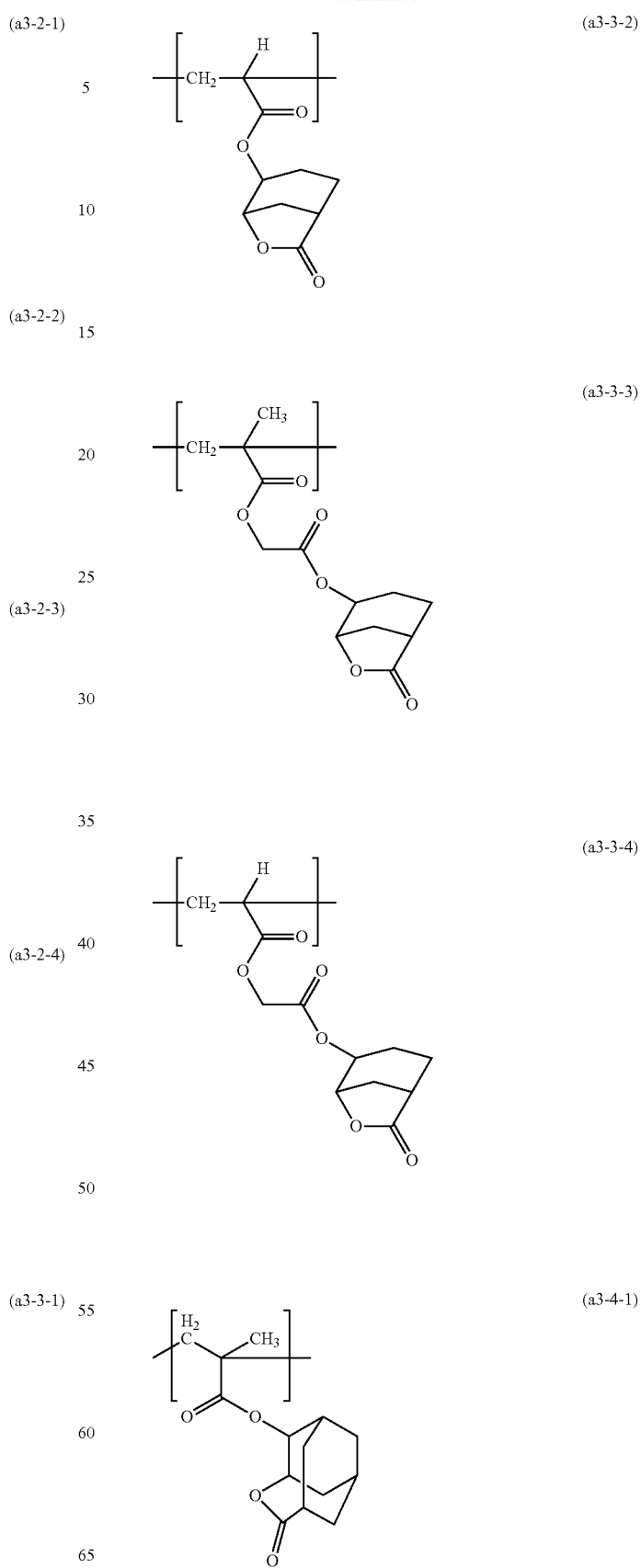

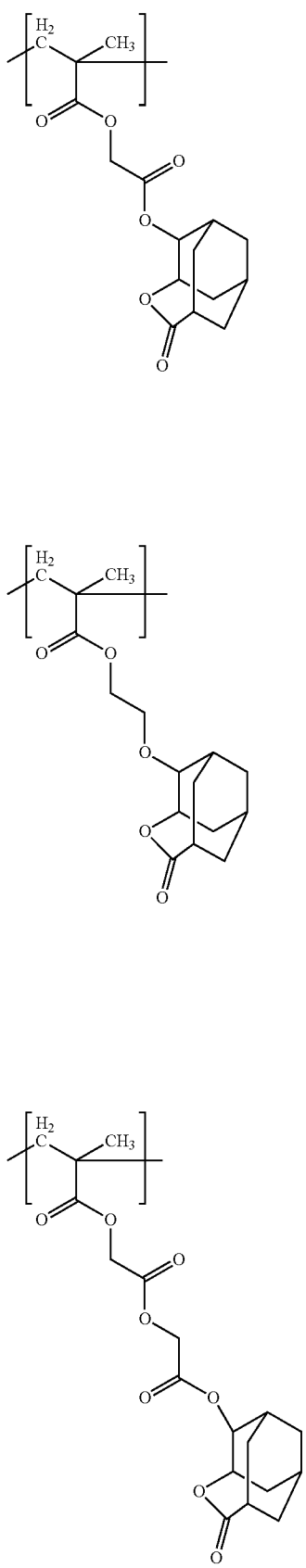
(a3-4-2)
(a3-4-3)
(a3-4-4)
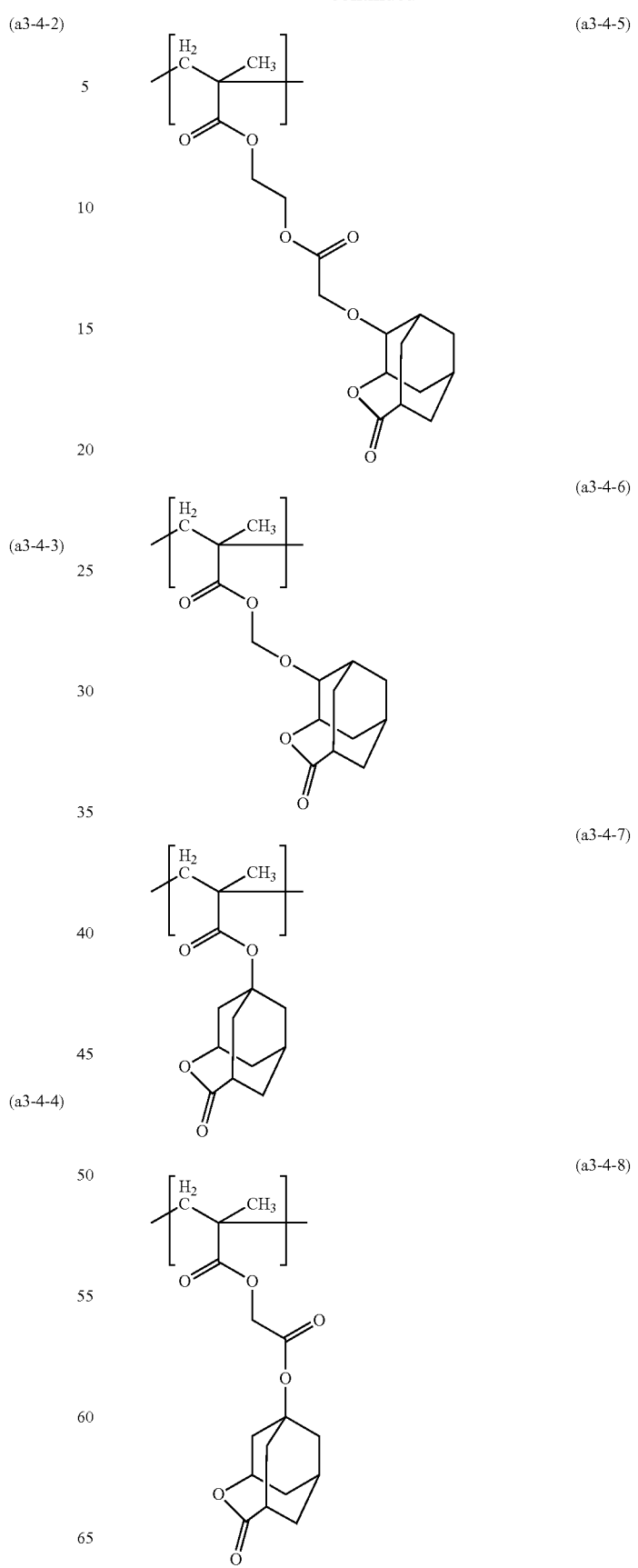
(a3-4-5)
(a3-4-6)
(a3-4-7)
(a3-4-8)

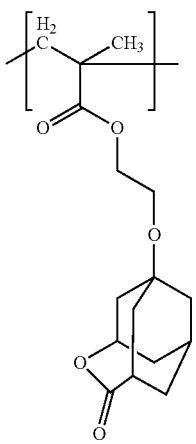

(a3-4-9)

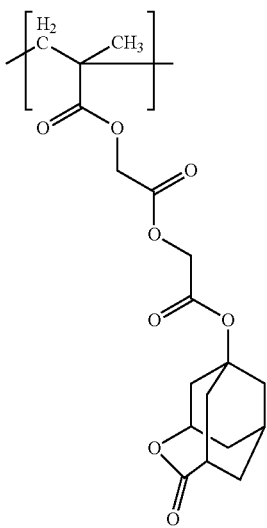

(a3-4-10)

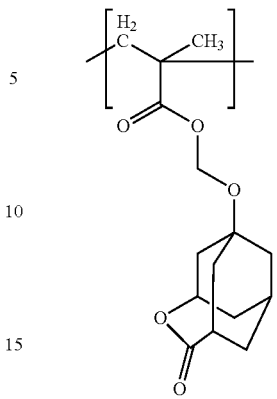

(a3-4-12)

Examples of the structural unit (a3) include those represented by the formula (a3-4-1) to the formula (a3-4-12) in which a methyl group corresponding to $R^{a24}$ has been replaced by a hydrogen atom.

When the resin (A) has the structural units (a3), the total proportion thereof is preferably 5% by mole to 70% by mole, more preferably 10% by mole to 65% by mole, still more preferably 10% by mole to 60% by mole, with respect to the total structural units (100% by mole) constituting the resin (A).

The proportion each of the formula (a3-1), the formula (a3-2), the formula (a3-3) and the formula (a3-4) is preferably 5% by mole to 60% by mole, more preferably 5% by mole to 50% by mole, still more preferably 10% by mole to 50% by mole, with respect to the total structural units (100% by mole) constituting the resin (A).

<Other Structural Unit (t)>

The resin (A) may further have a structural unit other than the structural unit (a1) and the structural unit (s) described above (which is sometimes referred to as "structural unit (t)"). Examples of the structural unit (t) include the structural unit (a4), the structural unit (a5) described above other than the structural unit (a2) and the structural unit (a3).

<Structural Unit (a4)>

Examples of the structural unit (a4) include a structural unit represented by formula (a4-0).

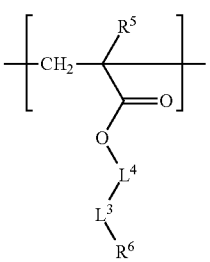

(a4-0)

(a3-4-11)

In the formula (a4-0), $R^5$ represents a hydrogen atom or a methyl group, $L^4$ represents a single bond or a $C_1$ to $C_4$ saturated aliphatic hydrocarbon group, $L^3$ represents a $C_1$ to $C_8$ perfluoroalkanediyl group, a $C_3$ to $C_{12}$ perfluorocycloalkanediyl group or a perfluoroadamantanediyl group, and $R^6$ represents a hydrogen atom or a fluorine atom.

Examples of the saturated aliphatic hydrocarbon group for L⁴ include $C_1$ to $C_4$ alkanediyl group, i.e., a liner alkanediyl group such as methylene, ethylene, propane-1,3-diyl, butane-1,4-diyl; and a branched alkanediyl group such as a group in which a liner alkanediyl group has a side chain of an alkyl group (e.g., methyl and ethyl groups), for example, ethane-J 1-diyl, propane-1,2-diyl, butane-1,3-diyl, 2-methylpropane-1,3-diyl and 2-methylpropane-1,2-diyl groups.

L⁴ is preferably a single bond, methylene or ethylene group, and more preferably a single bond or methylene group.

Examples of the perfluoroalkanediyl group for L³ include difluoromethylene, perfluoroethylene, perfluoroethylfluoromethylene, perfluoropropane-1,3-diyl, a perfluoropropane-1,2-diyl, perfluoropropane-2,2-diyl, perfluorobutane-1,4-diyl, perfluorobutane-2,2-diyl, perfluorobutane-1,2-diyl, perfluoropentane-1,5-diyl, perfluoropentane-2,2-diyl, perfluoropentane-3,3-diyl, perfluorohexane-1,6-diyl, perfluorohexane-2,2-diyl, perfluorohexane-3,3-diyl, perfluoroheptane-1,7-diyl, perfluoroheptane-2,2-diyl, perfluoroheptane-3,4-diyl, perfluoroheptane-4,4-diyl, perfluorooctan-1,8-diyl, perfluorooctan-2,2-diyl, perfluorooctan-3,3-diyl and perfluorooctan-4,4-diyl groups.

Examples of the perfluorocycloalkanediyl group for L³ include perfluorocyclohexanediyl, perfluorocyclopentanediyl, perfluorocycloheptanediyl and perfluoroadamantanediyl groups.

L³ is preferably a $C_1$ to $C_6$ perfluoroalkanediyl group, more preferably a $C_1$ to $C_3$ perfluoroalkanediyl group.

Examples of the structural unit (a4-0) include the following ones.

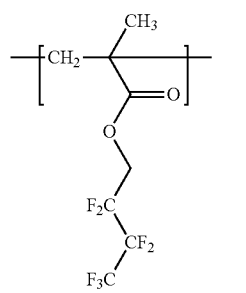
(a4-0-1)

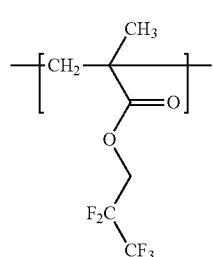
(a4-0-2)

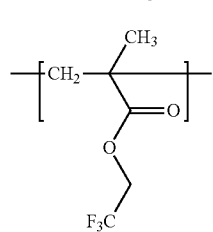
(a4-0-3)

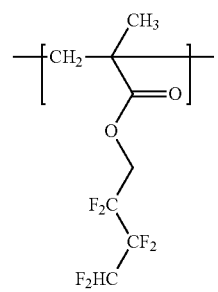
(a4-0-4)

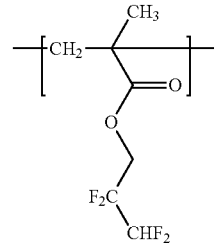
(a4-0-5)

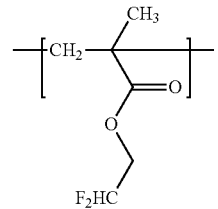
(a4-0-6)

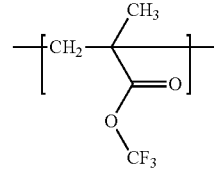
(a4-0-7)

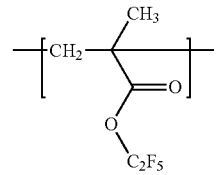
(a4-0-8)

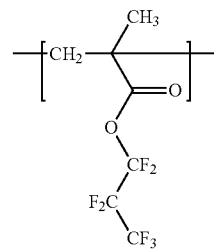
(a4-0-9)

(a4-0-10)
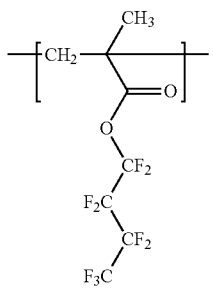

(a4-0-11)
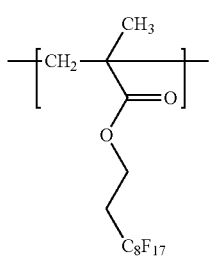

(a4-0-12)
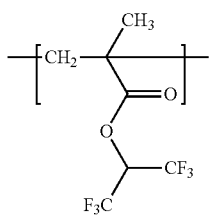

(a4-0-13)
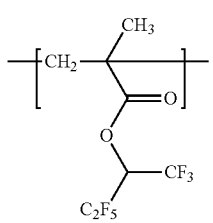

(a4-0-14)
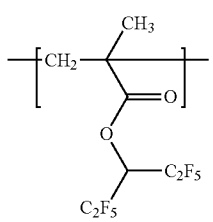

(a4-0-15)
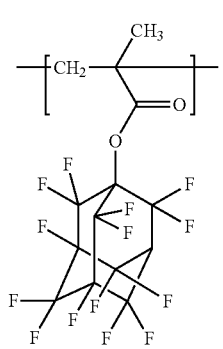

(a4-0-16)
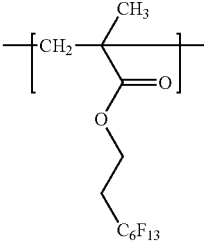

Examples of the structural unit (a4-0) include those represented by the above formulae in which a methyl group corresponding to $R^5$ has been replaced by a hydrogen atom.

Examples of the structural unit (a4) include the structural units represented by formula (a4-1):

(a4-1)
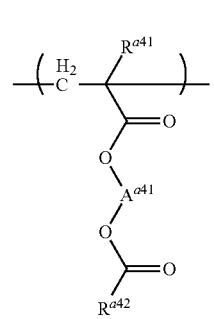

wherein $R^{a41}$ represents a hydrogen atom or a methyl group, $R^{a42}$ represents an optionally substituted $C_1$ to $C_{20}$ hydrocarbon group where a methylene group may be replaced by an oxygen atom or a carbonyl group, and $A^{a41}$ represents an optionally substituted $C_1$ to $C_6$ alkanediyl group or a group represented by formula (a-g1), (a-g1)

wherein s represents 0 or 1, $A^{a42}$ and $A^{a44}$ each independently represent an optionally substituted $C_1$ to $C_5$ aliphatic hydrocarbon group, $A^{a43}$ represents a single bond or an optionally substituted $C_1$ to $C_5$ aliphatic hydrocarbon group, and $X^{a41}$ and $X^{a42}$ each independently represent —O—, —CO—, —CO—O— or —O—CO—, provided that the carbon atoms contained in $A^{a42}$, $A^{a43}$, $A^{a44}$, $X^{a41}$ and $X^{a42}$ is 7 or less in total, and

* and ** represent a binding site, and * represents a binding site to —O—CO— $R^{a42}$.

At least one of $A^{a41}$ and $R^{a42}$ preferably has a halogen atom as a substituent.

The hydrocarbon group for $R^{a42}$ may be a chain and a cyclic aliphatic hydrocarbon groups, an aromatic hydrocarbon group and a combination thereof.

The chain and the cyclic aliphatic hydrocarbon group may have a carbon-carbon unsaturated bond, and is preferably a chain and a cyclic saturated aliphatic hydrocarbon group. Examples of the saturated aliphatic hydrocarbon group include a liner or branched alkyl group, a monocyclic or polycyclic alicyclic hydrocarbon group, and an aliphatic hydrocarbon group formed by combining the alkyl group and the alicyclic hydrocarbon group.

Examples of the chain aliphatic hydrocarbon group include an alkyl group such as methyl, ethyl, propyl, butyl, pentyl, hexyl, heptyl, octyl, decyl, dodecyl and hexadecyl groups.

Examples of the alicyclic hydrocarbon group include a cycloalkyl group such as cyclopentyl, cyclohexyl, cycloheptyl, cyclooctyl groups; and polycyclic hydrocarbon groups such as decahydronaphtyl, adamantyl and norbornyl groups as well as groups below. * represents a binding site.

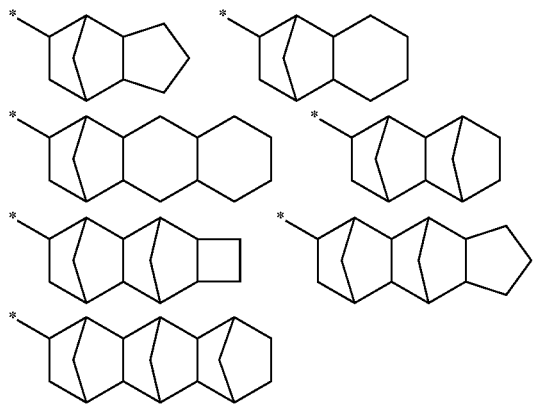

Examples of the aromatic hydrocarbon group include an aryl group such as phenyl, naphthyl, anthryl, biphenyl, phenanthryl and fluorenyl groups.

The hydrocarbon group for $R^{a42}$ is preferably a chain and a cyclic aliphatic hydrocarbon groups, and a combination thereof. The hydrocarbon group may have a carbon-carbon unsaturated bond, is preferably a chain and a cyclic saturated aliphatic hydrocarbon groups, and a combination thereof.

Examples of the substituent for $R^{a42}$ include a halogen atom or a group represented by formula (a-g3).

wherein $X^{a43}$ represent an oxygen atom, a carbonyl group, a carbonyloxy group or an oxycarbonyl group, $A^{a45}$ represents a $C_1$ to $C_{17}$ aliphatic hydrocarbon group that has a halogen atom, and

* represents a binding site.

Examples of the halogen atom include fluorine, chlorine, bromine or iodine atom, and preferably a fluorine atom.

Examples of the aliphatic hydrocarbon group for $A^{a45}$ include the same ones as those for $R^{a42}$.

$R^{a42}$ is preferably an aliphatic hydrocarbon group that may have a halogen atom, and more preferably an alkyl group having a halogen atom and/or an aliphatic hydrocarbon group having the group represented by the formula (a-g3).

When $R^{a42}$ is an aliphatic hydrocarbon group having a halogen atom, an aliphatic hydrocarbon group having a fluorine atom is preferred, a perfluoroalkyl group or a perfulorocycloalkyl group are more preferred, a $C_1$ to $C_6$ perfluoroalkyl group is still more preferred, a $C_1$ to $C_3$ perfluoroalkyl group is particularly preferred.

Examples of the perfluoroalkyl group include perfluoromethyl, perfluoroethyl, perfluoropropyl, perfluorobutyl, perfluoropentyl, perfluorohexyl, perfluoroheptyl and perfluorooctyl groups. Examples of the perfluorocycloalkyl group include perfluorocyclohexyl group.

When $R^{a42}$ is an aliphatic hydrocarbon group having the group represented by the formula (a-g3), the carbon atoms contained in the aliphatic hydrocarbon group including the group represented by the formula (a-g3) is preferably 15 or less, more preferably 12 or less in total. The number of the group represented by the formula (a-g3) is preferably one when the group represented by the formula (a-g3) is the substituent.

The aliphatic hydrocarbon group having the group represented by the formula (a-g3) is more preferably a group represented by formula (a-g2):

wherein $A^{a46}$ represents a $C_1$ to $C_{17}$ aliphatic hydrocarbon group that may have a halogen atom, $X^{a44}$ represent a carbonyloxy group or an oxycarbonyl group, $A^{a47}$ represents a $C_1$ to $C_{17}$ aliphatic hydrocarbon group that may have a halogen atom, provided that the carbon atoms contained in $A^{a46}$, $X^{a44}$ and $X^{a44}$ is 18 or less in total, at least one of $A^{a46}$ and $A^{a47}$ has a halogen atom, and

* represents a binding site to a carbonyl group.

The aliphatic hydrocarbon group for $A^{a46}$ has preferably 1 to 6 carbon atoms, more preferably 1 to 3, carbon atoms.

The the aliphatic hydrocarbon group for $A^{a47}$ has preferably 4 to 15 carbon atoms, more preferably 5 to 12 carbon atoms. $A^{a47}$ is more preferably a cyclohexyl group or an adamantyl group.

Preferred examples of *-$A^{a46}$-$X^{a44}$-$A^{a47}$ include the following ones.

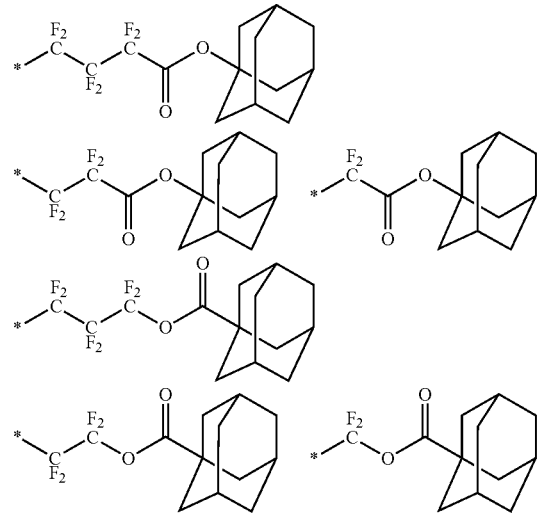

Examples of the alkanediyl group for $A^{a41}$ include a liner alkanediyl group such as methylene, ethylene, propane-1,3-diyl, butane-1,4-diyl, pentane-1,5-diyl and hexane-1,6-diyl groups;

a branched alkanediyl group such as propane-1,2-diyl, butan-1,3-diyl, 2-methylpropane-1,2-diyl, 1-methylbutane-1,4-diyl, 2-methylbutane-1,4-diyl groups.

Examples of the substituent on the alkanediyl group for $A^{a41}$ include a hydroxy group and a $C_1$ to $C_6$ alkoxy group.

Examples of the substituent on the alkanediyl for $A^{a41}$ include a hydroxy group and a $C_1$ to $C_6$ alkoxy group.

$A^{a41}$ is preferably a $C_1$ to $C_4$ alkanediyl group, more preferably a $C_2$ to $C_4$ alkanediyl group, and still more preferably ethylene group.

In the group represented by the formula (a-g1) (which is sometimes referred to as "group (a-g1)"), examples of the aliphatic hydrocarbon group for $A^{a42}$, $A^{a43}$ and $A^{a44}$ include methylene, ethylene, propane-1,3-diyl, propane-1,2-diyl, butane-1,4-diyl, 1-methylpropane-1,3-diyl, 2-methylpropane-1,3-diyl and 2-methylpropane-1,2-diyl groups.

Examples of the substituent on the aliphatic hydrocarbon group for $A^{a42}$, $A^{a43}$ and $A^{a44}$ include a hydroxy group and a $C_1$ to $C_6$ alkoxy group.

s is preferably 0.

Examples of the group (a-g1) in which $X^{a42}$ represents an oxygen atom include the following ones. In the formula, * and  each represent a binding site, and  represents a binding site to —O—CO—$R^{a42}$

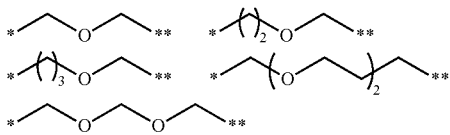

Examples of the group (a-g1) in which $X^{a42}$ represents a carbonyl group include the following ones.

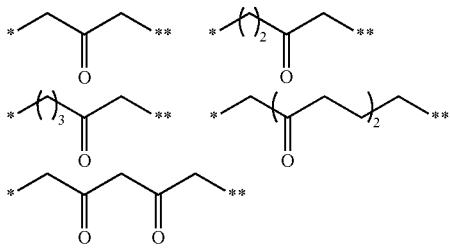

Examples of the group (a-g1) in which $X^{a42}$ represents a carbonyloxy group include the following ones.

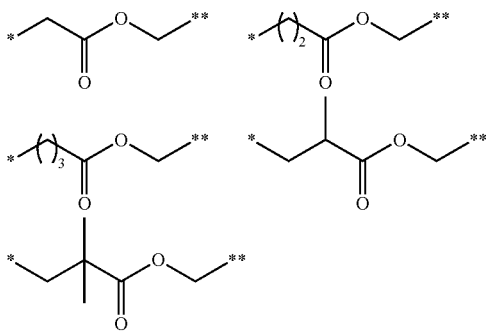

Examples of the group (a-g1) in which $X^{a42}$ represents an oxycarbonyl group include the following ones.

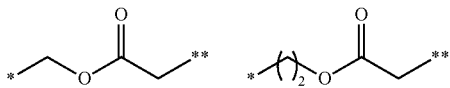

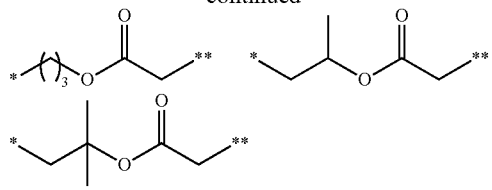

The structural unit represented by the formula (a4-1) is preferably structural units represented by formula (a4-2) and formula (a4-3):

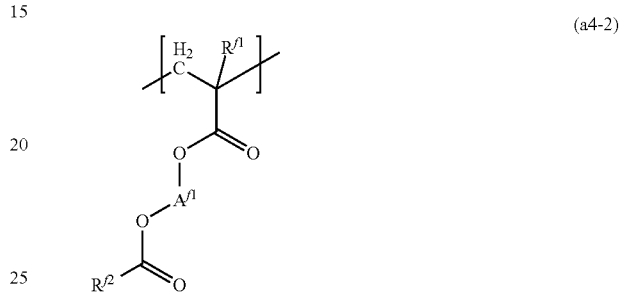

(a4-2)

wherein $R^{f1}$ represents a hydrogen atom or a methyl group,
$A^{f1}$ represent a $C_1$ to $C_6$ alkanediyl group, and
$R^{f12}$ represents a $C_1$ to $C_{10}$ hydrocarbon group that has a fluorine atom.

Examples of the alkanediyl group for $A^{f1}$ include a liner alkanediyl group such as methylene, ethylene, propane-1,3-diyl, propane-1,2-diyl, butane-1,4-diyl, pentane-1,5-diyl and hexane-1,6-diyl groups;

a branched alkanediyl group such as 1-methylpropane-1,3-diyl, 2-methylpropane-1,3-diyl, 2-methylpropane-1,2-diyl, 1-methylbutane-1,4-diyl and 2-methylbutane-1,4-diyl groups.

The hydrocarbon group for $R^{f2}$ includes a1 aliphatic hydrocarbon group and an aromatic hydrocarbon group. The aliphatic hydrocarbon group includes a chain and a cyclic groups, and a combination thereof. The aliphatic hydrocarbon group is preferably an alkyl group and a cyclic aliphatic hydrocarbon group.

Examples of the alkyl group include methyl, ethyl, n-propyl, isopropyl, n-butyl, sec-butyl, tert-butyl, n-pentyl, n-hexyl, n-heptyl, n-octyl and 2-ethylhexyl groups.

Examples of the cyclic aliphatic hydrocarbon group include any of a monocyclic group and a polycyclic group. Examples of the monocyclic alicyclic hydrocarbon group include a cycloalkyl group such as cyclopropyl, cyclobutyl, cyclopentyl, cyclohexyl, methylcyclohexyl, dimethylcyclohexyl, cycloheptyl, cyclooctyl, and cyclodecyl groups. Examples of the polycyclic hydrocarbon groups includes decahydronaphthyl, adamantyl, 2-alkyladamantane-2-yl, 1-(adamantane-1-yl) alkane-1-yl, norbornyl, methylnorbornyl and isobornyl groups.

Examples of the hydrocarbon group having a fluorine atom for $R^{f2}$ include an alkyl group having a fluorine atom and an alicyclic hydrocarbon group having a fluorine atom.

Specific examples of an alkyl group having a fluorine atom include a fluorinated alkyl group such as difluoromethyl, trifluoromethyl, 1,1-difluoroethyl, 2,2-difluoroethyl, 2,2,2-trifluoroethyl, perfluoroethyl, 1,1,2,2-tetrafluoropropyl, 1,2,2,3,3-hexafluoropropyl, perfluoroethylmethyl, 1-(trifluoromethyl)-1,2,2,2-tetrafluoroethyl, perfluoropropyl, 1-(trifluoromethyl)-2,2,2-trifluoroethyl, perfluoropropyl, 1,1,2,2-tetrafluorobutyl, 1,1,2,2,3,3-hexafluorobutyl, 1,1,2,2,3,3,4,4-octafluorobutyl, perfluorobutyl, 1,1-bis(trifluoro)methyl-2,2,2-trifluoroethyl, 2-(perfluoropropyl)ethyl, 1,1,2,2,3,3,4,4-octafluoropentyl, perfluoropentyl, 1,1,2,2,3,3,4,4,5,5-decafluoropentyl, 1,1-bis(trifluoromethyl)2,2,3,3,3-pentafluoropropyl, 2-(perfluorobutyl)ethyl, 1,1,2,2,3,3,4,5,5-decafluorohexyl, 1,1,2,2,3,3,4,5,5,6,6-dodecafluorohexyl, perfluoropentylmethyl and perfluorohexyl groups.

Examples of the alicyclic hydrocarbon group having a fluorine atom include a fluorinated cycloalkyl group such as perfluorocycohexyl and perfluoroadamantyl groups.

In the formula (a4-2), $A^{f1}$ is preferably a $C_2$ to $C_4$ alkanediyl group, and more preferably an ethylene group.

$R^{f2}$ is preferably a $C_1$ to $C_6$ fluorinated alkyl group.

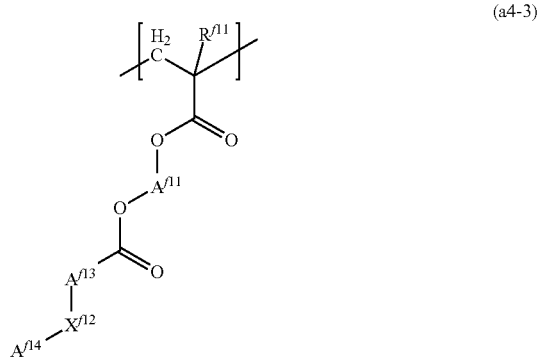

(a4-3)

In the formula (a4-3), $R^{f11}$ represents a hydrogen atom or a methyl group, $A^{f11}$ represent a $C_1$ to $C_6$ alkanediyl group, $A^{f13}$ represents a $C_1$ to $C_{18}$ aliphatic hydrocarbon group that may have a fluorine atom, $X^{f12}$ represents an oxycarbonyl group or a carbonyloxy group, $A^{f14}$ represents a $C_1$ to $C_{17}$ aliphatic hydrocarbon group that may have a fluorine atom, and provided that at least one of $A^{f13}$ and $A^{f14}$ represents an aliphatic hydrocarbon group having a fluorine atom.

Examples of the alkanediyl group for $A^{f11}$ include the same ones as those for $A^{f1}$.

Examples of the aliphatic hydrocarbon group for $A^{f13}$ include any of a divalent chain or cyclic aliphatic hydrocarbon group, or a combination thereof. The aliphatic hydrocarbon group may have a carbon-carbon unsaturated bond, and is preferably a saturated aliphatic hydrocarbon group.

The aliphatic hydrocarbon group that may have a fluorine atom for $A^{f13}$ is preferably the saturated aliphatic hydrocarbon group that may have a fluorine atom, and more preferably perfluoroalkandiyl group.

Examples of the divalent chain aliphatic hydrocarbon that may have a fluorine atom include an alkanediyl group such as methylene, ethylene, propanediyl, butanediyl and pentanediyl groups; a perfluoroalkanediyl group such as difluoromethylene, perfluoroethylene, perfluoropropanediyl, perfluorobutanediyl and perfluoropentanediyl groups.

The divalent cyclic aliphatic hydrocarbon group that may have a fluorine atom is any of monocyclic or polycyclic group.

Examples monocyclic aliphatic hydrocarbon group include cyclohexanediyl and perfluorocyclohexanediyl groups.

Examples polycyclic aliphatic hydrocarbon group include adamantanediyl, norbornanediyl, and perfluoroadamantanediyl groups.

Examples of the aliphatic hydrocarbon group for $A^{f14}$ include any of a chain or a cyclic aliphatic hydrocarbon group, or a combination thereof. The aliphatic hydrocarbon group may have a carbon-carbon unsaturated bond, and is preferably a saturated aliphatic hydrocarbon group.

The aliphatic hydrocarbon group that may have a fluorine atom for $A^{f14}$ is preferably the saturated aliphatic hydrocarbon group that may have a fluorine atom.

Examples of the chain aliphatic hydrocarbon group that may have a halogen atom include trifluoromethyl, difluoromethyl, methyl, perfluoromethyl, 1,1,1-trifluoroethyl, 1,1,2,2-tetrafluoroethyl, ethyl, perfluoropropyl, 1,1,1,2,2-pentafluoropropyl, propyl, perfluorobutyl, 1,1,2,2,3,3,4,4-octafluorobutyl, butyl, perfluoropentyl, 1,1,1,2,2,3,3,4,4-nonafluoropentyl, pentyl, hexyl, perfluorohexyl, hepthyl, perfluoroheptyl, octyl and perfluorooctyl groups.

The cyclic aliphatic hydrocarbon group that may have a fluorine atom may be any of a monocyclic group and a polycyclic group. Examples of the group containing the monocyclic aliphatic hydrocarbon group include cyclopropylmethyl, cyclopropyl, cyclobutylmethyl, cyclopentyl, cyclohexyl and perfluorocyclohexyl groups. Examples of the group containing the polycyclic aliphatic hydrocarbon group includes adamantyl, adamantylmethyl, norbornyl, norbornylmethyl, perfluoroadamantyl and perfluoroadamantylmethyl groups In the formula (a4-3), $A^{f11}$ is preferably an ethylene group.

The aliphatic hydrocarbon group for $A^{f13}$ is preferably a $C_1$ to $C_6$ aliphatic hydrocarbon group, more preferably a $C_2$ to $C_3$ aliphatic hydrocarbon group.

The aliphatic hydrocarbon group for $A^{f14}$ is preferably a $C_3$ to $C_{12}$ aliphatic hydrocarbon group, more preferably a $C_3$ to $C_{10}$ aliphatic hydrocarbon group. Among these, $A^{f14}$ is preferably a group containing a $C_3$ to $C_{12}$ alicyclic hydrocarbon group, more preferably cyclopropylmethyl, cyclopentyl, cyclohexyl, norbornyl and adamantly groups.

Examples of the structural unit (a4-2) include structural units represented by formula (a4-1-1) to formula (a4-1-22).

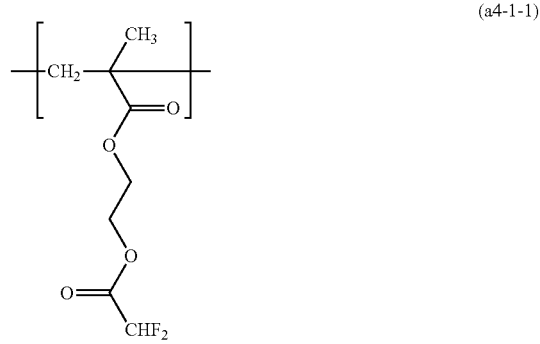

(a4-1-1)

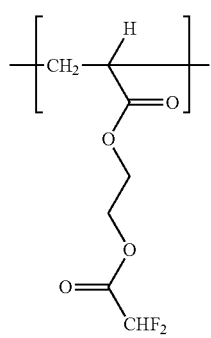
(a4-1-2)
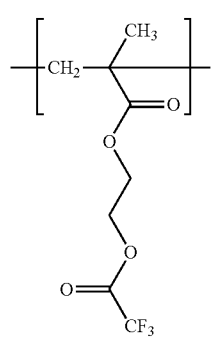
(a4-1-3)
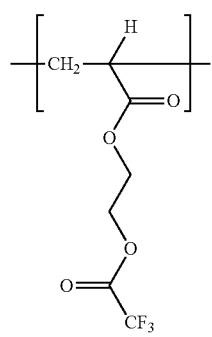
(a4-1-4)
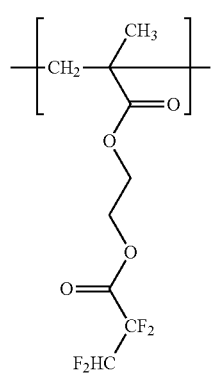
(a4-1-5)
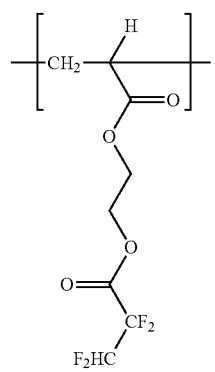
(a4-1-6)
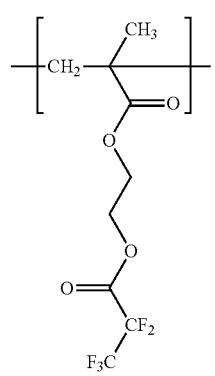
(a4-1-7)
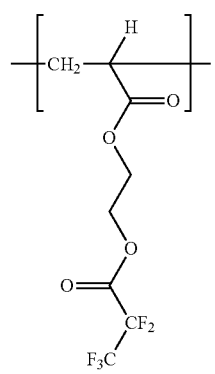
(a4-1-8)
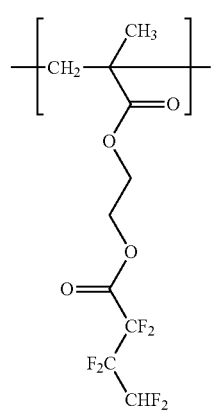
(a4-1-9)

(a4-1-10)
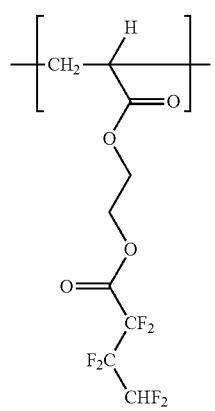
(a4-1-11)
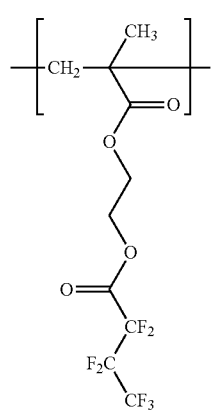
(a4-1-12)
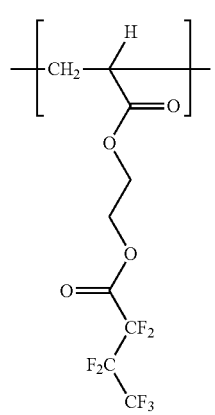
(a4-1-13)
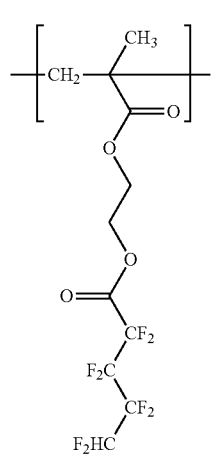
(a4-1-14)
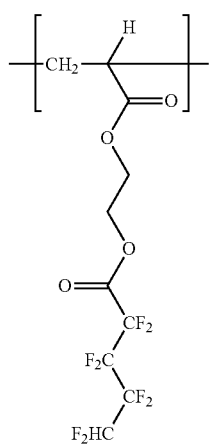
(a4-1-15)
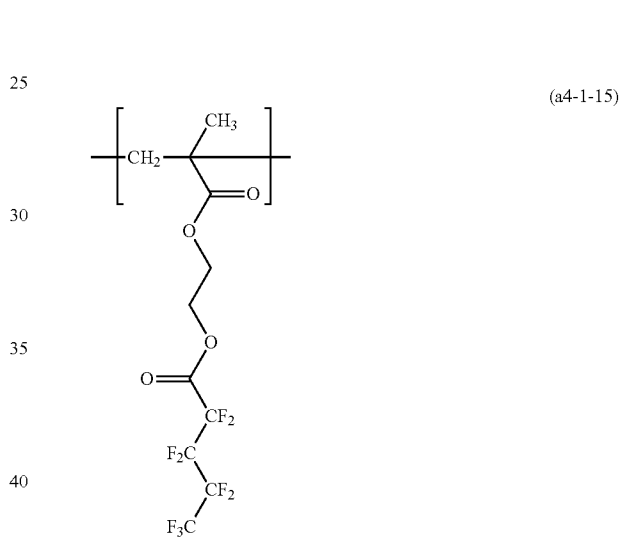
(a4-1-16)
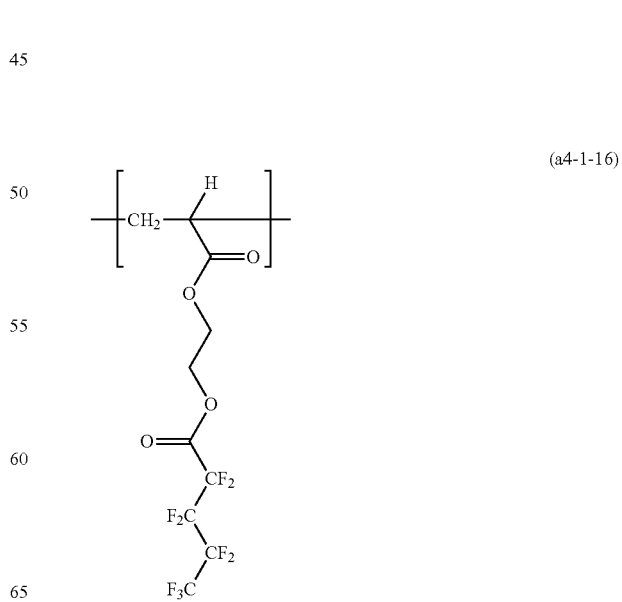

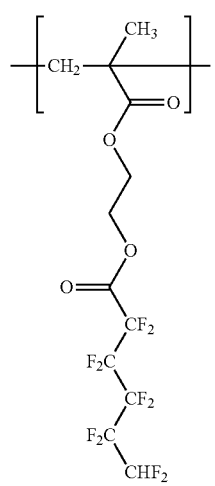
(a4-1-17)
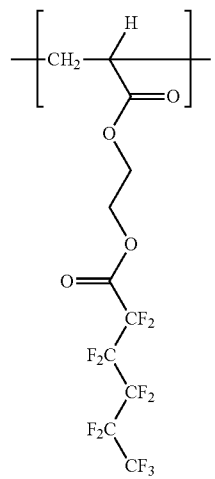
(a4-1-20)
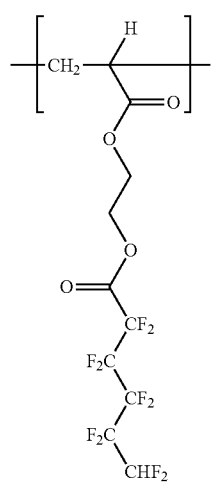
(a4-1-18)
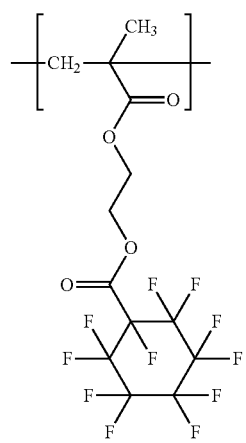
(a4-1-21)
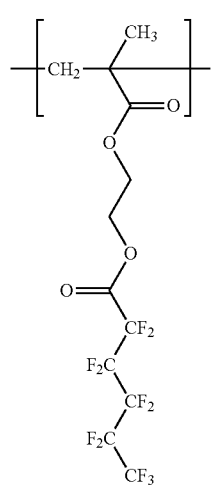
(a4-1-19)
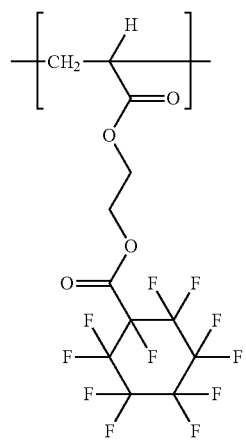
(a4-1-22)
Examples of the structural unit (a4-3) include structural units presented by formula (a4-1'-1) to formula (A4-1'-22).

(a4-1'-1)
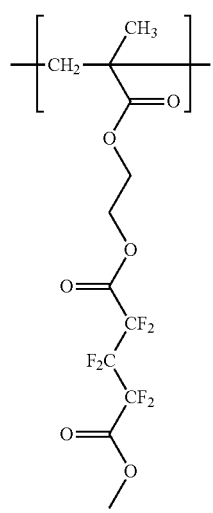
(a4-1'-2)
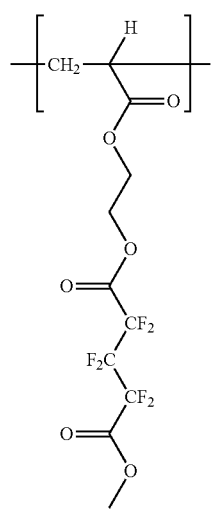
(a4-1'-3)
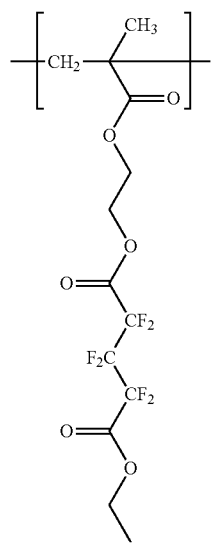
-continued
(a4-1'-4)
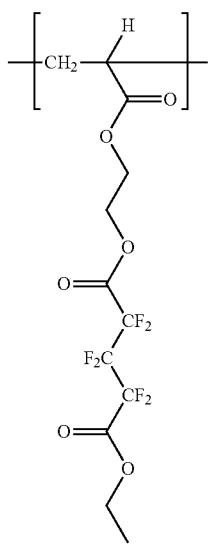
(a4-1'-5)
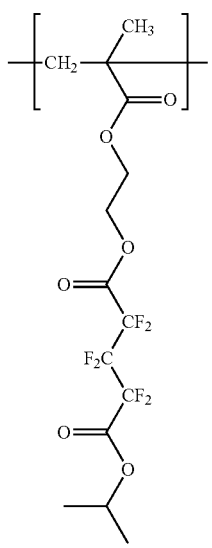
(a4-1'-6)
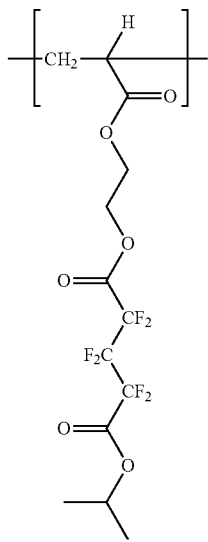

(a4-1'-7)
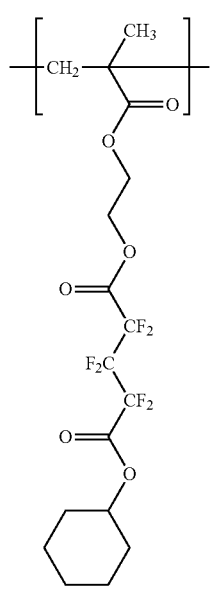
(a4-1'-8)
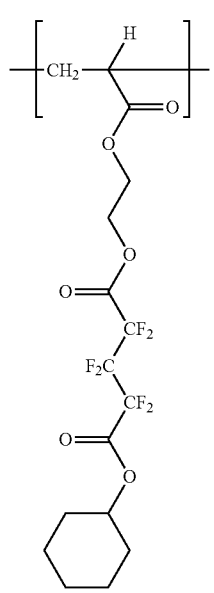
(a4-1'-9)
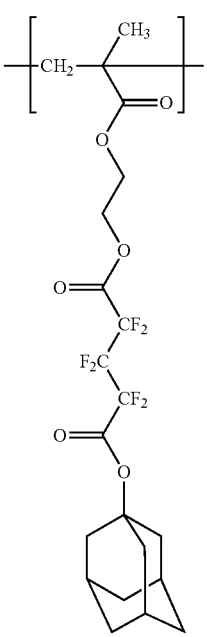
(a4-1'-10)
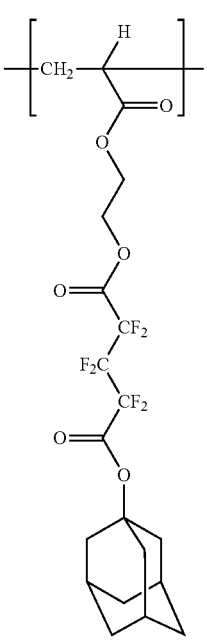

(a4-1'-11) 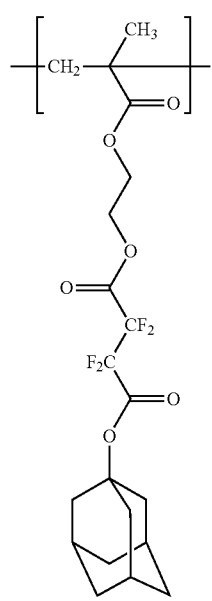
(a4-1'-13) 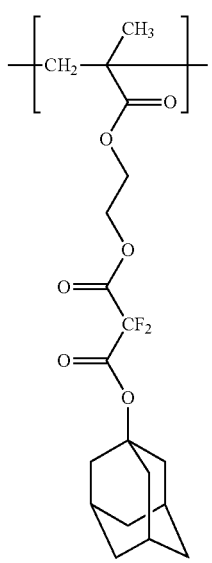
(a4-1'-12) 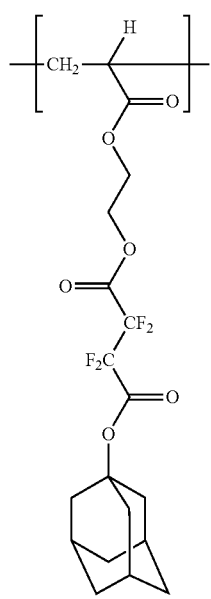
(a4-1'-14) 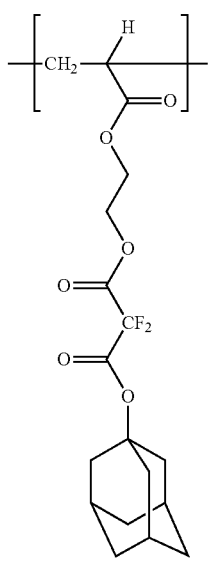

(a4-1'-15)
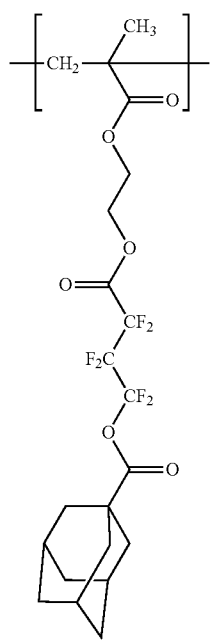
(a4-1'-17)
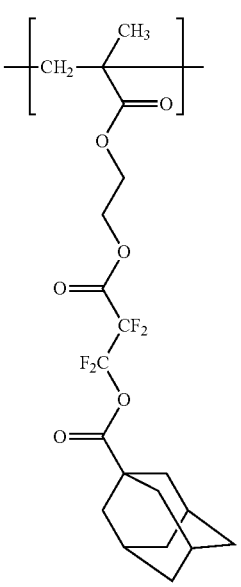
(a4-1'-16)
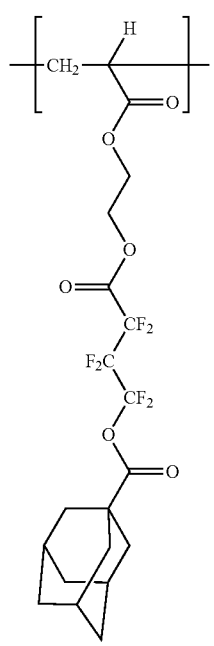
(a4-1'-18)
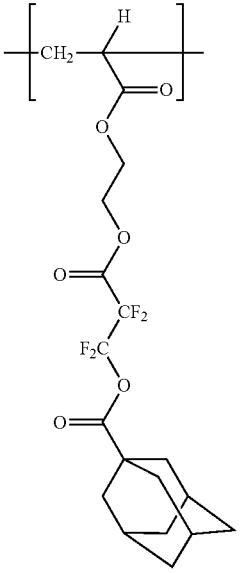

(a4-1'-19) 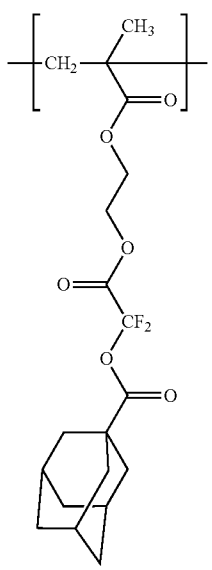

(a4-1'-20)

(a4-1'-21)

(a4-1'-22) 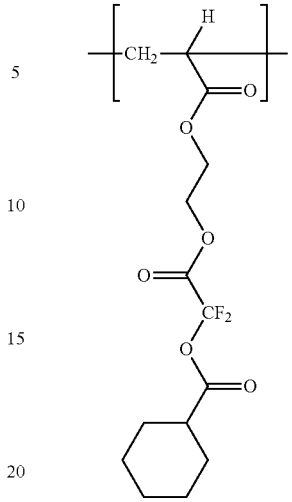

Examples of the structural unit (a4) include a structural unit presented by formula (a4-4):

(a4-4) 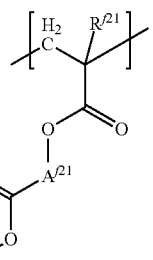

wherein $R^{l21}$ represents a hydrogen atom or a methyl group, $A^{l21}$ represents *—$(CH_2)_{j1}$—, *—$(CH_2)_{j2}$—O—$(CH_2)_{j3}$— or *—$(CH_2)_{j4}$—CO—O—$(CH_2)_{j5}$—, where

* represents a binding site to an oxygen atom, j1 to j5 each independently represents an integer of 1 to 6, and $R^{l22}$ represents a $C_1$ to $C_{10}$ hydrocarbon group having a fluorine atom.

Examples of the hydrocarbon group having a fluorine atom for $R^{l22}$ include the same ones as those for $R^{l2}$ in the formula (a4-2). $R^{l22}$ is preferably a $C_1$ to $C_{10}$ alkyl group having a fluorine atom or a $C_3$ to $C_{10}$ alicyclic hydrocarbon group having a fluorine atom, more preferably a $C_1$ to $C_{10}$ alkyl group having a fluorine atom, and still more preferably a $C_1$ to $C_6$ alkyl group having a fluorine atom.

In the formula (a4-4), $A^{l21}$ is preferably —$(CH_2)_{j1}$—, more preferably a methylene group or an ethylene group, and still more preferably a methylene group.

Examples of the structural unit represented by the formula (a4-4) include the following ones.

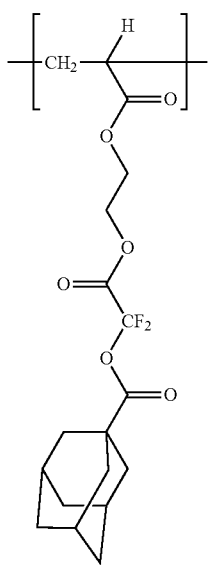

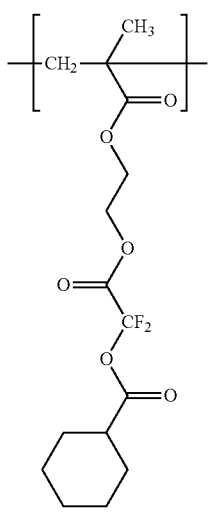

83
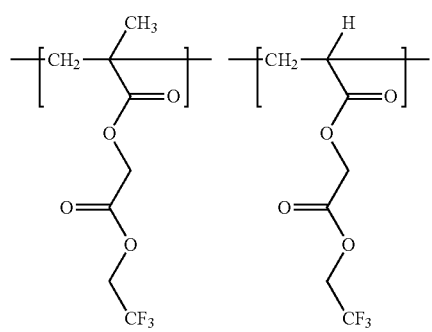
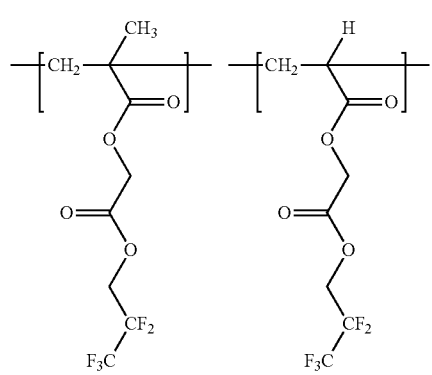
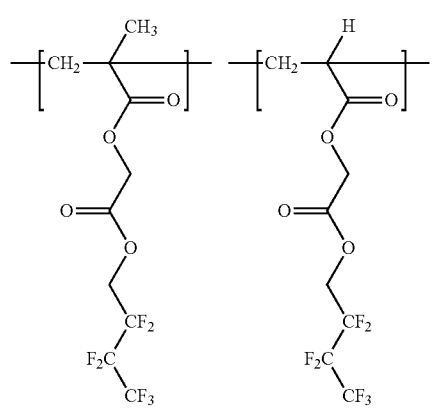
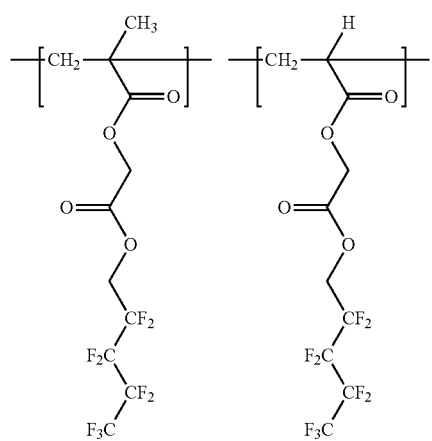
84
-continued
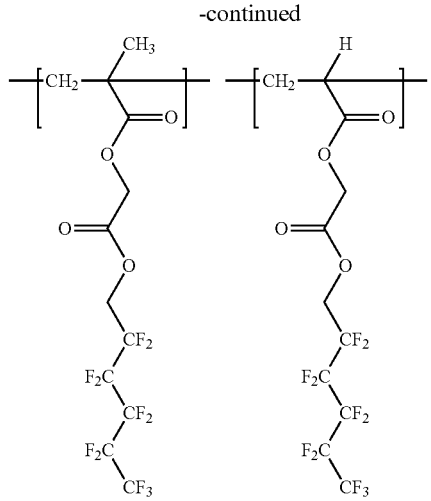
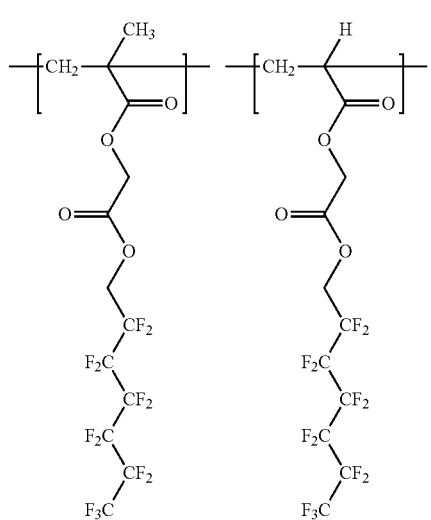
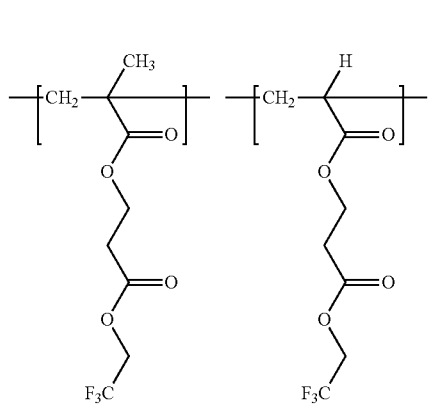

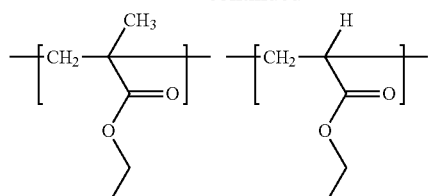
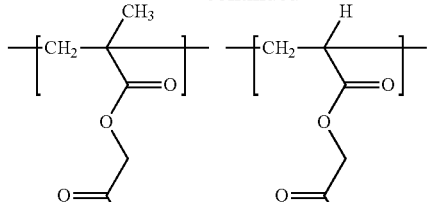

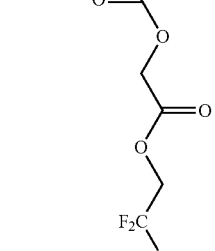

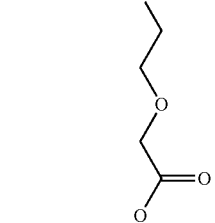

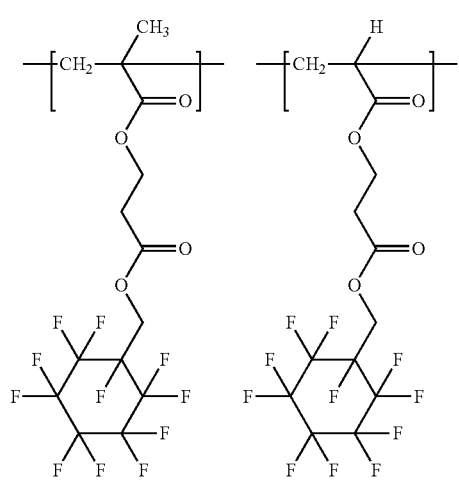

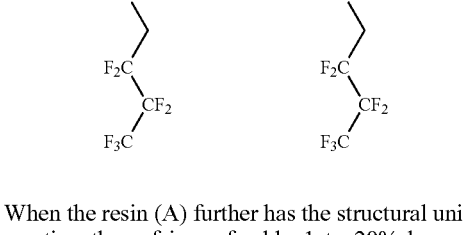

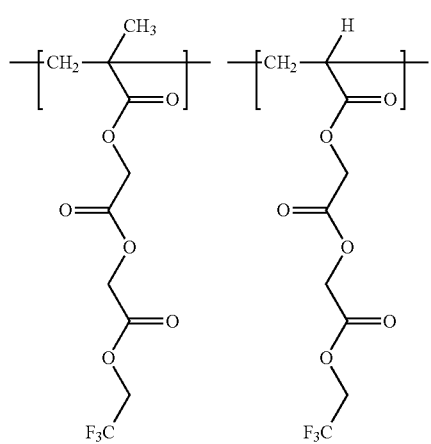

When the resin (A) further has the structural unit (a4), the proportion thereof is preferably 1 to 20% by mole, more preferably 2 to 15% by mole, and still more preferably 3 to 10% by mole, with respect to the total structural units (100% by mole) of the resin (A).

<Structural Unit (a5)>

Examples of the non-leaving hydrocarbon group in the structural unit (a5) include a liner or branched, or a cyclic hydrocarbon group. Among these, the structural unit (a5) preferably has a structural unit having an alicyclic hydrocarbon group. The structural unit (a5) includes a structural unit represented by formula (a5-1), which is sometimes referred to as "structural unit (a5-1)".

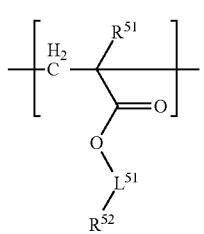

(a5-1)

In the formula (a5-1), $R^{51}$ represents a hydrogen atom or a methyl group, $R^{52}$ represents a $C_3$ to $C_{18}$ alicyclic hydrocarbon group where a hydrogen atom may be replaced by a $C_1$ to $C_8$ aliphatic hydrocarbon group or a hydroxy group, provided that the carbon atom directly bonded to $L^{51}$ has no aliphatic hydrocarbon group by which a hydrogen atom has been replaced, and $L^{51}$ represents a single bond or a $C_1$ to $C_{18}$ divalent saturated hydrocarbon group where a methylene group may be replaced by an oxygen atom or a carbonyl group.

Examples of the alicyclic hydrocarbon group for $R^{52}$ include any one of a monocyclic group or a polycyclic group. Examples of the monocyclic alicyclic hydrocarbon group include cyclopropyl, cyclobutyl, cyclopentyl and cyclohexyl groups. Examples of the polycyclic hydrocarbon group include adamantyl and norbornyl groups.

Examples of the $C_1$ to $C_8$ aliphatic hydrocarbon group include an alkyl group such as methyl, ethyl, n-propyl, isopropyl, n-butyl, sec-butyl, tert-butyl, n-pentyl, n-hexyl, n-heptyl, 2-ethylhexyl and n-octyl groups.

Examples of the alicyclic hydrocarbon group having a substituent for $R^{52}$ include 3-hydroxyadamantyl group and 3-methyladamantyl group.

$R^{52}$ is preferably an unsubstituted $C_3$ to $C_{18}$ alicyclic hydrocarbon group, and more preferably an adamantyl, norbornyl or cyclohexyl group.

Examples of the divalent saturated hydrocarbon group for $L^{51}$ include a divalent saturated aliphatic hydrocarbon group and a divalent saturated alicyclic hydrocarbon group, and a divalent saturated aliphatic hydrocarbon group is preferred.

Examples of the divalent saturated aliphatic hydrocarbon group include an alkanediyl such as methylene, ethylene, propanediyl, butanediyl and pentanediyl.

Examples of the divalent saturated alicyclic hydrocarbon group include any of a monocyclic group and a polycyclic group. Examples of the monocyclic group include cycloalkanediyl group such as cyclopentanediyl and cyclohexanediyl groups. Examples of the polycyclic group include adamantanediyl and norbornanediyl groups.

Examples of the saturated hydrocarbon group in which a methylene group has been replaced by an oxygen atom or a carbonyl group include groups represented by formula (L1-1) to formula (L1-4). In formula (L1-1) to formula (L1-4), * represents a binding site to an oxygen atom.

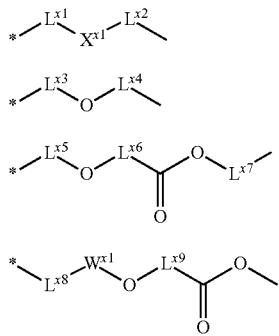

(L1-1)

(L1-2)

(L1-3)

(L1-4)

In the formulae, $X^{X1}$ represents an oxycarbonyl group or a carbonyloxy group, $L^{X1}$ represents a $C_1$ to $C_{16}$ divalent saturated aliphatic hydrocarbon group, $L^{X2}$ represents a single bond or a $C_1$ to $C_{15}$ divalent saturated aliphatic hydrocarbon group, provided that the carbon atoms contained in $L^{X1}$ and $L^{X2}$ is 16 or less in total;

$L^{X3}$ represents a single bond or a $C_1$ to $C_{17}$ divalent saturated aliphatic hydrocarbon group, $L^{X4}$ represents a single bond or a $C_1$ to $C_{16}$ divalent saturated aliphatic hydrocarbon group, provided that the carbon atoms contained in $L^{X3}$ and $L^{X4}$ is 17 or less in total;

$L^{X5}$ represents a $C_1$ to $C_{15}$ divalent saturated aliphatic hydrocarbon group, $L^{X6}$ and $L^{X7}$ each independently represent a single bond or a $C_1$ to $C_{14}$ divalent saturated aliphatic hydrocarbon group, provided that the carbon atoms contained in $L^{X5}$, $L^{X6}$ and $L^{X7}$ is 15 or less in total;

$L^{X8}$ and $L^{X9}$ each independently represent a single bond or a $C_1$ to $C_{12}$ divalent saturated aliphatic hydrocarbon group, $W^{X1}$ represents a $C_3$ to $C_{15}$ divalent saturated alicyclic hydrocarbon group, provided that the carbon atoms contained in $L^{X8}$, $L^{X9}$ and $W^{X1}$ is 15 or less in total.

$L^{X1}$ is preferably a $C_1$ to $C_8$ divalent saturated aliphatic hydrocarbon group, and more preferably a methylene group or an ethylene group.

$L^{X2}$ is preferably a single bond or a $C_1$ to $C_8$ divalent saturated aliphatic hydrocarbon group, and more preferably a single bond.

$L^{X3}$ is preferably a $C_1$ to $C_8$ divalent saturated aliphatic hydrocarbon group.

$L^{X4}$ is preferably a single bond or a $C_1$ to $C_8$ divalent saturated aliphatic hydrocarbon group.

$L^{X5}$ is preferably a $C_1$ to $C_8$ divalent saturated aliphatic hydrocarbon group, and more preferably a methylene group or an ethylene group.

$L^{X6}$ is preferably a single bond or a $C_1$ to $C_8$ divalent saturated aliphatic hydrocarbon group, and more preferably a methylene group or an ethylene group.

$L^{X7}$ is preferably a single bond or a $C_1$ to $C_8$ divalent saturated aliphatic hydrocarbon group.

$L^{X8}$ is preferably a single bond or a $C_1$ to $C_8$ divalent saturated aliphatic hydrocarbon group, and more preferably a single bond or a methylene group.

$L^{X9}$ is preferably a single bond or a $C_1$ to $C_8$ divalent saturated aliphatic hydrocarbon group, and more preferably a single bond or a methylene group.

$W^{X1}$ is preferably a $C_3$ to $C_{10}$ divalent saturated alicyclic hydrocarbon group, and more preferably a cyclohexanediyl or adamantanediyl group.

Examples of the group represented by the formula (L1-1) include the following ones.

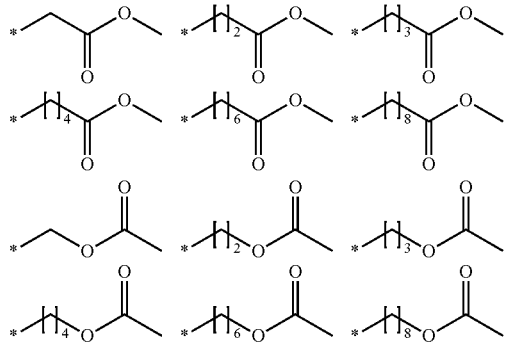

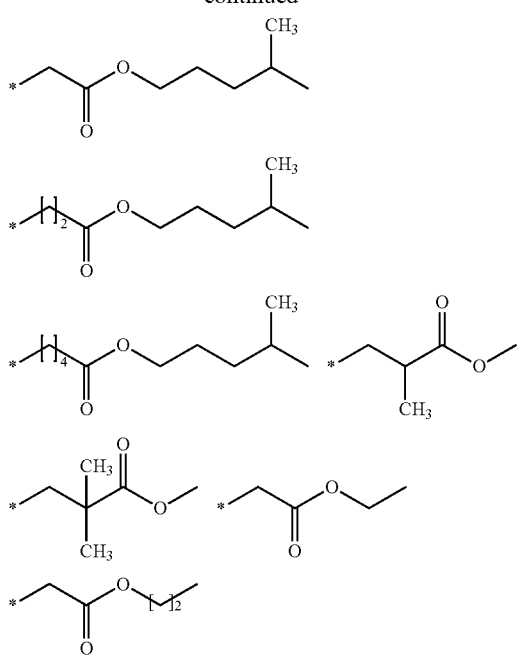

Examples of the group represented by the formula (L1-2) include the following ones.

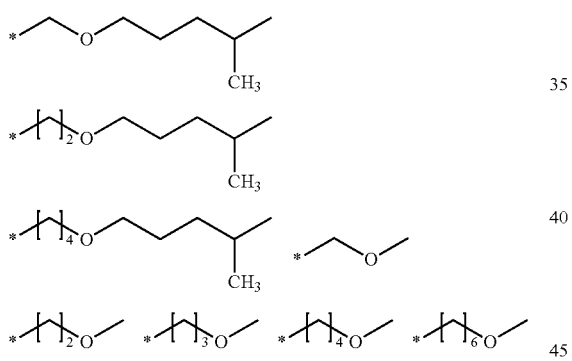

Examples of the group represented by the formula (L1-3) include the following ones.

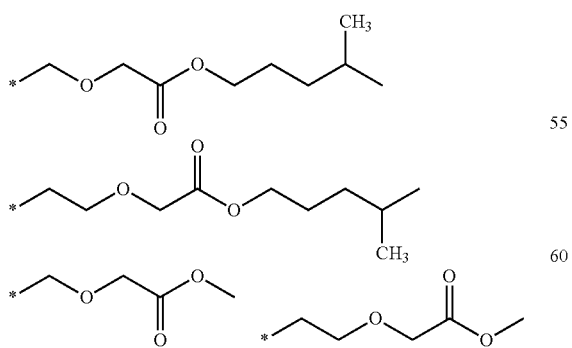

Examples of the group represented by the formula (L1-4) include the following ones.

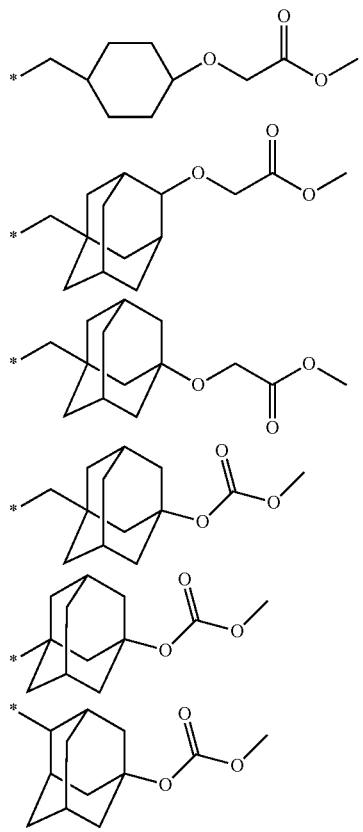

$L^{51}$ is preferably a single bond, the $C_1$ to $C_8$ divalent saturated hydrocarbon group or the group represented by the formula (L1-1), more preferably a single bond, the $C_1$ to $C_6$ divalent saturated hydrocarbon group or the group represented by the formula (L1-1).

Examples of the structural unit (a5-1) include the following ones.

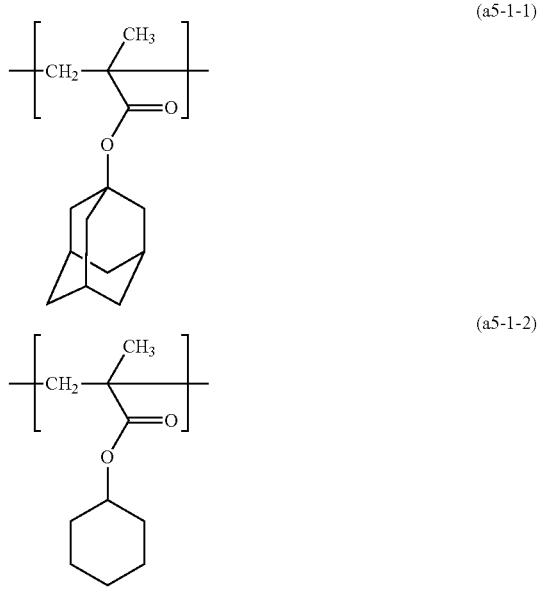

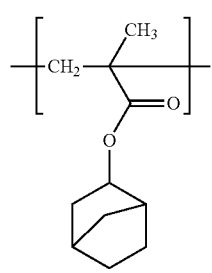 (a5-1-3)
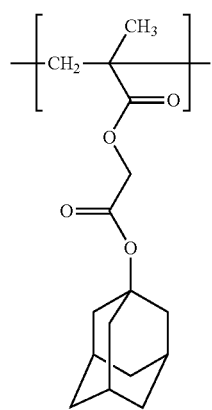 (a5-1-4)
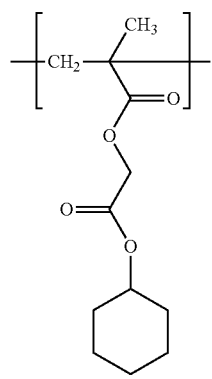 (a5-1-5)
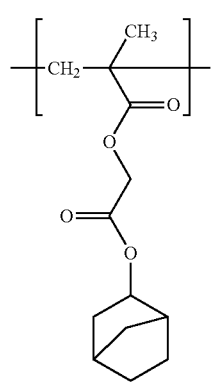 (a5-1-6)
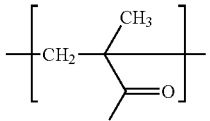 (a5-1-7)
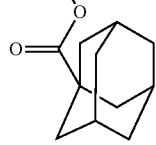 (a5-1-8)
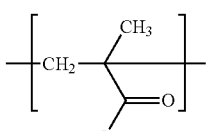 (a5-1-9)
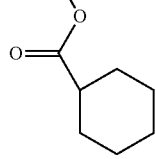 (a5-1-10)

(a5-1-11) 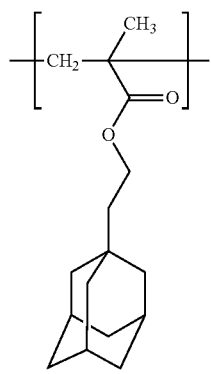

(a5-1-12) 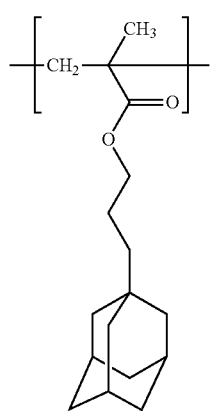

(a5-1-13) 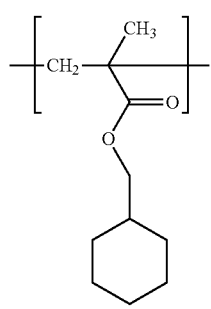

(a5-1-14) 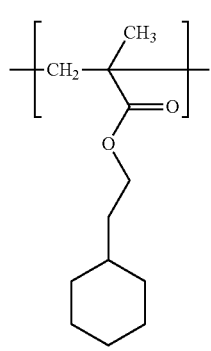

(a5-1-15) 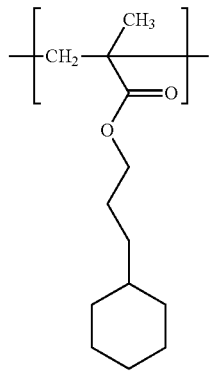

(a5-1-16) 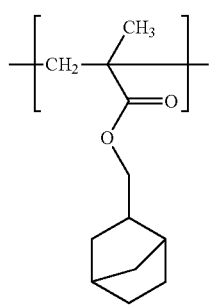

(a5-1-17) 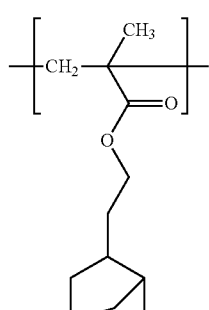

(a5-1-18) 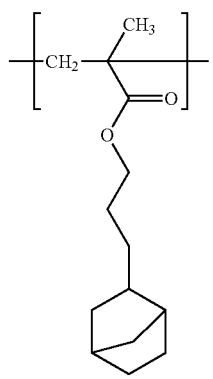

Examples of the structural units (a5) include those represented by the above formulae in which a methyl group corresponding to $R^{51}$ in the formula (a4-4) has been replaced by a hydrogen atom.

When the resin (A) further has the structural unit (a5), the proportion thereof is preferably 1 to 30% by mole, more preferably 2 to 20% by mole, and still more preferably 3 to 15% by mole, with respect to the total structural units (100% by mole) of the resin (A).

The resin (A) is preferably a resin having the structural unit (I), the structural unit (a1) and the structural unit (s), that is, a copolymer of the salt (I), the monomer (a1) and the monomer (s).

In this copolymer, the structural unit (a1) is preferably at least one of the structural unit (a1-0), the structural unit (a1-1), the structural unit (a1-2) (preferably the structural unit having a cyclohexyl group or a cyclopentyl group) and the structural unit (a1-5), and more preferably is the structural unit (a1-1) or the structural unit (a1-2) (preferably the structural unit having a cyclohexyl group or a cyclopentyl group).

The structural unit (s) is preferably at least one of the structural unit (a2) and the structural unit (a3). The structural unit (a2) is preferably the structural unit represented by the formula (a2-1). The structural unit (a3) is preferably the structural unit having at least one of the structural unit (a3-1), the structural unit (a3-2) and the structural unit (a3-4).

The proportion of the structural unit derived from the monomer having an adamantyl group (in particular, the structural unit (a1-1)) in the resin (A) is preferably 15% by mole or more with respect to the structural units (a1). As the mole ratio of the structural unit derived from the monomer having an adamantyl group increases within this range, the dry etching resistance of the resulting resist improves.

The resin (A) can be produced by a known polymerization method, for example, radical polymerization method, using one or more species of monomers inducing the structural units as described above. The proportion of the structural unit in the resin (A) can be adjusted by changing the amount of a monomer used in polymerization.

The weight average molecular weight of the resin (A) is preferably 2,000 or more (more preferably 2,500 or more, and still more preferably 3,000 or more), and 50,000 or less (more preferably 30,000 or less, and still more preferably 15,000 or less). In the present specification, the weight average molecular weight is a value determined by gel permeation chromatography using polystyrene as the standard product. The detailed condition of this analysis is described in Examples.

<Resin Other than Resin (A)>

The resist composition of the present disclosure may further contain a resin other than the resin (A). Examples of the resin include a resin consisting of the structural unit (s) and a resin having the structural unit (a4) (which is sometimes referred to as "resin (X)").

In the resin (X), the proportion of the structural unit (a4) is preferably 40% by mole or more, and more preferably 45% by mole or more, and still more preferably 50% by mole or more, with respect to the total structural units (100% by mole) constituting the resin (X).

The resin (X) may further have the structural unit (a2), the structural unit (a3) and the structural unit derived from the known monomer in this art.

The weight average molecular weight of the resin (X) is preferably 6,000 or more (more preferably 7,000 or more), and 80,000 or less (more preferably 60,000 or less).

When the resist composition contain the resin (X), the proportion thereof is preferably 1 to 60 parts by mass, more preferably 1 to 50 parts by mass, preferably 1 to 40 parts by mass, and more preferably 2 to 30 parts by mass, with respect to the resin (A) (100 parts by mass).

The total amount of the solid components in the resist composition may be only the resin (A), or the resin (A) and the resins other than the resin (A). The total proportion of the resin (A) and the resin other than the resin (A) is preferably 80% by mass to 99% by mass, more preferably 90% by mass to 99% by mass, with respect to the total amount of solid components of the resist composition.

The proportion of the solid components in the resist composition and that of the resins in the solid components can be measured with a known analytical method such as liquid chromatography and gas chromatography.

<Solvent (E)>

The proportion of a solvent (E) is generally 90% by mass or more, preferably 92% by mass or more, and more preferably 94% by mass or more, and also preferably 99% by mass or less, and more preferably 99.9% by mass or less. The proportion of the solvent (E) can be measured with a known analytical method such as liquid chromatography and gas chromatography.

Examples of the solvent (E) include glycol ether esters such as ethylcellosolve acetate, methylcellosolve acetate and propyleneglycolmonomethylether acetate; glycol ethers such as propyleneglycolmonomethylether; esters such as ethyl lactate, butyl acetate, amyl acetate and ethyl pyruvate; ketones such as acetone, methyl isobutyl ketone, 2-heptanone and cyclohexanone; and cyclic esters such as γ-butyrolactone. These solvents may be used as a single solvent or as a mixture of two or more solvents.

<Quencher (C)>

The resist composition of the disclosure may further contain a quencher such as a basic nitrogen-containing organic compound and a salt which generates an acid weaker in acidity than an acid generated from the acid generator.

Examples of the quencher include a basic nitrogen-containing organic compound and a salt which generates an acid weaker in acidity than an acid generated from the acid generator (B).

Examples of the basic nitrogen-containing organic compound include an amine and ammonium salts.

Examples of the amine include an aliphatic amine and an aromatic amine. Examples of the aliphatic amine include a primary amine, secondary amine and tertiary amine. Specific examples of the amine include 1-naphtylamine, 2-naphtylamine, aniline, diisopropylaniline, 2-, 3- or 4-methylaniline, 4-nitroaniline, N-methylaniline, N,N-dimethylaniline, diphenylamine, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, ethylene diamine, tetramethylene diamine, hexamethylene diamine, 4,4'-diamino-1,2-diphenylethane, 4,4'-diamino-3,3'-dimethyldiphenylmethane, 4,4'-diamino-3,3'-diethyldiphenylmethane, 2,2'-methylenebisaniline, imidazole, 4-methylimidazole, pyridine, 4-methylpyridine, 1,2-di(2-pyridyl)ethane, 1,2-di(4-pyridyl)ethane, 1,2-di(2-pyridyl)ethene, 1,2-di(4-pyridyl)ethene, 1,3-di(4-pyridyl) propane, 1,2-di(4-pyridyloxy)ethane, di(2-pyridyl)ketone, 4,4'-dipyridyl sulfide, 4,4'-dipyridyl disulfide, 2,2'-dipyridylamine, 2,2'-dipicolylamine and bipyridine. Among these, diisopropylaniline is preferred, particularly 2,6-diisopropylaniline is more preferred.

Specific examples of the ammonium salt include tetramethylammonium hydroxide, tetraisopropylammonium hydroxide, tetrabutylammonium hydroxide, tetrahexylammonium hydroxide, tetraoctylammonium hydroxide, phenyltrimethyl ammonium hydroxide, 3-(trifluoromethyl)phenyltrimethylammonium hydroxide, tetra-n-butyl ammonium salicylate and choline.

The salt generating an acid which is lower in acidity than an acid generated from both the salt (I) and the acid generator (B) is sometimes referred to as "weak acid salt". The "acidity" can be represented by acid dissociation constant, pKa, of an acid generated from a weak acid salt.

Examples of the weak acid salt include a salt generating an acid of pKa represents generally more than −3, preferably −1 to 7, and more preferably 0 to 5.

Specific examples of the weak acid salt include the following salts, the salt of formula (D), and salts as disclosed in JP2012-229206A1, JP2012-6908A1, JP2012-72109A1, JP2011-39502A1 and JP2011-191745A1.

-continued

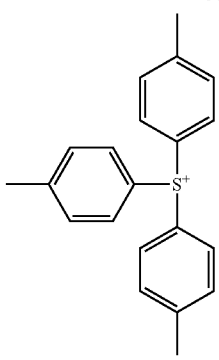

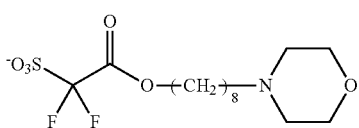

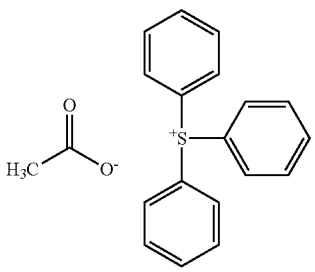

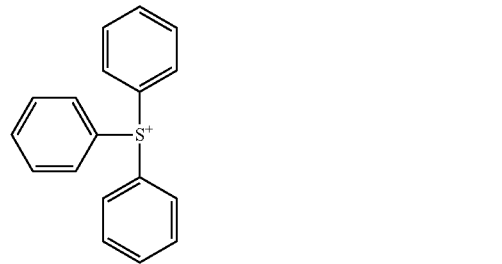

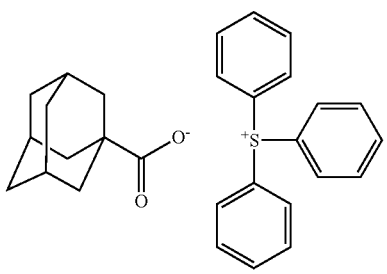

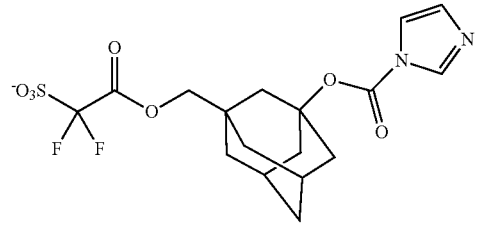

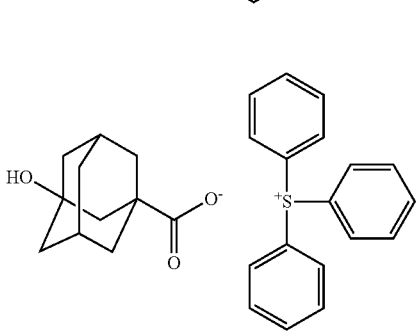

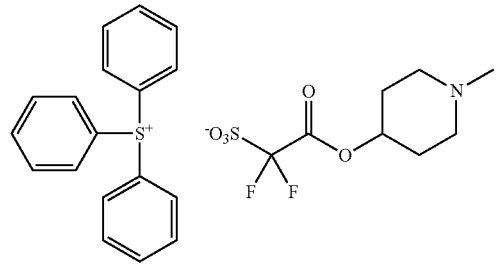

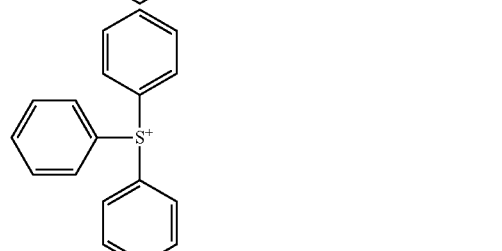

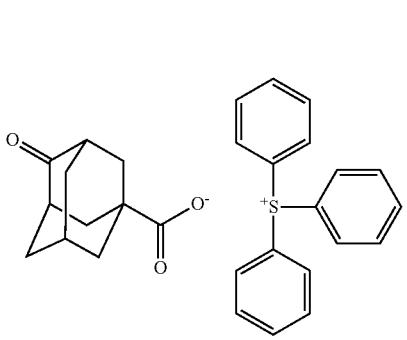

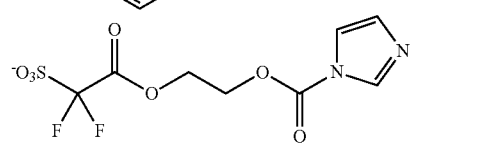

-continued

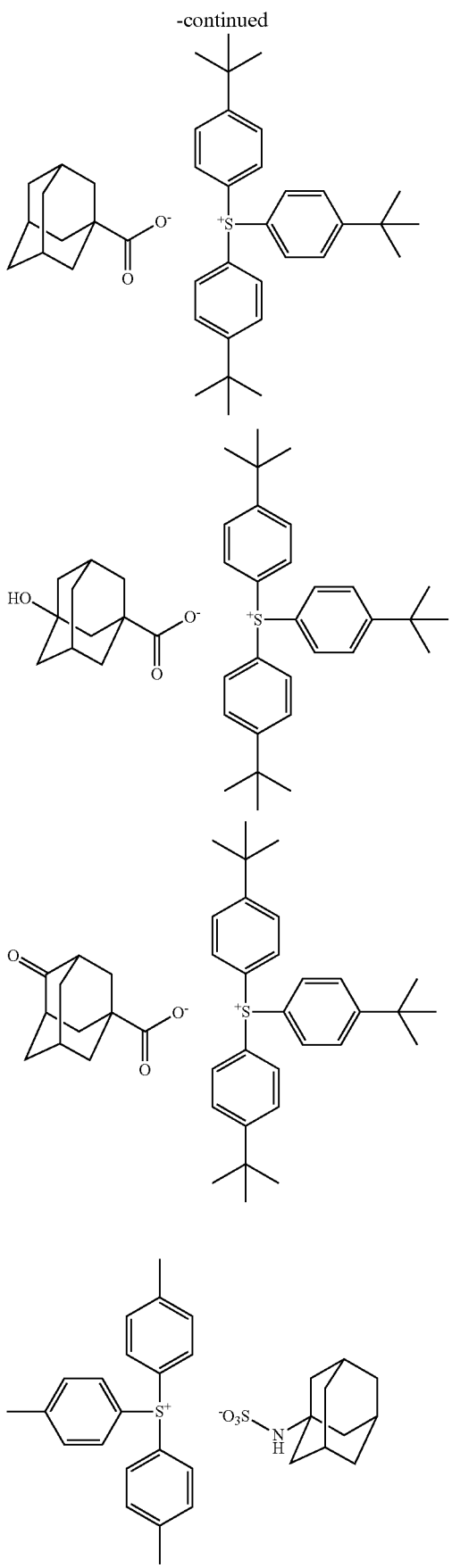

-continued

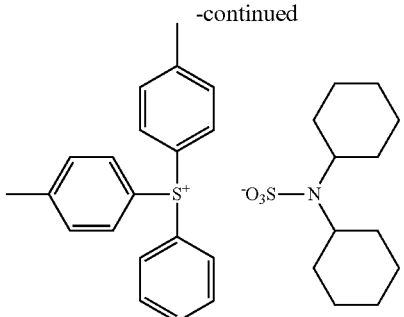

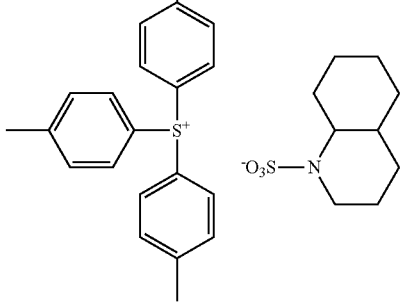

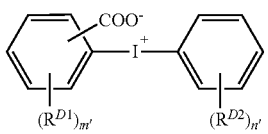

(D)

In the formula (D), $R^{D1}$ and $R^{D2}$ in each occurrence independently represent a $C_1$ to $C_{12}$ hydrocarbon group, a $C_1$ to $C_6$ alkoxyl group, a $C_2$ to $C_7$ acyl group, a $C_2$ to $C_7$ acyloxy group, a $C_2$ to $C_7$ alkoxycarbonyl group, a nitro group or a halogen atom; and m' and n' each independently represent an integer of 0 to 4.

Examples of the hydrocarbon group for $R^{D1}$ and $R^{D2}$ include any of an aliphatic hydrocarbon group, an alicyclic hydrocarbon group, an aromatic hydrocarbon group and a combination thereof.

Examples of the aliphatic hydrocarbon group include an alkyl group such as methyl, ethyl, propyl, isopropyl, butyl, isobutyl, tert-butyl, pentyl, hexyl and nonyl groups.

The alicyclic hydrocarbon group is any one of monocyclic or polycyclic hydrocarbon group, and saturated or unsaturated hydrocarbon group. Examples thereof include a cycloalkyl group such as cyclopropyl, cyclobutyl, cyclopentyl, cyclohexyl, cyclononyl and cyclododecyl groups; adamantyl and norbornyl groups.

Examples of the aromatic hydrocarbon group include an aryl group such as phenyl, 1-naphthyl, 2-naphthyl, 2-methylphenyl, 3-methylphenyl, 4-methylphenyl, 4-ethylphenyl, 4-propylphenyl, 4-isopropylphenyl, 4-butylphenyl, 4-tert-butylphenyl, 4-hexylphenyl, 4-cyclohexylphenyl, anthryl, p-adamantylphenyl, tolyl, xylyl, cumenyl, mesityl, biphenyl, phenanthryl, 2,6-diethylphenyl and 2-methyl-6-ethylphenyl groups.

Examples of the combination thereof include an alkyl-cycloalkyl, a cycloalkyl-alkyl, aralkyl (e.g., phenylmethyl, 1-phenylethyl, 2-phenylethyl, 1-phenyl-1-propyl, 1-phenyl-2-propyl, 2-phenyl-2-propyl, 3-phenyl-1-propyl, 4-phenyl-1-butyl, 5-phenyl-1-pentyl and 6-phenyl-1-hexyl groups) groups.

Examples of the alkoxyl group include methoxy and ethoxy groups.

Examples of the acyl group include acetyl, propanonyl, benzoyl and cyclohexanecarbonyl groups.

Examples of the acyloxy group include a group in which oxy group (—O—) bonds to an acyl group.

Examples of the alkoxycarbonyl group include a group in which the carbonyl group (—CO—) bonds to the alkoxy group.

Example of the halogen atom is a chlorine atom, a fluorine atom and bromine atom.

In the formula (D), $R^{D1}$ and $R^{D2}$ in each occurrence independently preferably represent a $C_1$ to $C_8$ alkyl group, a $C_3$ to $C_{10}$ cycloalkyl group, a $C_1$ to $C_6$ alkoxyl group, a $C_2$ to $C_4$ acyl group, a $C_2$ to $C_4$ acyloxy group, a $C_2$ to $C_4$ alkoxycarbonyl group, a nitro group or a halogen atom.

m' and n' independently preferably represent an integer of 0 to 3, more preferably an integer of 0 to 2, and more preferably 0.

Specific examples of the salt of the formula (D) include compounds below.

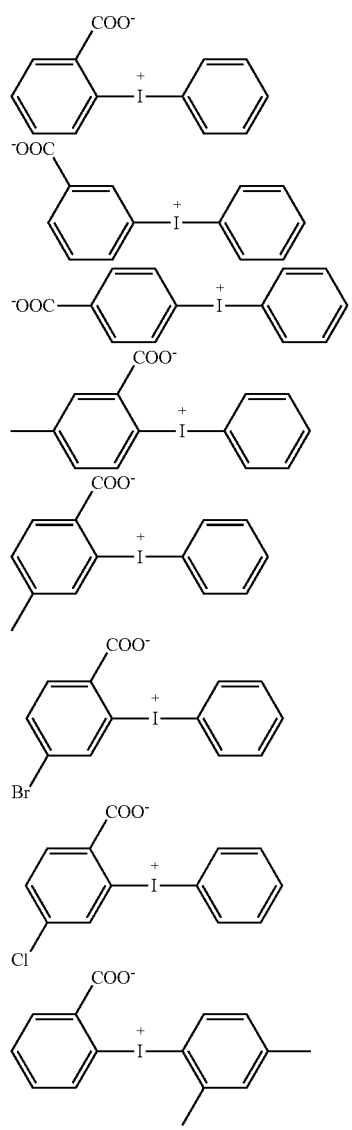

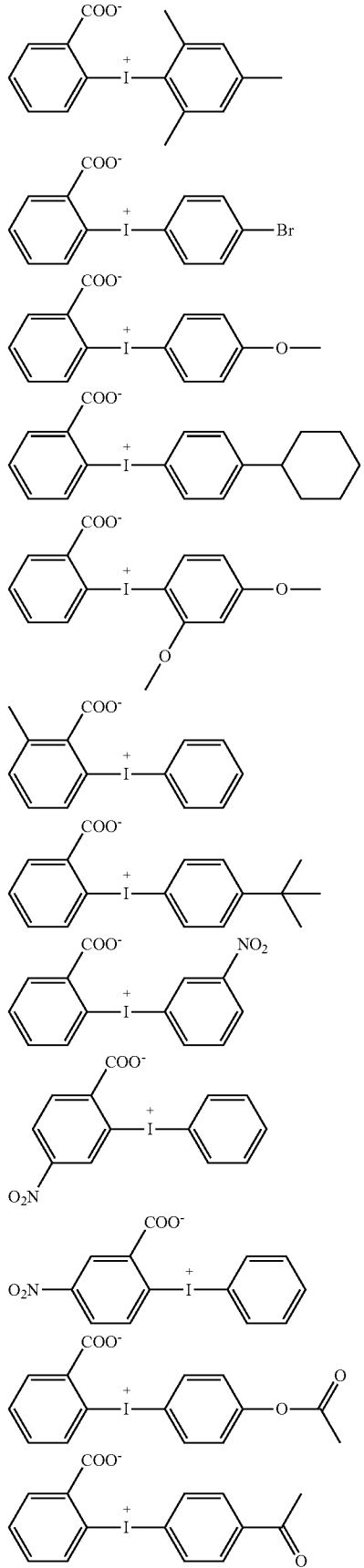

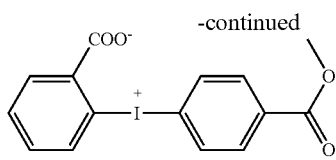

The salt of the formula (D) can be produced by a method described in "Tetrahedron Vol. 45, No. 19, p 6281-6296". Also, commercially available compounds can be used as the salt of the formula (D).

In the resist composition of the disclosure, the proportion of the quencher is preferably 0.01% by mass to 5% by mass, more preferably 0.01% by mass to 4% by mass, and still more preferably 0.01% by mass to 3% by mass with respect to total solid components of the resist composition.

<Other Ingredient>

The resist composition can further contain other ingredient (which is sometimes referred to as "other ingredient (F)"). Examples of the other ingredient (F) include various additives such as sensitizers, dissolution inhibitors, surfactants, stabilizers, and dyes, as needed.

<Preparing the Resist Composition>

The present resist composition can be prepared by mixing the salt (I) and the resin (A), together with the acid generator (B), the quencher (C), the solvent (E) and the other ingredient (F), as needed. There is no particular limitation on the order of mixing. The mixing may be performed in an arbitrary order. The temperature of mixing may be adjusted to an appropriate temperature within the range of 10 to 40° C., depending on the kinds of the resin and solubility in the solvent (E) of the resin. The time of mixing may be adjusted to an appropriate time within the range of 0.5 to 24 hours, depending on the mixing temperature. There is no particular limitation to the tool for mixing. An agitation mixing may be used.

After mixing the above ingredients, the present resist compositions can be prepared by filtering the mixture through a filter having about 0.003 to 0.2 μm pore diameter.

<Method for Producing Resist Pattern>

The method for producing a resist pattern of the disclosure includes the steps of:

(1) applying the resist composition of the disclosure onto a substrate;

(2) drying the applied composition to form a composition layer;

(3) exposing the composition layer;

(4) heating the exposed composition layer; and (5) developing the heated composition layer.

Applying the resist composition onto the substrate can generally be carried out through the use of a resist application device, such as a spin coater known in the field of semiconductor microfabrication technique. Examples of the substrate include inorganic substrates such as silicon wafer. The substrate may be washed, and an organic antireflection film may be formed on the substrate by use of a commercially available antireflection composition, before the application of the resist composition.

The solvent evaporates from the resist composition and a composition layer with the solvent removed is formed. Drying the applied composition layer, for example, can be carried out using a heating device such as a hotplate (so-called "prebake"), a decompression device, or a combination thereof. The temperature is preferably within the range of 50 to 200° C. The time for heating is preferably 10 to 180 seconds. The pressure is preferably within the range of 1 to $1.0 \times 10^5$ Pa.

The obtained composition layer is generally exposed using an exposure apparatus or a liquid immersion exposure apparatus. The exposure is generally carried out using with various types of exposure light source, such as irradiation with ultraviolet lasers, i.e., KrF excimer laser (wavelength: 248 nm), ArF excimer laser (wavelength: 193 nm), $F_2$ excimer laser (wavelength: 157 nm), irradiation with harmonic laser light of far-ultraviolet or vacuum ultra violet wavelength-converted laser light from a solid-state laser source (YAG or semiconductor laser or the like), or irradiation with electron beam or EUV or the like. In the specification, such exposure to radiation is sometimes referred to be collectively called as exposure. The exposure is generally carried out through a mask that corresponds to the desired pattern. When electron beam is used as the exposure light source, direct writing without using a mask can be carried out.

After exposure, the composition layer is subjected to a heat treatment (so-called "post-exposure bake") to promote the deprotection reaction. The heat treatment can be carried out using a heating device such as a hotplate. The heating temperature is generally in the range of 50 to 200° C., preferably in the range of 70 to 150° C.

The developing of the baked composition film is usually carried out with a developer using a development apparatus. Developing can be conducted in the manner of dipping method, paddle method, spray method and dynamic dispensing method. Temperature for developing is generally 5 to 60° C. The time for developing is preferably 5 to 300 seconds.

The photoresist pattern obtained from the photoresist composition may be a positive one or a negative one by selecting suitable developer.

The development for obtaining a positive photoresist pattern is usually carried out with an alkaline developer. The alkaline developer to be used may be any one of various alkaline aqueous solution used in the art. Generally, an aqueous solution of tetramethylammonium hydroxide or (2-hydroxyethyl)trimethylammonium hydroxide (commonly known as "choline") is often used. The surfactant may be contained in the alkaline developer.

After development, the resist pattern formed is preferably washed with ultrapure water, and the residual water remained on the resist film or on the substrate is preferably removed therefrom.

The development for obtaining a negative photoresist pattern is usually carried out with a developer containing an organic solvent. The organic solvent to be used may be any one of various organic solvents used in the art, examples of which include ketone solvents such as 2-hexanone, 2-heptanone; glycol ether ester solvents such as propyleneglycol-monomethylether acetate; ester solvents such as the butyl acetate; glycol ether solvents such as the propyleneglycol-monomethylether; amide solvents such as N,N-dimethylacetamide; aromatic hydrocarbon solvents such as anisole.

In the developer containing an organic solvent, the amount of organic solvents is preferably 90% by mass to 100% by mass, more preferably 95% by mass to 100% by mass of the developer. The developer still more preferably consists essentially of organic solvents.

Among these, the developer containing an organic solvent preferably contains butyl acetate and/or 2-heptanone. In the developer containing an organic solvent, the total amount of butyl acetate and 2-heptanone is preferably 50% by mass to 100% by mass of the developer, more preferably 90% by mass to 100% by mass of the developer. The developer still more preferably consists essentially of butyl acetate and/or 2-heptanone.

Developers containing an organic solvent may contain a surfactant. Also, the developer containing an organic solvent may include a little water.

The developing with a developer containing an organic solvent can be finished by replacing the developer by another solvent.

After development, the photoresist pattern formed is preferably washed with a rinse agent. Such rinse agent is not unlimited provided that it does not detract a photoresist pattern. Examples of the agent include solvents which contain organic solvents other than the above-mentioned developers, such as alcohol agents or ester agents.

After washing, the residual rinse agent remained on the substrate or photoresist film is preferably removed therefrom.

<Application>

The resist composition of the disclosure is useful for excimer laser lithography such as ArF, KrF, electron beam (EB) exposure lithography or extreme-ultraviolet (EUV) exposure lithography, and is more useful for ArF excimer laser exposure lithography.

The resist composition of the disclosure can be used in semiconductor microfabrication.

EXAMPLES

The disclosure will be described more specifically by way of examples, which are not construed to limit the scope of the disclosure.

All percentages and parts expressing the content or amounts used in the Examples and Comparative Examples are based on mass, unless otherwise specified.

The weight average molecular weight is a value determined by gel permeation chromatography.

Equipment: HLC-8120GPC type (Tosoh Co. Ltd.)
Column: TSK gel Multipore HXL-M×3+guardcolumn (Tosoh Co. Ltd.)
Eluent: tetrahydrofuran
Flow rate: 1.0 mL/min
Detecting device: RI detector
Column temperature: 40° C.
Injection amount: 100 μL
Standard material for calculating molecular weight: standard polystyrene (Tosoh Co. ltd.)

Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.). The value of the peak in the mass spectrometry is referred to as "MASS".

Example 1

Synthesis of the Salt Represented by the Formula (I-13)

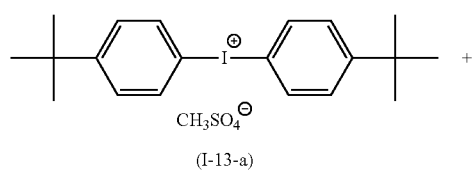

(I-13-a)

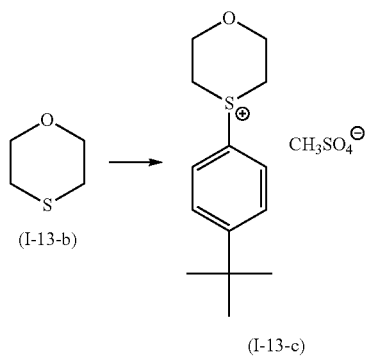

Into a reactor, 50 parts of the compound represented by the formula (I-13-a), 10.33 parts of the compound represented by the formula (I-13-b) and 350 parts of chloroform were charged, and then stirred at 23° C. for 30 minutes. To the obtained solution, 0.20 parts of copper (II) acetate was added, and refluxed at 80° C. for 2 hours, followed by being concentrated. To the obtained concentrate, 440 parts of tert-butylmethylether was added, stirred and filtrated to obtain 32.96 parts of the salt represented by the formula (I-13-c).

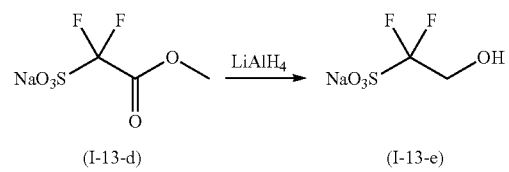

Into 10 parts of tetrahydrofuran, 2.21 parts of lithium aluminium hydride was added at 5° C., and stirred at 5° C. for 30 minutes. To the obtained mixture, a mixture solution of 8.22 parts of the compound represented by the formula (I-13-d) and 30 part of tetrahydrofuran was dropped for 1 hour, and stirred at 23° C. for 18 hours. To the reaction mixture, 30 parts of hydrochloric acid was added and concentrated. The obtained concentrate, 82 parts of acetonitrile was added, stirred, and filtrate. The obtained filtrate was concentrated to obtain 6.28 parts of the compound represented by formula (I-13-e).

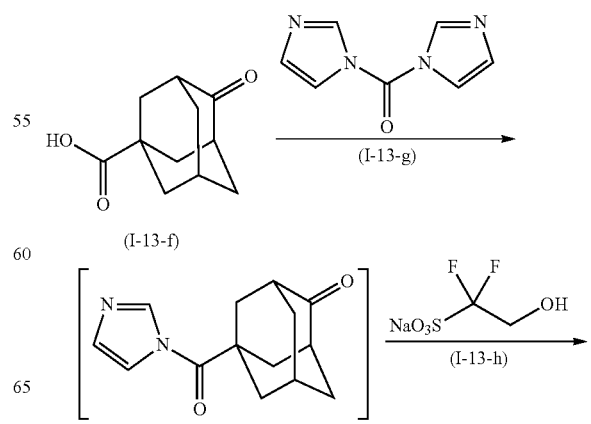

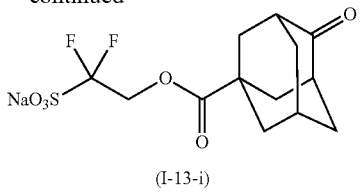

(I-13-i)

13.25 Parts of the compound represented by the formula (I-13-f) and 40 parts of acetonitrile were mixed, and stirred at 23° C. for 30 minutes. To the mixture solution, 11.63 parts of the compound represented by the formula (I-13-g) was added, and stirred at 40° C. for 1 hour. To the obtained reaction mass, a mixture solution of 6.28 parts of the compound represented by the formula (I-13-h) and 13.20 parts of acetonitrile was added, and stirred at 23° C. for 16 hours. To the obtained reaction mixture, 30 parts of acetonitrile was added, stirred and filtrated. The obtained filtrate was concentrated to obtain 9.06 parts of the compound represented by formula (I-13-i).

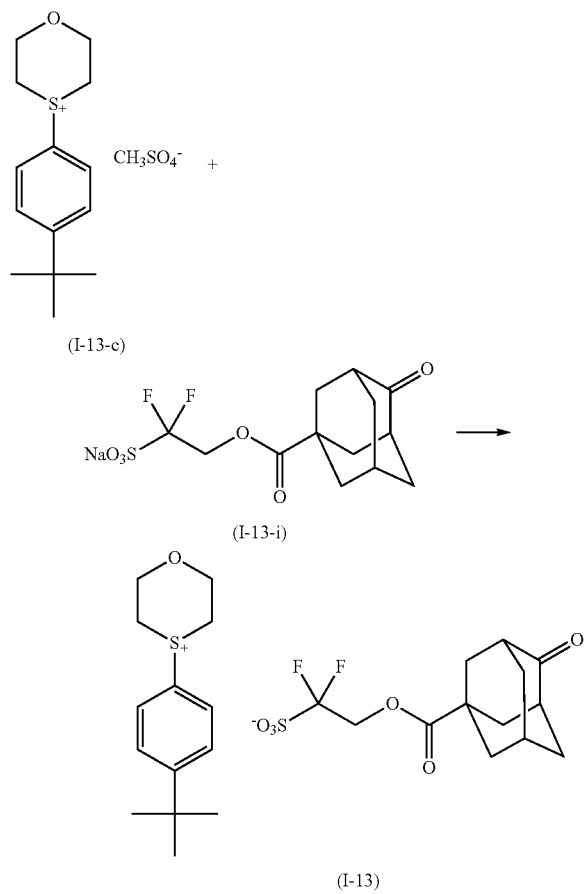

9.06 Parts of the compound represented by the formula (I-13-i), 11.89 parts of the compound represented by the formula (I-13-c), 20 parts of acetonitrile, 63 parts of chloroform and 31.44 parts of 5% aqueous oxalic acid solution were mixed, and stirred at 23° C. for 2 hours. The obtained reaction solution was separated. To the obtained organic layer, 21 parts of 5% aqueous oxalic acid solution was added, stirred at 23° C. for 30 minutes, followed by separating an organic layer. The washing step with water was conducted three times. To the obtained organic layer, 21 parts of 5% aqueous sodium hydrogen carbonate solution was added, and stirred at 23° C. for 30 minutes, followed by separating an organic layer. The washing step with water was conducted twice. To the obtained organic layer, 21 parts of ion-exchanged water was added, stirred at 23° C. for 30 minutes, followed by separating an organic layer. The washing step with water was conducted three times. The washed organic layer was concentrated. To the concentrate mass, 80 parts of acetonitrile and 60 parts of ethyl acetate were added, stirred, and filtrated to obtain 4.53 parts of the salt represented by the formula (I-13).

MASS (ESI (+) Spectrum): M$^+$ 237.1

MASS (ESI (−) Spectrum): M$^-$ 337.1

Example 2

Synthesis of the Salt Represented by the Formula (I-14)

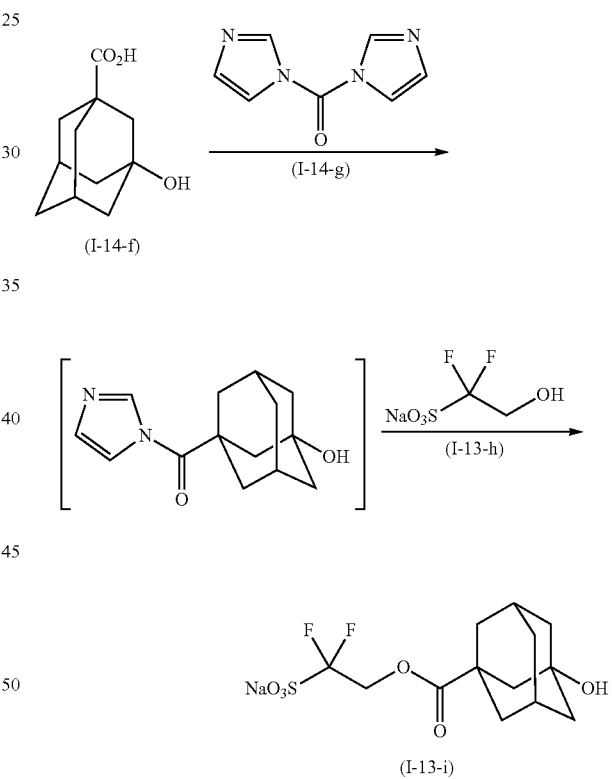

8.01 Parts of the compound represented by the formula (I-14-f) and 28.06 parts of acetonitrile were mixed, and stirred at 23° C. for 30 minutes. To the mixture solution, 6.96 parts of the compound represented by the formula (I-14-g) was added, and stirred at 50° C. for 6 hours. To the obtained reaction mass, a mixture solution of 3.76 parts of the compound represented by the formula (I-13-h) and 8.24 parts of acetonitrile was added, and stirred at 23° C. for 18 hours. To the obtained reaction mixture, 30 parts of acetonitrile was added, stirred and filtrated. The obtained filtrate was concentrated to obtain 4.93 parts of the compound represented by formula (I-14-i).

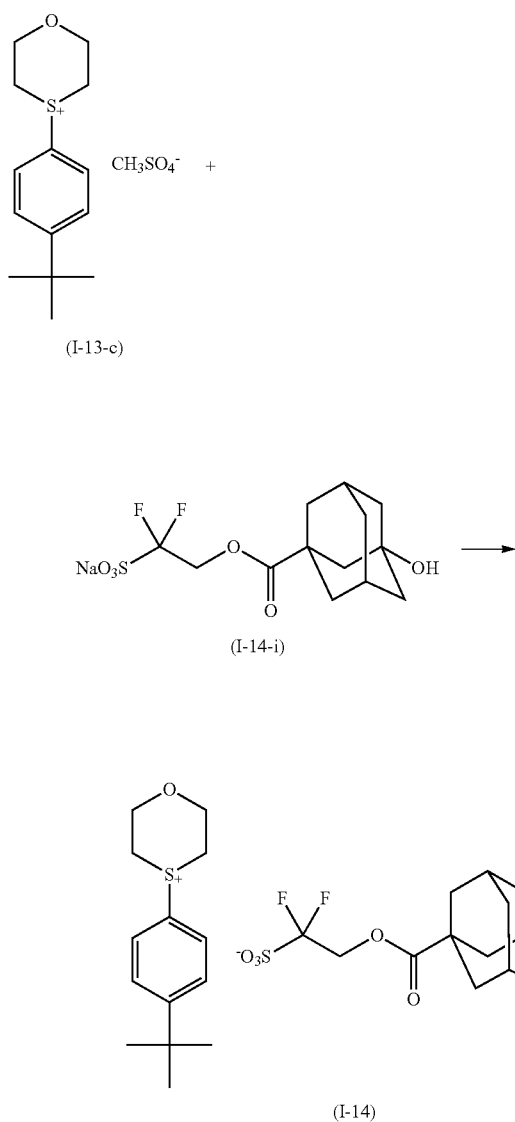

(I-13-c)

(I-14-i)

(I-14)

4.93 Parts of the compound represented by the formula (I-14-i), 7.16 parts of the compound represented by the formula (I-13-c), 7.50 parts of acetonitrile, 50 parts of chloroform and 24.38 parts of 5% aqueous oxalic acid solution were mixed, and stirred at 23° C. for 2 hours. The obtained reaction solution was separated. To the obtained organic layer, 16 parts of 5% aqueous oxalic acid solution was added, stirred at 23° C. for 30 minutes, followed by separating an organic layer. To the obtained organic layer, 16 parts of 5% aqueous sodium hydrogen carbonate solution was added, and stirred at 23° C. for 30 minutes, followed by separating an organic layer. To the obtained organic layer, 16 parts of ion-exchanged water was added, stirred at 23° C. for 30 minutes, followed by separating an organic layer. The washing step with water was conducted five times. The washed organic layer was concentrated. To the concentrate mass, 5.5 parts of acetonitrile and 19.5 parts of ethyl acetate were added, stirred, and filtrated to obtain 0.65 parts of the salt represented by the formula (I-14).

MASS (ESI (+) Spectrum): M$^+$ 237.1

MASS (ESI (−) Spectrum): M$^-$ 339.1

Example 3

Synthesis of the Salt Represented by the Formula (I-15)

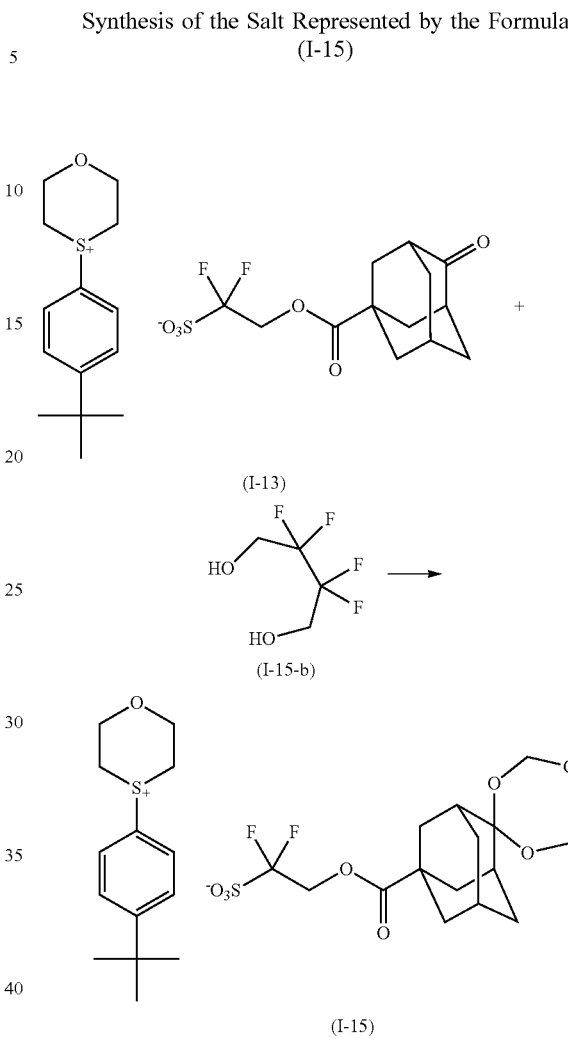

(I-13)

(I-15-b)

(I-15)

1.73 Parts of the compound represented by the formula (I-13-a), 0.73 parts of the compound represented by the formula (I-15-b) and 10 parts of 1,2-dichloroethane were mixed, and stirred at 23° C. for 30 minutes. To the obtained mixture solution, 0.01 parts of p-toluenesulfonic acid was added, and refluxed with being stirred at 100° C. for 3 hours. The obtained reaction mixture was cooled at 23° C., and 30 parts of chloroform and 10 parts of 5% aqueous sodium hydrogen carbonate solution were added thereto, stirred at 23° C. for 30 minutes, and left still, followed by separating an organic layer. To the obtained organic layer, 10 parts of ion-exchanged water was added, and stirred at 23° C. for 30 minutes, followed by separating an organic layer. The washing step with water was conducted seven times. To the obtained organic layer, 1.00 parts of activated carbon was added and stirred at 23° C. for 30 minutes, followed by being filtrated. The obtained filtrate was concentrated, and tert-butylmethylether was added thereto and stirred, followed by being filtrated to obtain 1.28 parts of the salt represented by the formula (I-15).

MASS (ESI (+) Spectrum): M$^+$ 237.1

MASS (ESI (−) Spectrum): M$^-$ 481.1

Example 4

Synthesis of the Salt Represented by the Formula (I-57)

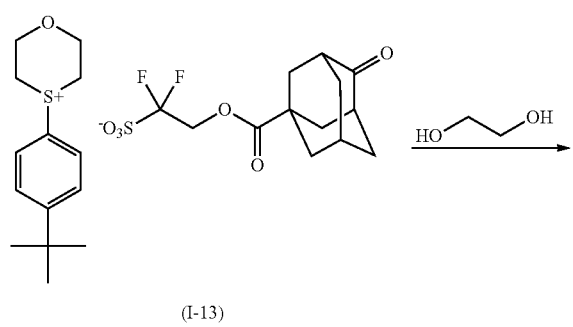

(I-13)

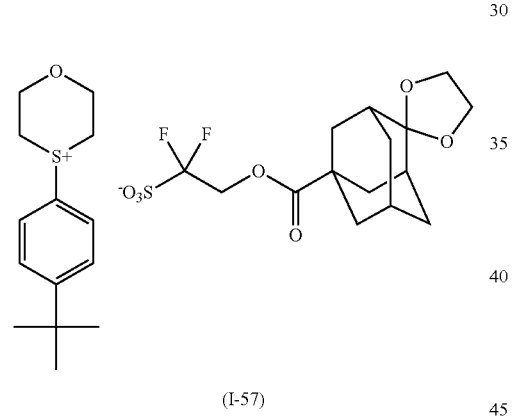

(I-57)

In a reactor, 1.96 parts of the salt represented by the formula (I-13) and 10 parts of ethyleneglycole were mixed and stirred at 23° C. for 30 minutes, and raised temperature to 103° C. To the obtained mixture, 0.02 parts of sulfonic acid was added, and stirred at 103° C. for 1 hour. The obtained reaction mixture was cooled at 23° C., and 20 parts of chloroform and 10 parts of ion-exchanged water were added thereto, stirred at 23° C. for 30 minutes, followed by separating an organic layer. The washing step with water was conducted three times. The obtained organic layer was concentrated, and 10 parts of acetonitrile was added thereto and stirred at 23° C. for 30 minutes, followed by being concentrated. To the concentrate, 10 parts of ethyl acetate was added, and stirred at 23° C. for 30 minutes, then the obtained supernatant thereof was removed therefrom. The obtained residue was concentrated to obtain 1.84 parts of the salt represented by the formula (I-57).

MASS (ESI (+) Spectrum): M⁺ 237.1

MASS (ESI (−) Spectrum): M⁻ 381.1

Example 5

Synthesis of the Salt Represented by the Formula (I-75)

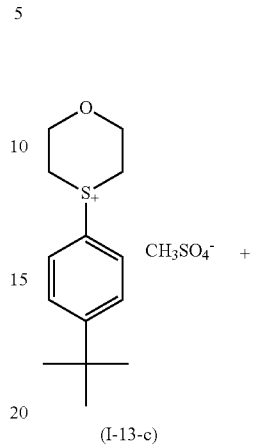

(I-13-c)

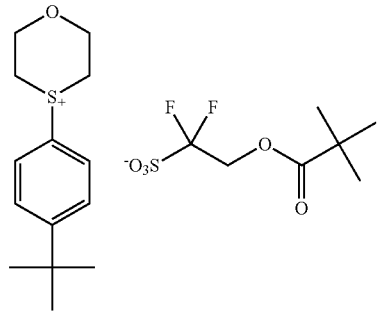

(I-75-a)

(I-75)

10.00 Parts of the salt represented by the formula (I-75-a), 10.57 parts of the compound represented by the formula (I-13-c), 50 parts of chloroform and 25 parts of 5% aqueous oxalic acid solution were mixed, and stirred at 23° C. for 2 hours. 10 parts of acetonitrile was added to the obtained reaction solution and followed by separating an organic layer. To the obtained organic layer, 25 parts of ion exchanged water was added, stirred at 23° C. for 30 minutes, followed by separating an organic layer. The washing step with water was conducted five times. The washed organic layer was concentrated. To the concentrate mass, 30 parts of acetonitrile and 50 parts of tert-butyl methyl ether were added, stirred, and filtrated to obtain 10.25 parts of the salt represented by the formula (I-75).

MASS (ESI (+) Spectrum): M⁺ 237.1

MASS (ESI (−) Spectrum): M⁻ 245.0

Synthesis Example 1

Synthesis of the Salt Represented by Formula (B1-21)

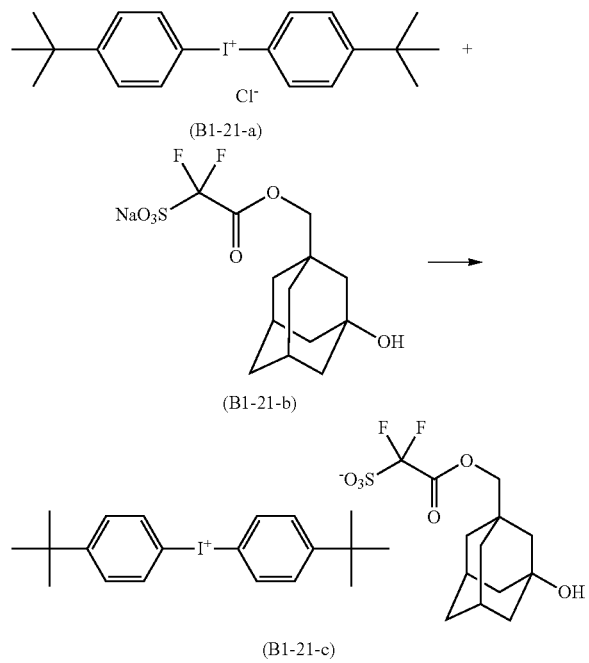

The compound represented by the formula (B1-21-b) was produced according to a method recited in JP2008-209917A1.

Into a reactor, 30.00 parts of the compound represented by the formula (B1-21-b) and 35.50 parts of the salt represented by the formula (B1-21-a), 100 parts of chloroform and 50 parts of ion-exchanged water were charged and stirred at 23° C. for about 15 hours. From the obtained solution which had two layers, a chloroform layer was collected and then 30 parts of ion-exchanged water was added thereto for washing. These steps were conducted five times. Then the washed layer was concentrated, and then, 100 parts of tert-butyl methyl ether was added to the obtained residues and the obtained mixture was stirred at 23° C. for about 30 minutes. The resulting mixture was filtrated to obtain 48.57 parts of the salt represented by the formula (B1-21-c).

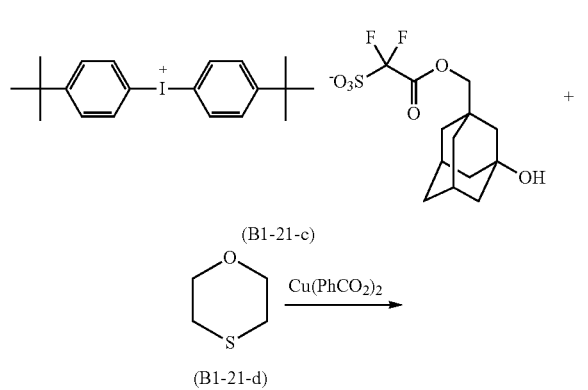

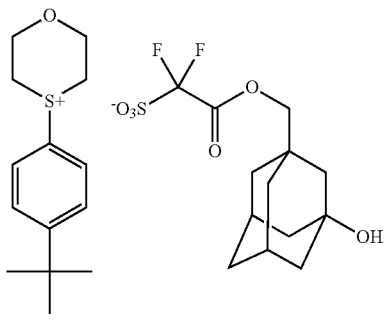

Into a reactor, 20.00 parts of the salt represented by the formula (B1-21-c), 2.84 parts of the compound represented by the formula (B1-21-d) and 250 parts of monochlorobenzene were charged and stirred at 23° C. for 30 minutes. To the resulting mixture, 0.21 parts of copper (II) dibenzoate was added and the obtained mixture was stirred at 100° C. for 1 hour. The reaction mixture was concentrated, and then, 200 parts of chloroform and 50 parts of ion-exchanged water were added to the obtained residues and the obtained mixture was stirred at 23° C. for 30 minutes, followed by separating an organic layer. 50 parts of ion-exchanged water was added to the obtained organic layer, and the obtained mixture was stirred at 23° C. for 30 minutes, followed by separating an organic layer. The washing step with water was conducted five times. The obtained organic layer was concentrated, and then the obtained residues were dissolved in 53.51 parts of acetonitrile. Then the mixture was concentrated, and 113.05 parts of tert-butyl methyl ether was added thereto and the obtained mixture was stirred, followed by filtrating it to obtain 10.47 parts of the salt represented by the formula (B1-21).

MASS (ESI (+)Spectrum): M+237.1

MASS (ESI (−)Spectrum): M− 339.1

Synthesis Example 2

Synthesis of the Salt Represented by Formula (B1-22)

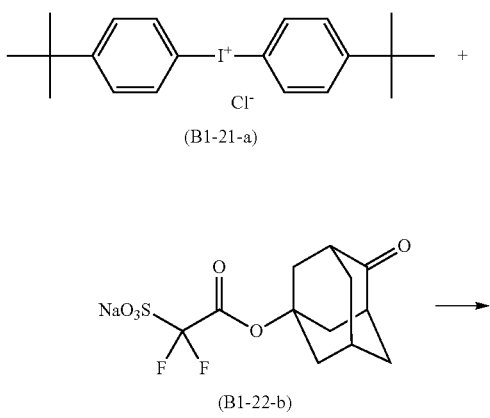

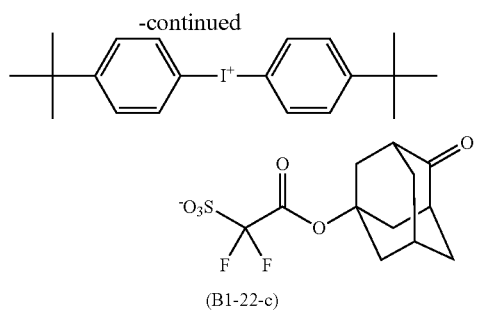

Into a reactor, 11.26 parts of the salt represented by the formula (B1-21-a), 10 parts of the compound represented by the formula (B1-22-b), 50 parts of chloroform and 25 parts of ion-exchanged water were charged and stirred at 23° C. for about 15 hours. From the obtained solution which had two layers, a chloroform layer was collected and then 15 parts of ion-exchanged water were added thereto for washing. These steps were conducted five times. Then the washed layer was concentrated, and then 50 parts of tert-butyl methyl ether was added to the obtained residues, and the obtained mixture was stirred at 23° C. for about 30 minutes. The resulting mixture was filtrated to obtain 11.75 parts of the salt represented by the formula (B1-22-c).

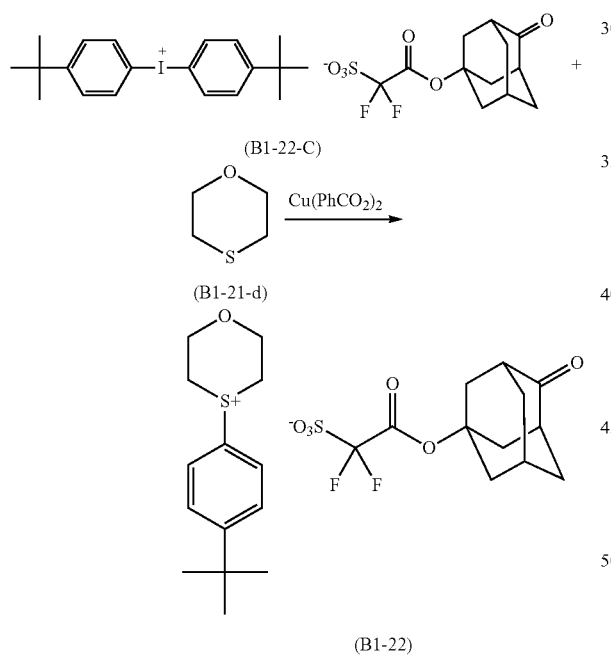

Into a reactor, 11.71 parts of the salt represented by the formula (B1-22-c), 1.70 parts of the compound represented by the formula (B1-21-d) and 46.84 parts of monochlorobenzene were charged and stirred at 23° C. for 30 minutes. To the resulting mixture, 0.12 parts of copper (II) dibenzoate was added and the obtained mixture was stirred at 100° C. for 30 minutes. The reaction mixture was concentrated, and then 50 parts of chloroform and 12.50 parts of ion-exchanged water were added to the obtained residues, and the obtained mixture was stirred at 23° C. for 30 minutes, followed by separating an organic layer. 12.50 parts of ion-exchanged water was added to the obtained organic layer and the obtained mixture was stirred at 23° C. for 30 minutes, followed by separating an organic layer to wash with water. The washing step with water was conducted eight times. Then the obtained organic layer was concentrated, and 50 parts of tert-butyl methyl ether were added thereto and the obtained mixture was stirred, followed by filtrating it to obtain 6.84 parts of the salt represented by the formula (B1-22).

MASS (ESI (+)Spectrum): $M^+$ 237.1

MASS (ESI (−)Spectrum): $M^-$ 323.0

Synthesis Example 3

Synthesis of the Salt Represented by Formula (B1-X)

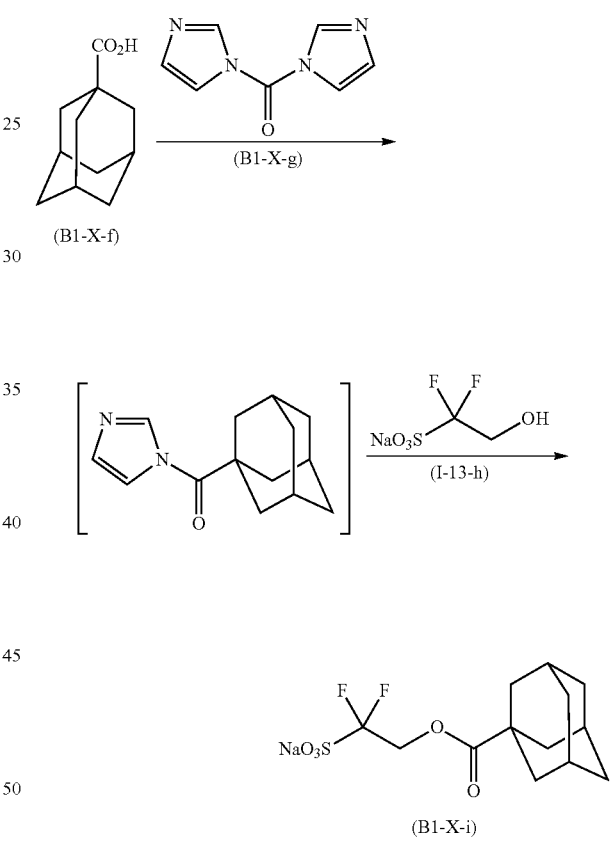

Into a reactor, 7.36 parts of the compound represented by the formula (B1-X-f) and 28 parts of acetonitrile were charged and stirred at 23° C. for about 30 minutes. To the obtained mixture solution, 6.96 parts of the compound represented by the formula (B1-X-g) was added and stirred at 50° C. for about 6 hours. To the resulting reaction mass, a mixture solution of 3.76 parts of the compound represented by the formula (I-13-h) and 8.24 parts of acetonitrile was added and stirred at 23° C. for 18 hours. The obtained reaction mass, 30 parts of acetonitrile was added and stirred, followed by filtrating. The obtained filtrate was concentrated to obtain 4.76 parts of the compound represented by the formula (B1-X-i).

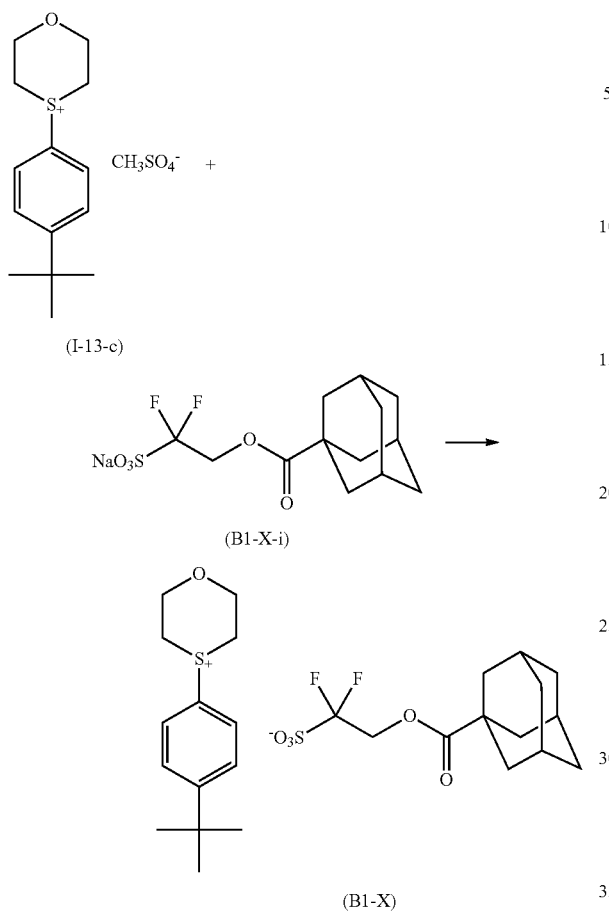

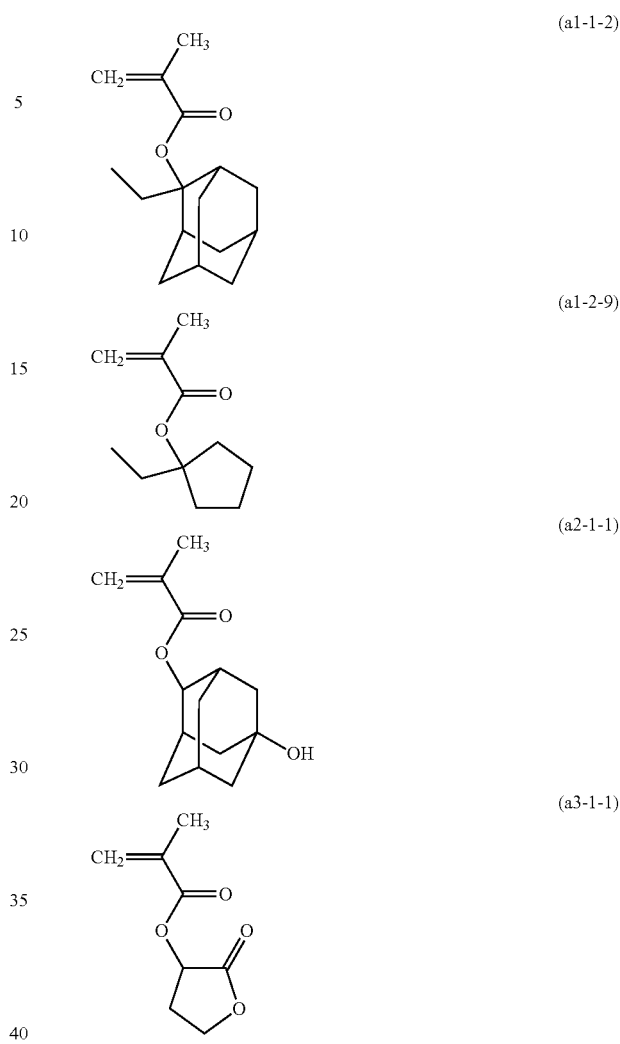

4.71 Parts of the compound represented by the formula (B1-X-i), 7.16 parts of the compound represented by the formula (I-13-c), 7.50 parts of acetonitrile, 50 parts of chloroform and 24.38 parts of 5% aqueous oxalic acid solution were mixed, and stirred at 23° C. for 2 hours. The obtained reaction solution was separated. To the obtained organic layer, 16 parts of 5% aqueous sodium hydrogen carbonate solution was added, stirred at 23° C. for 30 minutes, followed by separating an organic layer. To the obtained organic layer, 16 parts of ion-exchanged water was added, stirred at 23° C. for 30 minutes, followed by separating an organic layer. The washing step with water was conducted five times. The washed organic layer was concentrated. To the concentrate mass, 5 parts of acetonitrile and 20 parts of ethyl acetate were added, stirred, and filtrated to obtain 1.18 parts of the salt represented by the formula (B1-X).

MASS (ESI (+) Spectrum): M$^+$ 237.1

MASS (ESI (−) Spectrum): M$^-$ 323.1

Synthesis Examples of Resins

The monomers used for Synthesis Examples of the resins are shown below. These monomers are referred to as "monomer (X)" where "(X)" is the symbol of the formula representing the structure of each monomer.

Synthesis Example 4

Synthesis of Resin A1

Monomer (a1-1-2), monomer (a1-2-9), monomer (a2-1-1) and monomer (a3-1-1) were mixed together with a mole ratio of monomer (a1-1-2), monomer (a1-2-9), monomer (a2-1-1) and monomer (a3-1-1)=5:42:32:21, and propyleneglycolmonomethylether acetate was added thereto in the amount equal to 2 times by mass of the total amount of monomers to obtain a solution. Azobisisobutyronitrile and azobis(2,4-dimethylvaleronitrile) were added as initiators to the solution in the amounts of 1% by mole and 3% by mole respectively with respect to the total amount of monomers, and the resultant mixture was heated for about 5 hours at 75° C. Then, the obtained reaction mixture was poured into a large amount of a mixture of methanol and water to precipitate a resin. The obtained resin was filtrated. The obtained resin was dissolved in propyleneglycolmonomethylether acetate to obtain a solution, and the solution was poured into a mixture of methanol and water to precipitate the resin. The obtained resin was filtrated. These operations were conducted twice to obtain the copolymer having the weight average molecular weight of about 9100 in 97% yield. This resin, which had the structural units of the following formulae, was referred to as Resin A1.

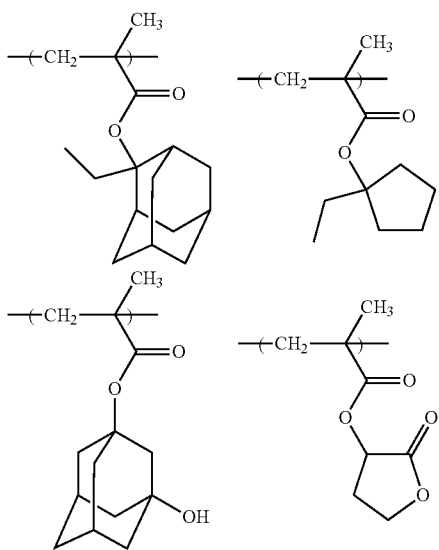

(Preparing Resist Compositions)

Resist compositions were prepared by mixing and dissolving each of the components shown in Table 2, and then filtrating through a fluororesin filter having 0.2 µm pore diameter.

1-57: Salt represented by the formula (1-57)
1-75: Salt represented by the formula (1-75)
<Acid Generator (B)>
B1-21: Salt represented by the formula (B1-21)
B1-22: Salt represented by the formula (B1-22)
B1-X: Salt represented by the formula (B1-X1)
<Quencher (C)>
D1: Compound as follow, a product of Tokyo Chemical Industry Co., LTD

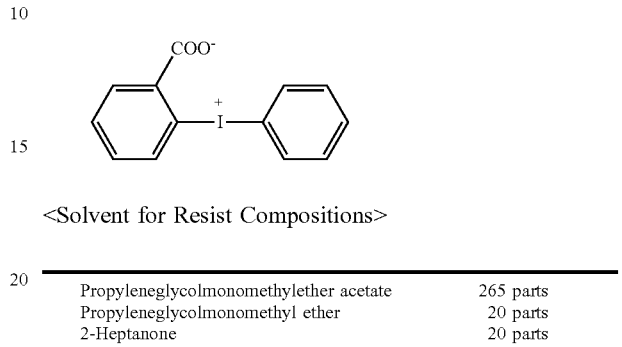

<Solvent for Resist Compositions>

| Propyleneglycolmonomethylether acetate | 265 parts |
| Propyleneglycolmonomethyl ether | 20 parts |
| 2-Heptanone | 20 parts |
| γ-butyrolactone | 3.5 parts |

<Evaluation of Resist Compositions>

A silicon wafer on which a 100 nm-thick $SiO_2$ layer was formed was treated with hexamethyldisilazane at 120° C. for 60 seconds.

One of the resist compositions was then applied thereon by spin coating in such a manner that the thickness of the film after drying (pre-baking) became 240 nm.

TABLE 2

| Resist Comp. | Resin (parts) | Salt (I) (parts) | Acid Generator (B) (parts) | Quencher (C) (parts) | PB/PEB (° C./° C.) |
|---|---|---|---|---|---|
| Composition 1 | A1 = 10 | I-13 = 1.0 | — | D1 = 0.2 | 90/85 |
| Composition 2 | A1 = 10 | I-14 = 1.0 | — | D1 = 0.2 | 90/85 |
| Composition 3 | A1 = 10 | I-15 = 1.0 | — | D1 = 0.2 | 90/85 |
| Composition 4 | A1 = 10 | I-13 = 0.4 | B1-21 = 0.6 | D1 = 0.2 | 90/85 |
| Composition 5 | A1 = 10 | I-14 = 0.4 | B1-21/B1-22 = 0.2/0.4 | D1 = 0.2 | 90/85 |
| Composition 6 | A1 = 10 | I-14 = 0.6 | B1-22 = 0.4 | D1 = 0.2 | 90/85 |
| Composition 7 | A1 = 10 | I-13 = 1.0 | — | D1 = 0.2 | 100/95 |
| Composition 8 | A1 = 10 | I-14 = 1.0 | — | D1 = 0.2 | 100/95 |
| Composition 9 | A1 = 10 | I-15 = 1.0 | — | D1 = 0.2 | 100/95 |
| Composition 10 | A1 = 10 | I-13 = 0.4 | B1-21 = 0.6 | D1 = 0.2 | 100/95 |
| Composition 11 | A1 = 10 | I-14 = 0.4 | B1-21/B1-22 = 0.2/0.4 | D1 = 0.2 | 100/95 |
| Composition 12 | A1 = 10 | I-14 = 0.6 | B1-22 = 0.4 | D1 = 0.2 | 100/95 |
| Composition 13 | A1 = 10 | I-57 = 1.0 | — | D1 = 0.2 | 100/95 |
| Composition 14 | A1 = 10 | I-75 = 0.4 | B1-21/B1-22 = 0.2/0.4 | D1 = 0.2 | 100/95 |
| Comparative Comp. 1 | A1 = 10 | — | B1-21/B1-22 = 0.6/0.4 | D1 = 0.2 | 90/85 |
| Comparative Comp. 2 | A1 = 10 | — | B1-21 = 1.0 | D1 = 0.2 | 90/85 |
| Comparative Comp. 3 | A1 = 10 | — | B1-22 = 1.0 | D1 = 0.2 | 90/85 |
| Comparative Comp. 4 | A1 = 10 | — | B1-X = 1.0 | D1 = 0.2 | 90/85 |

In Table 2, the symbols represent the following components.
<Resin>
A1: Resin A1 prepared by the method as described above
<Salt (I)>
1-13: Salt represented by the formula (1-13)
1-14: Salt represented by the formula (1-14
1-15: Salt represented by the formula (1-15)

The obtained wafer was then pre-baked for 60 seconds on a direct hot plate at the temperature given in the "PB" column in Table 2.

On the wafers on which the composition layer had thus been formed, the film was then exposed through a mask for forming line and space patterns (pitch: 200 nm, line: 100 nm) with changing exposure quantity stepwise, using an ArF excimer laser stepper for liquid-immersion lithography ("FPA 5000-AS3" by Canon Ltd.: NA=0.75, 2/3 Annular). Ultrapure water was used as medium for liquid-immersion.

After the exposure, post-exposure baking was carried out for 60 seconds at the temperature given in the "PEB" column in Table 2.

Then, development was carried out with 2.38 wt % of tetramethylammonium hydroxide (a product of Tokyo Chemical Industry Co., LTD) at 23° C. for 60 seconds in the manner of paddle development.

Effective sensitivity was defined as the exposure quantity at which the resist pattern with 100 nm-line width was obtained.

(Line Edge Roughness (LER) Evaluation)

The wall surface of the resist pattern following the lithography process was observed using a scanning electron microscope.

Table 3 illustrates the results thereof. The figures in parentheses represent the value (nm) of the maximum difference in width of the wall surface between the convex parts and the concavo parts.

TABLE 3

| | Composition | LER |
|---|---|---|
| Ex. 6 | Composition 1 | 7.48 |
| Ex. 7 | Composition 2 | 7.32 |
| Ex. 8 | Composition 3 | 7.49 |
| Ex. 9 | Composition 4 | 7.62 |
| Ex. 10 | Composition 5 | 7.58 |
| Ex. 11 | Composition 6 | 7.52 |
| Ex. 12 | Composition 7 | 7.32 |
| Ex. 13 | Composition 8 | 7.24 |
| Ex. 14 | Composition 9 | 7.26 |
| Ex. 15 | Composition 10 | 7.48 |
| Ex. 16 | Composition 11 | 7.45 |
| Ex. 17 | Composition 12 | 7.38 |
| Ex. 18 | Composition 13 | 7.36 |
| Ex. 19 | Composition 14 | 7.65 |
| Comp. Ex. 1 | Comp. Composition 1 | 7.88 |
| Comp. Ex. 2 | Comp. Composition 2 | 7.92 |
| Comp. Ex. 3 | Comp. Composition 3 | 7.89 |
| Comp. Ex. 4 | Comp. Composition 4 | 8.69 |

The salt of the disclosure and the acid generator containing the salt are useful for resist compositions. The resist composition which contains the salt shows satisfactory reduced LER. Therefore, the salt, the acid generator and the resist composition of the disclosure are useful for semiconductor microfabrication. The resist composition of the disclosure also shows satisfactory reduced LER for the resist patterns in a relatively thick film. Therefore, the resist composition is, in particular useful as a resist composition for an ion implantation.

What is claimed is:
1. A salt represented by formula (I):

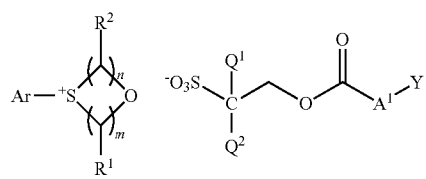

wherein $R^1$ and $R^2$ each independently represent a hydrogen atom, a hydroxy group or a $C_1$ to $C_{12}$ hydrocarbon group in which a methylene group may be replaced by an oxygen atom or a carbonyl group;
m and n each independently represent 1 or 2;
Ar represents an optionally substituted phenyl group;
$Q^1$ and $Q^2$ each independently represent a fluorine atom or a $C_1$ to $C_6$ perfluoroalkyl group,
$A^1$ represents a single bond, a $C_1$ to $C_{24}$ alkanediyl group or $*-A^2-X^1-(A^3-X^2)_a-(A^4)_b$,
* represents a binding site to a carbonyl group;
$A^2$, $A^3$ and $A^4$ each independently represent a $C_1$ to $C_6$ alkanediyl group,
$X^1$ and $X^2$ each independently represent —O—, —CO—O— or —O—CO—,
a represents 0 or 1,
b represents 0 or 1, and
Y represents a hydrogen atom or a monovalent $C_3$ to $C_{18}$ alicyclic hydrocarbon group where a hydrogen atom may be replaced by a substituent and where a methylene group may be replaced by an oxygen atom, a carbonyl group or a sulfonyl group, provided that the alicyclic hydrocarbon group has a substituent, or a methylene group contained in the alicyclic hydrocarbon group has been replaced by an oxygen atom, a carbonyl group or a sulfonyl group.

2. The salt according to claim 1, wherein $A^1$ is a single bond.

3. The salt according to claim 1, wherein Y is a $C_3$ to $C_{18}$ alicyclic hydrocarbon group where a hydrogen atom has been replaced by a substituent or where a methylene group has been replaced by an oxygen atom, a carbonyl group or a sulfonyl group.

4. An acid generator, which comprises the salt according to claim 1.

5. A resist composition comprising the salt according to claim 1 and a resin having an acid-labile group.

6. The resist composition according to claim 5, further comprising a salt which generates an acid weaker in acidity than an acid generated from the acid generator.

7. A method for producing a resist pattern comprising steps (1) to (5);
(1) applying the resist composition according to claim 5 onto a substrate;
(2) drying the applied composition to form a composition layer;
(3) exposing the composition layer;
(4) heating the exposed composition layer; and
(5) developing the heated composition layer.

* * * * *